United States Patent
Seth et al.

(10) Patent No.: US 7,666,854 B2
(45) Date of Patent: Feb. 23, 2010

(54) BIS-MODIFIED BICYCLIC NUCLEIC ACID ANALOGS

(75) Inventors: Punit P. Seth, Carlsbad, CA (US); Eric E. Swayze, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 12/331,226

(22) Filed: Dec. 9, 2008

(65) Prior Publication Data

US 2009/0156792 A1 Jun. 18, 2009

Related U.S. Application Data

(63) Continuation-in-part of application No. 11/747,057, filed on May 10, 2007, now Pat. No. 7,547,684.

(60) Provisional application No. 60/747,059, filed on May 11, 2006.

(51) Int. Cl.
*A01N 43/04* (2006.01)
*A61K 31/70* (2006.01)

(52) U.S. Cl. .................. 514/44; 514/42; 514/43; 536/22.1

(58) Field of Classification Search ............... None
See application file for complete search history.

(56) References Cited

U.S. PATENT DOCUMENTS

| | | | |
|---|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lableu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,069 E | 9/1992 | Koster et al. |
| 5,149,797 A | 9/1992 | Pederspn et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |

(Continued)

FOREIGN PATENT DOCUMENTS

WO WO 94/02499 2/1994

(Continued)

OTHER PUBLICATIONS

Agrawal, *Protocols for Oligonucleotides and Analogs* (1993) Humana Press.

(Continued)

*Primary Examiner*—Patrick T Lewis
(74) *Attorney, Agent, or Firm*—Jones Day

(57) ABSTRACT

The present disclosure describes bis-modified bicyclic nucleosides and oligomeric compounds that can be prepared comprising at least one of these bis-modified bicyclic nucleosides. More particularly, the bis-modified bicyclic nucleosides have at least one substituent group at the 5'-methylene and on the bridge methylene and can be chiral. These bis-modified bicyclic nucleosides are expected to be useful for enhancing one or more property of oligomeric compounds including for example enhancing nuclease resistance.

68 Claims, No Drawings

U.S. PATENT DOCUMENTS

| | | |
|---|---|---|
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,607,922 A | 3/1997 | De Clercq et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,830,653 A | 11/1998 | Froehler et al. |
| 6,005,096 A | 12/1999 | Matteucci et al. |
| 6,043,060 A | 3/2000 | Imanishi |
| 6,268,490 B1 | 7/2001 | Imanishi et al. |
| 6,426,220 B1 | 7/2002 | Bennett et al. |
| 6,436,640 B1 | 8/2002 | Simmons et al. |
| 6,600,032 B1 | 7/2003 | Manoharan et al. |
| 6,770,748 B2 | 8/2004 | Imanishi et al. |
| 6,794,499 B2 | 9/2004 | Wengel et al. |
| 7,053,207 B2 | 5/2006 | Wengel |
| 7,399,845 B2 | 7/2008 | Seth et al. |
| 2003/0082807 A1 | 5/2003 | Wengel |
| 2003/0087230 A1 | 5/2003 | Wengel |
| 2003/0105309 A1 | 6/2003 | Imanishi |
| 2003/0207841 A1 | 11/2003 | Kaneko et al. |
| 2003/0224377 A1 | 12/2003 | Wengel et al. |
| 2004/0014959 A1 | 1/2004 | Sorensen et al. |
| 2004/0143114 A1 | 7/2004 | Imanishi et al. |
| 2004/0192918 A1 | 9/2004 | Imanishi et al. |
| 2004/0219565 A1 | 11/2004 | Kauppinen et al. |

FOREIGN PATENT DOCUMENTS

| | | |
|---|---|---|
| WO | WO 94/17093 | 8/1994 |
| WO | WO 94/22890 | 10/1994 |
| WO | WO 98/39352 | 9/1998 |
| WO | WO 99/14226 | 3/1999 |
| WO | WO 02/36743 | 5/2002 |
| WO | WO 2005/012371 | 12/2005 |
| WO | WO 2005/012372 | 12/2005 |
| WO | WO 2007090071 | 8/2007 |

OTHER PUBLICATIONS

Altschul et al., "Basic Local Alignment Search Tool" J. Mol. Biol. (1990) 215:403-410.

Babu et al., J. Chem. Soc. (2002) Perkin Trans. 1, pp. 2509-2519.

Barany et al., "A New Amino Protecting Group Removable by Reduction. Chemistry of the Dithiasuccinoyl (Dts) Function" J. Am. Chem. Soc. (1977) 99:7363-7365.

Barany et al., "Kinetics and Mechanisms of the Thiolytic Removal of the Dithiasuccinoyl (Dts) Amino Protecting Group" J. Am. Chem. Soc. (1980) 102:3084-3095.

Bass, "Double-stranded RNA as a template for gene silencing" Cell (2000) 101:235-238.

Beaucage et al., "The Functionalization of Oligonucleotides via Phosphoramidite Derivatives" Tetrahedron (1993) 49:1925-1963.

Beaucage et al., "The Synthesis of Specific Ribonucleotides and Unrelated Phosphorylated Biomolecules by the Phosphoramidite Method" Tetrahedron (1993) 49:10441-10488.

Beaucage et al., "Advances in the Synthesis of Oligonucleotides by the Phosphoramidite Approach" Tetrahedron (1992) 48:2223-2311.

Beigelman et al., "Synthesis of 5'-C-Methyl-D-Allo- & L-Talo-Ribonucleoside 3'-O-Phosphoramidies and Their Incorporation into Hammerhead Ribozymes" Nucleoside Nucleotides (1995) 14:901-905.

Brazma et al., "Gene expression data analysis" FEBS Letters (2000) 480:17-24.

Carey et al., Advanced Organic Chemistry, Part B: Reactions and Synthesis 4th Ed. (2001) Kluwer Academic/Plenum Publisher, New York.

Carulli et al., "High Throughput Analysis of Differential Gene Expression" J. Cell. Biochem. Suppl. (1998) 30:286-296.

Celis et al., "Gene expression profiling: monitoring transcription and translation products using DNA microarrays and proteomics" FEBS Lett (2000) 480:2-16.

Chiang et al., "Antisense Oligonucleotides Inhibit Intercellular Adhesion Molecule 1 Expression by Two Distinct Mechanisms" J. Biol. Chem. (1991) 266:18162-18171.

Eckstein, Oligonucleotides and Analogues, a Practical Approach (1991) Oxford Univ. Press, NY.

Elbashir, "Duplexes of 21-nucleotide RNAs mediate RNA interference in cultured mammalian cells" Nature (2001) 411:494-498.

Elbashir, "RNA interference is mediated by 21- and 22-nucleotide RNAs" Genes & Devel. (2001) 15:188-200.

Englisch et al., "Chemically Modified Oligonucleotides as Probes and Inhibitors" Agnew Chem. Int. Ed. Engl. (1991) 30:613-629.

Fire et al., "Potent and Specific Genetic Interference by Double-Stranded RNA in *Caenorhabditis elegans*" Nature (1998) 391:806-811.

Fuchs et al., "Identification of Differentially Expressed Genes by Mutually Subtracted RNA Fingerprinting" Anal. Biochem. (2000) 286:91-98.

Gait, "Oligoribonucleotides" Antisense Research and Applications (1993), CRC Press, Boca Raton, pp. 289-301.

Gait et al., "Application of chemically synthesized RNA" RNA: Protein Interactions (1998) 1-36.

Gallo et al., "2'-C-Methyluridine Phosphoramidite: A New Building Block for the Preparation of RNA Analogues Carrying the 2'-Dydroxyl Group" Tetrahedron (2001) 57: 5707-5713.

Going et al., "Molecular Pathology and Future Developments" Eur. J. Cancer (1999) 35:1895-1904.

Hari et al., "Synthesis and properties of oligonucleotides containing novel 2',4'-BNA analogues (2',4'-BNAcoc)" *Nucleic Acids Research Supplement* No. 2 (2002) 147-148.

Hornbeck et al., "Enzyme-Linked Immunosorbet Assays (ELISA)" Curr. Protocols Mol. Biol. (1991) John Wiley & Sons 11.2.1-11.2.22.

International Search Report for PCT/US2007/061183 dated Jan. 27, 2007.

International Search Report for PCT/US2007/068690 dated Nov. 30, 2007.

Jungblut et al., "Proteomics in human disease: Cancer, heart and infections diseases" Electrophoresis (1999) 20:2100-2110.

Jurecic et al., "Long-distance DD-PCR and cDNA microarrays" Curr. Opin. Microbiol. (2000) 3:316-321.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Kroschwitz, "Polynucleotides" Concise Encyclopedia of Polymer Science and Engineering (1990) John Wiley & Sons, NY pp. 858-859.

Kumar et al., "The first analogues of LNA (locked nucleic acids): phosphorothioate-LNA and 2'-thio-LNA" Bioorg Med Chem Lett. (1998) 8:2219-2222.

Lane et al., "NMR assignments and solution conformation of the DNA:RNA hybrid duplex d(GTGAACTT)r(AAGUUCAC)" Eur. J. Biochem. (1993) 215:297-306.

Larson et al., "Rapid DNA Fingerprinting of Pathogens by Flow Cytometry" Cytometry (2000) 41:203-208.

Larsson et al., "High-throughput protein expression of cDNA products as a tool in functional genomics" J. Biotech. (2000) 80:143-157.

Madden et al., "Serial analysis of gene expression: from gene discovery to target identification" DDT (2000) 5:415-425.

Mikhailov et al., "Substrate Properties of C'-Methylnucleoside and C'-Methyl-2'-Deoxynucleoside 5'-Triphosphates in RNA and DNA Synthesis Reactions Catalysed by RNA and DNA Polymerase" Nucleosides Nucleotides (1991) 10:339-343.

Montgomery et al., "RNA as a target of double-stranded RNA-mediated genetic interference in *Caenorhabditis elegans*" Proc Natl. Acad. Sci. (1998) 95:15502-7.

Nishikura, "A Short Primer on RNAi: RNA-Directed RNA Polymerase Acts as a Key Catalyst" Cell (2001) 107:415-418.

Prashar et al., "READS: A Method for Display of 3'-End Fragment of Restriction Enzyme-Digested cDNAs for Analysis of Differential Gene Expression" Methods Enzymol. (1999) 303:258-272.

Saha et al., "5'-Me-DNA—A New Oligonucleotide Analog: Synthesis and Biochemical Properties" J. Org. Chem. (1995) 60:788-789.

Sanghvi, Chapter 15, Antisense Research and Applications, pp. 289-302, Crooke and Lebleu ed., CRC Press (1993).

Scaringe, "RNA Oligonucleotide Synthesis via 5'-Silyl-2'-Orthoester Chemistry" Methods (2001) 23:206-217.

Singh et al., "Synthesis of 2'-amino-LNA: A novel conformationally restricted high-affinity oligonucleotide analogue with a handle" J. Org. Chem. (1998) 63: 10035-10039.

Singh et al., "LNA (locked nucleic acids): synthesis and high-affinity nucleic acid recognition" Chem. Commun. (1998) 455-456.

Sonveaux, "Protecting Groups in Oligonucleotide Synthesis" Protocols for Oligonucleotide Conjugates (1994) 26:1-71.

Sutcliffe et al., "TOGA: An automated parsing technology for analyzing expression of nearly all genes" PNAS (2000) 97:1976-1981.

Swayze et al., "Antisense oligonucleotides containing locked nucleic acid improve potency but cause significant hepatotoxicity in animals" Nucleic Acids Res. (2007) 35:687-700.

Tabara et al., "RNAi in *C. elegans*: Soaking in the Genome Sequence" Science (1998) 282:430-431.

Tijsterman et al., "RNA hellcase MUT-14-dependent gene silencing triggered in *C. elegans* by short antisense RNAs" Science (2002) 295:694-7.

Timmons et al., "Specific Interference by Ingested dsRNA" Nature (1998) 395:854.

Timmons et al., "Ingestion of bacterially expressed dsRNAs can produce specific and potent genetic interference in *Caenorhabditis elegans*" Gene (2001) 263:103-112.

To, "Identification of Differential Gene Expression by High Throughput Analysis" Comb. Chem. High Throughput Screen (2000) 3:235-241.

Tuschl et al., "Targeted mRNA degradation by double-stranded RNA in vitro" Genes Dev. (1999) 13:3191-7.

Wahlestedt et al., "Potent and nontoxic antisense oligonucleotide containing locked nucleic acids" Proc. Natl. Acad. Sci. USA (2000) 97: 5633-5638.

Wang et al., "5'-C-Branched Thymidines: Synthesis, Sterochemistry, and Incorporation into Oligodeoxynucleotides" Tetrahedron Letters (1996) 37:2739-2742.

Wang et al., "Biophysical and Biochemical Properties of Oligodeoxynucleotides Containing 4'-C- and 5'-C-Substituted Thymidines" Bioorg. Med. Chem. Lett. (1999) 9:885-890.

Youssefyeh et al., "4'-Substituted Nucleosides. 4. Synthesis of some 4'-Hydroxymethyl Nucleosides" J. Org. Chem. (1979) 44:1301-1309.

Zhang et al., "PowerBLAST: A New Network BLAST Application for Interactive or Automated Sequence Analysis and Annotation" Genome Res. (1997) 7:649-656.

SEQUENCE LISTING

<160> NUMBER OF SEQ ID NOS: 15

<210> SEQ ID NO 1
<211> LENGTH: 3160
<212> TYPE: DNA
<213> ORGANISM: Homo Sapiens

<400> SEQUENCE: 1

```
cctcccctcg cccggcgcgg tcccgtccgc ctctcgctcg cctcccgcct cccctcggtc     60
ttccgaggcg cccgggctcc cggcgcggcg gcggaggggg cgggcaggcc ggcgggcggt    120
gatgtggcag gactctttat gcgctgcggc aggatacgcg ctcggcgctg ggacgcgact    180
gcgctcagtt ctctcctctc ggaagctgca gccatgatgg aagtttgaga gttgagccgc    240
tgtgaggcga ggccgggctc aggcgaggga gatgagagac ggcggcggcc gcggcccgga    300
gcccctctca gcgcctgtga gcagccgcgg gggcagcgcc ctcggggagc cggccggcct    360
gcggcggcgg cagcggcggc gtttctcgcc tcctcttcgt cttttctaac cgtgcagcct    420
```

```
cttcctcggc ttctcctgaa agggaaggtg gaagccgtgg gctcgggcgg gagccggctg    480
aggcgcggcg gcggcggcgg cggcacctcc cgctcctgga gcgggggggga gaagcggcgg    540 cggcggcggc cgcggcggct gcagctccag ggagggggtc tgagtcgcct gtcaccattt    600
ccagggctgg gaacgccgga gagttggtct ctccccttct actgcctcca acacggcggc    660
ggcggcggcg gcacatccag ggacccgggc cggttttaaa cctcccgtcc gccgccgccg    720 cacccccccgt ggcccgggct ccggaggccg ccggcggagg cagccgttcg gaggattatt    780
cgtcttctcc ccattccgct gccgccgctg ccaggcctct ggctgctgag gagaagcagg    840
cccagtcgct gcaaccatcc agcagccgcc gcagcagcca ttacccggct gcggtccaga    900
gccaagcggc ggcagagcga ggggcatcag ctaccgccaa gtccagagcc atttccatcc    960
tgcagaagaa gccccgccac cagcagcttc tgccatctct ctcctccttt tcttcagcc    1020 acaggctccc agacatgaca gccatcatca aagagatcgt tagcagaaac aaaaggagat    1080
atcaagagga tggattcgac ttagacttga cctatattta tccaaacatt attgctatgg    1140
gatttcctgc agaaagactt gaaggcgtat acaggaacaa tattgatgat gtagtaaggt    1200
ttttggattc aaagcataaa aaccattaca agatatacaa tctttgtgct gaaagacatt    1260
atgacaccgc caaatttaat tgcagagttg cacaatatcc ttttgaagac cataacccac    1320
cacagctaga acttatcaaa ccccttttgtg aagatcttga ccaatggcta agtgaagatg    1380
acaatcatgt tgcagcaatt cactgtaaag ctggaaaggg acgaactggt gtaatgatat    1440
gtgcatattt attacatcgg ggcaaatttt taaaggcaca agaggcccta gatttctatg    1500
gggaagtaag gaccagagac aaaaagggag taactattcc cagtcagagg cgctatgtgt    1560
attattatag ctacctgtta aagaatcatc tggattatag accagtggca ctgttgtttc    1620
acaagatgat gtttgaaact attccaatgt tcagtggcgg aacttgcaat cctcagtttg    1680
tggtctgcca gctaaaggtg aagatatatt cctccaattc aggacccaca cgacgggaag    1740
acaagttcat gtactttgag ttccctcagc cgttacctgt gtgtggtgat atcaaagtag    1800
agttcttcca caaacagaac aagatgctaa aaaaggacaa aatgtttcac ttttgggtaa    1860
atacattctt cataccagga ccagaggaaa cctcagaaaa agtagaaaat ggaagtctat    1920
gtgatcaaga aatcgatagc atttgcagta tagagcgtgc agataatgac aaggaatatc    1980
tagtacttac tttaacaaaa aatgatcttg acaaagcaaa taaagacaaa gccaaccgat    2040
acttttctcc aaattttaag gtgaagctgt acttcacaaa aacagtagag gagccgtcaa    2100
atccagaggc tagcagttca acttctgtaa caccagatgt tagtgacaat gaacctgatc    2160
attatagata ttctgacacc actgactctg atccagagaa tgaaccttttt gatgaagatc    2220 agcatacaca aattacaaaa gtctgaattt tttttttatca agagggataa acaccatga    2280 aaataaactt gaataaactg aaaatggacc ttttttttttt taatggcaat aggacattgt    2340
gtcagattac cagttatagg aacaattctc ttttcctgac caatcttgtt ttaccctata    2400
catccacagg gttttgacac ttgttgtcca gttgaaaaaa ggttgtgtag ctgtgtcatg    2460
tatatacctt tttgtgtcaa aaggacattt aaaattcaat taggattaat aaagatggca    2520
ctttcccgtt ttattccagt tttataaaaa gtgggagacag actgatgtgt atacgtagga    2580
attttttcct tttgtgttct gtcaccaact gaagtggcta aagagctttg tgatatactg    2640
gttcacatcc taccccttttg cacttgtggc aacagataag tttgcagttg gctaagagag    2700
gtttccgaaa ggtttttgcta ccattctaat gcatgtattc gggttagggc aatggagggg    2760
```

```
aatgctcaga aaggaaataa ttttatgctg gactctggac catataccat ctccagctat    2820
ttacacacac ctttctttag catgctacag ttattaatct ggacattcga ggaattggcc    2880
gctgtcactg cttgttgttt gcgcattttt ttttaaagca tattggtgct agaaaaggca    2940
gctaaaggaa gtgaatctgt attggggtac aggaatgaac cttctgcaac atcttaagat    3000
ccacaaatga agggatataa aaataatgtc ataggtaaga aacacagcaa caatgactta    3060
accatataaa tgtggaggct atcaacaaag aatgggcttg aaacattata aaaattgaca    3120
atgatttatt aaatatgttt tctcaattgt aaaaaaaaaa                          3160
```

```
<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
aatggctaag tgaagatgac aatcat                                         26

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
tgcacatatc attacaccag ttcgt                                          25

<210> SEQ ID NO 4
<211> LENGTH: 30
<212> TYPE: DNA
<213> ORGANISM: Artificial Sequence
<220> FEATURE:
<223> OTHER INFORMATION: Probe

<400> SEQUENCE: 4
ttgcagcaat tcactgtaaa gctggaaagg                                     30

<210> SEQ ID NO 5
<211> LENGTH: 14
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1,2,13,14
<223> OTHER INFORMATION: bases at these positions are RNA

<400> SEQUENCE: 5
cutagcactg gccu                                                      14

<210> SEQ ID NO 6
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 6
tttttttttt tt                                                        12
```

```
<210> SEQ ID NO 7
<211> LENGTH: 12
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 11, 12
<223> OTHER INFORMATION: bases at these positions are RNA

<400> SEQUENCE: 7
tttttttttt uu                                                              12

<210> SEQ ID NO 8
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 8
cttagcactg gcct                                                            14

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 9
ctgctagcct ctggatttga                                                      20

<210> SEQ ID NO 10
<211> LENGTH: 14
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1, 2, 13, 14
<223> OTHER INFORMATION: bases at these positions are 5'-(S)-CH3-BNA

<400> SEQUENCE: 10
ucatggctgc agcu                                                            14

<210> SEQ ID NO 11
<211> LENGTH: 14
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1, 2, 13, 14
<223> OTHER INFORMATION: bases at these positions are 4'-CH2-O-2'BNA

<400> SEQUENCE: 11
tcatggctgc agct                                                            14

<210> SEQ ID NO 12
<211> LENGTH: 18
<212> TYPE: DNA
<213> ORGANISM: Artificial Sequence
<220> FEATURE:
<223> OTHER INFORMATION: Synthetic Oligonucleotide
```

```
-continued

<400> SEQUENCE: 12
ctgctagcct ctggattt                                                       18

<210> SEQ ID NO 13
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1,2,17,18
<223> OTHER INFORMATION: bases at these positions are RNA

<400> SEQUENCE: 13
cugctagcct ctggatuu                                                       18

<210> SEQ ID NO 14
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 14
ucaaauccag aggcuagcag                                                     20

<210> SEQ ID NO 15
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 15
aggccagugc uaag                                                           14
```

BIS-MODIFIED BICYCLIC NUCLEIC ACID ANALOGS

CROSS-REFERENCE TO RELATED APPLICATIONS

The present application is a continuation in part of pending U.S. application Ser. No. 11/747,057 filed May 10, 2007, which claims benefit to U.S. Provisional Application Ser. No. 60/747,059 filed May 11, 2006, each of which are incorporated herein by reference in their entirety.

SEQUENCE LISTING

The present application is being filed along with a Sequence Listing in electronic format. The Sequence Listing is provided as a file entitled CHEM0029US.P1SEQ.TXT, created on Dec. 9, 2008 which is 8 Kb in size. The information in the electronic format of the sequence listing is incorporated herein by reference in its entirety.

FIELD OF THE INVENTION

Provided herein are novel bis-modified bicyclic nucleosides and oligomeric compounds prepared therefrom. More particularly, the bis modified bicyclic nucleosides each have at least one non H substituent group "Q" located on the bridge (2'-O—C($Q_1$)($Q_2$)-4') and at least one further non H substituent group "Z" located on the 5'-methylene group [5'-C($Z_2$)($Z_2$)]. The bis-substituted bicyclic nucleosides are expected to be useful for enhancing one or more properties of the oligomeric compounds they are incorporated into such as for example nuclease resistance.

BACKGROUND OF THE INVENTION

Antisense technology is an effective means for reducing the expression of one or more specific gene products and can therefore prove to be uniquely useful in a number of therapeutic, diagnostic, and research applications. Chemically modified nucleosides are routinely used for incorporation into antisense sequences to enhance one or more properties such as for example nuclease resistance. One such group of chemical modifications includes bicyclic nucleosides wherein the furanose portion of the nucleoside includes a bridge connecting two atoms on the furanose ring thereby forming a bicyclic ring system. Such bicyclic nucleosides have various names including BNA's and LNA's for bicyclic nucleic acids or locked nucleic acids respectively.

Various BNA's have been prepared and reported in the patent literature as well as in scientific literature, see for example: Singh et al., Chem. Commun., 1998, 4, 455-456; Koshkin et al., *Tetrahedron*, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Wengel et al., PCT International Application number PCT/DK98/00303 (published as WO 99/14226 on Mar. 25, 1999), filed Sep. 14, 1998; Singh et al., J. Org. Chem., 1998, 63, 10035-10039, the text of each is incorporated by reference herein, in their entirety. Examples of issued US patents and published applications include for example: U.S. Pat. Nos. 6,770,748, 6,268,490 and 6,794,499 and published U.S. applications 20040219565, 20040014959, 20030207841, 20040192918, 20030224377, 20040143114, 20030087230 and 20030082807, the text of each is incorporated by reference herein, in their entirety.

Various 5'-modified nucleosides have been prepared and reported in the patent literature as well as in scientific literature, see for example: Mikhailov et al., *Nucleosides and Nucleotides*, 1991, 10, 393-343; Saha et al., *J. Org. Chem.*, 1995, 60, 788-789; Beigleman et al., *Nucleosides and Nucleotides*, 1995, 14, 901-905; Wang, et al., *Bioorganic & Medicinal Chemistry Letters,* 1999, 9, 885-890; and PCT International Application WO94/22890 published Oct. 13, 1994, the text of each is incorporated by reference herein, in their entirety.

Bicyclic nucleosides having a single substituent group on the bridge e.g. a 6-substituent group (4'-CH(R)—O-2') and oligomeric compounds incorporating these nucleosides have been reported in a commonly owned issued U.S. Pat. No. 7,339,845, issued Jul. 15, 2008, the text of which is incorporated by reference herein, in its entirety. Bicyclic nucleosides having two substituent groups on the bridge (4'-C($R_1$)($R_2$)—O-2') and oligomeric compounds incorporating these nucleosides have been reported in commonly owned published International Application, WO 2007/090071 Published Aug. 9, 2007, the text of which is incorporated by reference herein, in its entirety.

Consequently, there remains an ongoing need for agents that specifically regulate gene expression via antisense mechanisms. Disclosed herein are bis-modified bicyclic nucleosides and antisense compounds prepared therefrom that are expected to be useful for modulating gene expression pathways, including those relying on mechanisms of action such as RNaseH, RNAi and dsRNA enzymes, as well as other antisense mechanisms based on target degradation or target occupancy. One having skill in the art, once armed with this disclosure will be able, without undue experimentation, to identify, prepare and exploit antisense compounds for these uses.

BRIEF SUMMARY OF THE INVENTION

Provided herein are novel bis-modified bicyclic nucleosides and oligomeric compounds prepared therefrom. More particularly, the bis modified bicyclic nucleosides each have at least one non H substituent group "Q" located on the bridge (2'-O—C($Q_1$)($Q_2$)-4') and at least one further non H substituent group "Z" located on the 5'-methylene group [5'-C($Z_2$)($Z_2$)]. The bis-substituted bicyclic nucleosides are expected to be useful for enhancing one or more properties of the oligomeric compounds they are incorporated into such as for example nuclease resistance. In certain embodiments, the oligomeric compounds and compositions provided herein that incorporate one or more of the bis-substituted bicyclic nucleosides are expected to hybridize to a portion of a target RNA resulting in loss of normal function of the target RNA.

The variables are defined individually in further detail herein. It is to be understood that the bis-substituted bicyclic nucleosides provided herein and the oligomeric compounds comprising at least one of these bis-substituted bicyclic nucleosides include all combinations of the embodiments disclosed and variables defined herein.

In certain embodiments, bicyclic nucleosides are provided herein having Formula I:

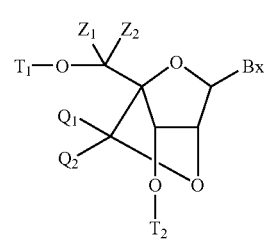

wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

one of $Z_1$ and $Z_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other one of $Z_1$ and $Z_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

one of $Q_1$ and $Q_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol and the other one of $Q_1$ and $Q_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol;

or $Q_1$ and $Q_2$ together are methylene (=$CH_2$);

each substituted group is mono or poly substituted with substituent groups independently selected from halogen, $OJ_1$, $SJ_1$, $NJ_1J_2$, $N_3$, $COOJ_1$, CN, O—C(=O)$NJ_1J_2$, N(H)C(=NH)$NJ_1J_2$, N(H)C(=O)N(H)$J_2$ or N(H)C(=S)N(H)$J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, $Z_1$ and $Z_2$ are each, independently, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl. In certain embodiments, $Z_1$ and $Z_2$ are each $CH_3$. In certain embodiments, one of $Z_1$ and $Z_2$ is H. In certain embodiments, one of $Z_1$ and $Z_2$ is H and the other one of $Z_1$ and $Z_2$ is substituted $C_1$-$C_6$ alkyl. In certain embodiments, one of $Z_1$ and $Z_2$ is H and the other one of $Z_1$ and $Z_2$ is $CH_2F$, $CHF_2$ or $CF_3$. In certain embodiments, one of $Z_1$ and $Z_2$ is H and the other one of $Z_1$ and $Z_2$ is $C_1$-$C_6$ alkyl. In certain embodiments, one of $Z_1$ and $Z_2$ is H and the other one of $Z_1$ and $Z_2$ is $CH_3$.

In certain embodiments, $Q_1$ and $Q_2$ are each, independently, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol. In certain embodiments, $Q_1$ and $Q_2$ are each $CH_3$. In certain embodiments, one of $Q_1$ and $Q_2$ is H. In certain embodiments, one of $Q_1$ and $Q_2$ is H and the other one of $Q_1$ and $Q_2$ is substituted $C_1$-$C_6$ alkyl. In certain embodiments, one of $Q_1$ and $Q_2$ is H and one of $Q_1$ and $Q_2$ is $CH_2F$, $CHF_2$ or $CF_3$. In certain embodiments, one of $Q_1$ and $Q_2$ is H and the other one of $Q_1$ and $Q_2$ is $C_1$-$C_6$ alkyl. In certain embodiments, one of $Q_1$ and $Q_2$ is H and the other one of $Q_1$ and $Q_2$ is $CH_3$.

In certain embodiments, $Q_1$ and $Q_2$ together are methylene (=$CH_2$). In certain embodiments, $Q_1$ and $Q_2$ together are methylene (=$CH_2$), one of $Z_1$ and $Z_2$ is $CH_3$ and the other one of $Z_1$ and $Z_2$ is H.

In certain embodiments, bicyclic nucleosides are provided herein having Formula II:

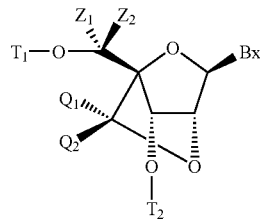

II wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

one of $Z_1$ and $Z_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other one of $Z_1$ and $Z_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

one of $Q_1$ and $Q_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol and the other one of $Q_1$ and $Q_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol;

or $Q_1$ and $Q_2$ together are methylene (=$CH_2$);

each substituted group is mono or poly substituted with substituent groups independently selected from halogen, $OJ_1$, $SJ_1$, $NJ_1J_2$, $N_3$, $COOJ_1$, CN, O—C(=O)$NJ_1J_2$, N(H)C(=NH)$NJ_1J_2$, N(H)C(=O)N(H)$J_2$ or N(H)C(=S)N(H)$J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, bicyclic nucleosides are provided having Formula II wherein $Z_2$ and $Q_2$ are each H. In certain embodiments, bicyclic nucleosides are provided having Formula II wherein $Z_2$ and $Q_2$ are each H and $Z_1$ and $Q_1$ are each $CH_3$.

In certain embodiments, bicyclic nucleosides are provided having Formula II wherein $Z_2$ and $Q_1$ are each H. In certain embodiments, bicyclic nucleosides are provided having Formula II wherein $Z_2$ and $Q_1$ are each H and $Z_1$ and $Q_2$ are each $CH_3$.

In certain embodiments, bicyclic nucleosides are provided having Formula II wherein $Z_1$ and $Q_2$ are each H. In certain embodiments, bicyclic nucleosides are provided having Formula II wherein $Z_1$ and $Q_2$ are each H and $Z_2$ and $Q_1$ are each $CH_3$.

In certain embodiments, bicyclic nucleosides are provided having Formula II wherein $Z_1$ and $Q_1$ are each H. In certain embodiments, bicyclic nucleosides are provided having Formula II wherein $Z_1$ and $Q_1$ are each H and $Z_2$ and $Q_2$ are each $CH_3$.

In certain embodiments, Bx is uracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4-benzoxazin-2(3H)-one), 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',2':4,5]pyrrolo[2,3-d]pyrimidin-2-one. In certain embodiments, Bx is uracil, thymine, cytosine, 5-methylcytosine, 2,6-diaminopurine, adenine or guanine.

In certain embodiments, $T_1$ is selected from acetyl, benzyl, t-butyldimethylsilyl, t-butyl-diphenylsilyl and dimethoxytrityl. In certain embodiments, $T_1$ is 4,4'-dimethoxytrityl. In certain embodiments, $T_2$ is a reactive phosphorus group. In certain embodiments, $T_2$ is a reactive phosphorus group selected from diisopropylcyanoethoxy phosphoramidite or H-phosphonate. In certain embodiments, $T_1$ is 4,4'-dimethoxytrityl and $T_2$ is diisopropylcyanoethoxy phosphoramidite.

In certain embodiments, oligomeric compounds are provided herein having at least one bicyclic nucleoside of Formula III:

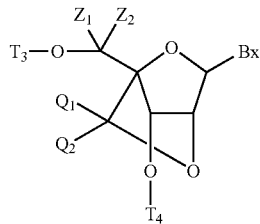

III wherein independently for each bicyclic nucleoside having Formula III:

Bx is a heterocyclic base moiety;

$T_3$ and $T_4$ are each, independently, an internucleoside linking group linking the bicyclic nucleoside of Formula III to the oligomeric compound or one of $T_3$ and $T_4$ is an internucleoside linking group linking the bicyclic nucleoside of Formula III to the oligomeric compound and the other of $T_3$ and $T_4$ is H, a hydroxyl protecting group, a linked conjugate group or a 5' or 3'-terminal group;

one of $Z_1$ and $Z_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other one of $Z_1$ and $Z_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

one of $Q_1$ and $Q_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol and the other one of $Q_1$ and $Q_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol;

or $Q_1$ and $Q_2$ together are methylene (=$CH_2$);

each substituted group is mono or poly substituted with substituent groups independently selected from halogen, $OJ_1$, $SJ_1$, $NJ_1J_2$, $N_3$, $COOJ_1$, $CN$, O—C(=O)$NJ_3J_2$, N(H)C(=NH)$NJ_1J_2$, N(H)C(=O)N(H)$J_2$ or N(H)C(=S)N(H)$J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, $Z_1$ and $Z_2$ are each, independently, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl for essentially each bicyclic nucleoside having Formula III. In certain embodiments, $Z_1$ and $Z_2$ are each $CH_3$ for essentially each bicyclic nucleoside having Formula III.

In certain embodiments, one of $Z_1$ and $Z_2$ is H for essentially each bicyclic nucleoside having Formula III. In certain embodiments, one of $Z_1$ and $Z_2$ is H and the other one of $Z_1$ and $Z_2$ is substituted $C_1$-$C_6$ alkyl for essentially each bicyclic nucleoside having Formula III. In certain embodiments, one of $Z_1$ and $Z_2$ is H and the other one of $Z_1$ and $Z_2$ is $CH_2F$, $CHF_2$ or $CF_3$ for essentially each bicyclic nucleoside having Formula III. In certain embodiments, one of $Z_1$ and $Z_2$ is H and the other one of $Z_1$ and $Z_2$ is $C_1$-$C_6$ alkyl for essentially each bicyclic nucleoside having Formula III. In certain embodiments, one of $Z_1$ and $Z_2$ is H and the other one of $Z_1$ and $Z_2$ is $CH_3$ for essentially each bicyclic nucleoside having Formula III.

In certain embodiments, $Q_1$ and $Q_2$ are each, independently, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol for essentially each bicyclic nucleoside having Formula III. In certain embodiments, $Q_1$ and $Q_2$ are each $CH_3$ for essentially each bicyclic nucleoside having Formula III.

In certain embodiments, one of $Q_1$ and $Q_2$ is H for essentially each bicyclic nucleoside having Formula III. In certain embodiments, one of $Q_1$ and $Q_2$ is H and the other one of $Q_1$ and $Q_2$ is substituted $C_1$-$C_6$ alkyl for essentially each bicyclic nucleoside having Formula III. In certain embodiments, one of $Q_1$ and $Q_2$ is H and other one of $Q_1$ and $Q_2$ is $CH_2F$, $CHF_2$ or $CF_3$ for essentially each bicyclic nucleoside having Formula III. In certain embodiments, one of $Q_1$ and $Q_2$ is H and the other one of $Q_1$ and $Q_2$ is $C_1$-$C_6$ alkyl for essentially each bicyclic nucleoside having Formula III. In certain embodiments, one of $Q_1$ and $Q_2$ is H and the other one of $Q_1$ and $Q_2$ is $CH_3$ for essentially each bicyclic nucleoside having Formula III.

In certain embodiments, $Q_1$ and $Q_2$ together are methylene (=$CH_2$) for essentially each bicyclic nucleoside having Formula III. In certain embodiments, $Q_1$ and $Q_2$ together are methylene (=$CH_2$), one of $Z_1$ and $Z_2$ is $CH_3$ and the other one of $Z_1$ and $Z_2$ is H for essentially each bicyclic nucleoside having Formula III.

In certain embodiments, oligomeric compounds are provided herein having at least one bicyclic nucleoside of Formula IV:

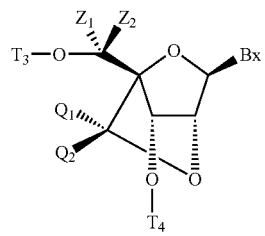

IV wherein independently for each bicyclic nucleoside having Formula IV:

Bx is a heterocyclic base moiety;

$T_3$ and $T_4$ are each, independently, an internucleoside linking group linking the bicyclic nucleoside of Formula IV to the oligomeric compound or one of $T_3$ and $T_4$ is an internucleoside linking group linking the bicyclic nucleoside of Formula IV to the oligomeric compound and the other of $T_3$ and $T_4$ is H, a hydroxyl protecting group, a linked conjugate group or a 5' or 3'-terminal group;

one of $Z_1$ and $Z_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other one of $Z_1$ and $Z_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

one of $Q_1$ and $Q_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol and the other one of $Q_1$ and $Q_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol;

or $Q_1$ and $Q_2$ together are methylene (=$CH_2$);

each substituted group is mono or poly substituted with substituent groups independently selected from halogen, $OJ_1$, $SJ_1$, $NJ_1J_2$, $N_3$, $COOJ_1$, $CN$, O—C(=O)$NJ_1J_2$, N(H)C(=NH)$NJ_1J_2$, N(H)C(=O)N(H)$J_2$ or N(H)C(=S)N(H)$J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, oligomeric compounds are provided comprising at least one bicyclic nucleoside having Formula IV wherein $Z_2$ and $Q_2$ are each H for essentially each bicyclic nucleoside having Formula IV. In certain embodiments, oligomeric compounds are provided comprising at least one bicyclic nucleoside having Formula IV wherein $Z_2$ and $Q_2$ are each H and $Z_1$ and $Q_1$ are each $CH_3$ for essentially each bicyclic nucleoside having Formula IV.

In certain embodiments, oligomeric compounds are provided comprising at least one bicyclic nucleoside having Formula IV wherein $Z_2$ and $Q_1$ are each H for essentially each bicyclic nucleoside having Formula IV. In certain embodiments, oligomeric compounds are provided comprising at least one bicyclic nucleoside having Formula IV wherein $Z_2$ and $Q_1$ are each H and $Z_1$ and $Q_2$ are each $CH_3$ for essentially each bicyclic nucleoside having Formula IV.

In certain embodiments, oligomeric compounds are provided comprising at least one bicyclic nucleoside having Formula IV wherein $Z_1$ and $Q_2$ are each H for essentially each bicyclic nucleoside having Formula IV. In certain embodiments, oligomeric compounds are provided comprising at least one bicyclic nucleoside having Formula IV wherein $Z_1$ and $Q_2$ are each H and $Z_2$ and $Q_1$ are each $CH_3$ for essentially each bicyclic nucleoside having Formula IV.

In certain embodiments, oligomeric compounds are provided comprising at least one bicyclic nucleoside having Formula IV wherein $Z_1$ and $Q_1$ are each H for essentially each bicyclic nucleoside having Formula IV. In certain embodiments, oligomeric compounds are provided comprising at least one bicyclic nucleoside having Formula IV wherein $Z_1$ and $Q_1$ are each H and $Z_2$ and $Q_2$ are each $CH_3$ for essentially each bicyclic nucleoside having Formula IV.

In certain embodiments, Bx is uracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4]benzoxazin-2(3H)-one), 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',2':4,5]pyrrolo[2,3-d]pyrimidin-2-one for essentially each bicyclic nucleoside having Formula IV. Bx is uracil, thymine, cytosine, 5-methylcytosine, 2,6-diaminopurine, adenine or guanine for essentially each bicyclic nucleoside having Formula IV.

In certain embodiments, oligomeric compounds are provided wherein each internucleoside linking group is, independently, a phosphodiester or phosphorothioate. In certain embodiments, oligomeric compounds are provided wherein each internucleoside linking group is a phosphorothioate.

In certain embodiments, oligomeric compounds are provided comprising at least two regions wherein each region independently comprises at least two contiguous bicyclic nucleosides having Formula III and wherein the two regions are separated by a plurality of monomeric subunits. In certain embodiments the plurality of monomeric subunits comprise a plurality of β-D-2'-deoxyribofuranosyl nucleosides. In certain embodiments, the monomeric subunits comprise only β-D-2'-deoxyribofuranosyl nucleosides.

In certain embodiments, oligomeric compounds are provided comprising from about 8 to about 40 monomeric subunits. In certain embodiments, oligomeric compounds are provided comprising from about 8 to about 20 monomeric subunits. In certain embodiments, oligomeric compounds are provided comprising from about 10 to about 16 monomeric subunits. In certain embodiments, oligomeric compounds are provided comprising from about 10 to about 14 monomeric subunits.

DETAILED DESCRIPTION OF THE INVENTION

Provided herein are novel bis-modified bicyclic nucleosides and oligomeric compounds prepared therefrom. More particularly, the bis modified bicyclic nucleosides each have at least one non H substituent group "Q" located on the bridge (2'-O—C($Q_1$)($Q_2$)-4') and at least one further non H substituent group "Z" located on the 5'-methylene group [5'-C($Z_2$)($Z_2$)]. The bis-substituted bicyclic nucleosides are expected to be useful for enhancing one or more properties of the oligomeric compounds they are incorporated into such as for example nuclease resistance. In certain embodiments, the oligomeric compounds and compositions provided herein that incorporate one or more of the bis-substituted bicyclic nucleosides are expected to hybridize to a portion of a target RNA resulting in loss of normal function of the target RNA. The oligomeric compounds are also expected to be useful as primers and probes in diagnostic applications.

In certain embodiments, bicyclic nucleosides are provided having Formula I:

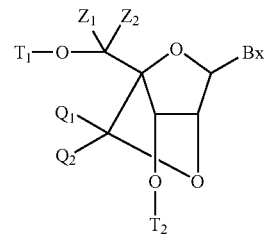

I wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

one of $Z_1$ and $Z_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other one of $Z_1$ and $Z_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

one of $Q_1$ and $Q_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol and the other one of $Q_1$ and $Q_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol;

or $Q_1$ and $Q_2$ together are methylene (=$CH_2$);

each substituted group is mono or poly substituted with substituent groups independently selected from halogen, $OJ_1$, $SJ_1$, $NJ_1J_2$, $N_3$, $COOJ_1$, CN, O—C(=O)$NJ_1J_2$, N(H)C(=NH)$NJ_1J_2$, N(H)C(=O)N(H)$J_2$ or N(H)C(=S)N(H)$J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, bicyclic nucleosides are provided having Formula II:

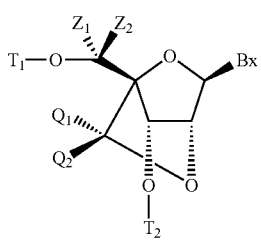

wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

one of $Z_1$ and $Z_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other one of $Z_1$ and $Z_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

one of $Q_1$ and $Q_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol and the other one of $Q_1$ and $Q_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol;

or $Q_1$ and $Q_2$ together are methylene (=$CH_2$);

each substituted group is mono or poly substituted with substituent groups independently selected from halogen, $OJ_1$, $SJ_1$, $NJ_1J_2$, $N_3$, $COOJ_1$, CN, O—C(=O)$NJ_1J_2$, N(H)C(=NH)$NJ_1J_2$, N(H)C(=O)N(H)$J_2$ or N(H)C(=S)N(H)$J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, one of $Z_1$ and $Z_2$ is H and one of $Q_1$ and $Q_2$ is H wherein the substituent groups that are not H (one of $Z_1$ and $Z_2$ and one of $Q_1$ and $Q_2$) each, independently, have a particular configuration thereby providing either (R) or (S) chirality. Such chirality is a design choice that can be determined during synthesis (see Examples 20 and 21).

In certain embodiments, oligomeric compounds are provided herein having at least one bicyclic nucleoside of Formula III:

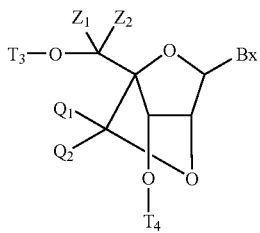

wherein independently for each bicyclic nucleoside having Formula III:

Bx is a heterocyclic base moiety;

$T_3$ and $T_4$ are each, independently, an internucleoside linking group linking the bicyclic nucleoside of Formula III to the oligomeric compound or one of $T_3$ and $T_4$ is an internucleoside linking group linking the bicyclic nucleoside of Formula III to the oligomeric compound and the other of $T_3$ and $T_4$ is H, a hydroxyl protecting group, a linked conjugate group or a 5' or 3'-terminal group;

one of $Z_1$ and $Z_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other one of $Z_1$ and $Z_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

one of $Q_1$ and $Q_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol and the other one of $Q_1$ and $Q_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol;

or $Q_1$ and $Q_2$ together are methylene (=$CH_2$);

each substituted group is mono or poly substituted with substituent groups independently selected from halogen, $OJ_1$, $SJ_1$, $NJ_1J_2$, $N_3$, $COOJ_1$, CN, O—C(=O)$NJ_1J_2$, N(H)C(=NH)$NJ_1J_2$, N(H)C(=O)N(H)$J_2$ or N(H)C(=S)N(H)$J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, oligomeric compounds are provided herein having Formula IV:

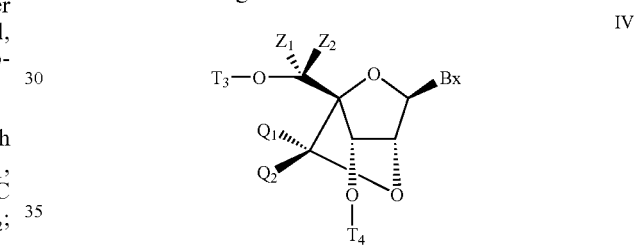

wherein independently for each bicyclic nucleoside having Formula IV:

Bx is a heterocyclic base moiety;

$T_3$ and $T_4$ are each, independently, an internucleoside linking group linking the bicyclic nucleoside of Formula IV to the oligomeric compound or one of $T_3$ and $T_4$ is an internucleoside linking group linking the bicyclic nucleoside of Formula IV to the oligomeric compound and the other of $T_3$ and $T_4$ is H, a hydroxyl protecting group, a linked conjugate group or a 5' or 3'-terminal group;

one of $Z_1$ and $Z_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other one of $Z_1$ and $Z_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

one of $Q_1$ and $Q_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol and the other one of $Q_1$ and $Q_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol;

or $Q_1$ and $Q_2$ together are methylene (=$CH_2$);

each substituted group is mono or poly substituted with substituent groups independently selected from halogen, $OJ_1$, $SJ_1$, $NJ_1J_2$, $N_3$, $COOJ_1$, CN, O—C(=O)$NJ_1J_2$, N(H)C(=NH)$NJ_1J_2$, N(H)C(=O)N(H)$J_2$ or N(H)C(=S)N(H)$J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, the bis-modified bicyclic nucleosides provided herein are useful for modifying otherwise unmodified oligomeric compounds at one or more positions. Such modified oligomeric compounds can be described as having a particular motif. Motifs amenable the oligomeric compounds incorporating at least one of the bis-modified bicyclic nucleosides provided herein include but are not limited to a gapped motif, a hemimer motif, a blockmer motif, a fully modified motif, a positionally modified motif and an alternating motif. In conjunction with these motifs a wide variety of linkages can also be used including but not limited to phosphodiester and phosphorothioate linkages used uniformly or in combinations. The positioning of 6-modified bicyclic nucleosides and the use of linkage strategies can be easily optimized for the best activity for a particular target.

Representative U.S. patents that teach the preparation of representative motifs include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety. Motifs are also disclosed in International Applications PCT/US2005/019219, filed Jun. 2, 2005 and published as WO 2005/121371 on Dec. 22, 2005 and PCT/US2005/019220, filed Jun. 2, 2005 and published as WO 2005/121372 on Dec. 22, 2005; each of which is incorporated by reference herein in its entirety.

The terms "stable compound" and "stable structure" are meant to indicate a Compound that is sufficiently robust to survive isolation to a useful degree of purity from a reaction mixture, and formulation into an efficacious therapeutic agent. Only stable Compounds are contemplated herein.

Selected substituent groups within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the Compound intended. Such properties include, by way of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The terms "substituent" and "substituent group," as used herein, are meant to include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound. Such groups include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxo (—O—$R_{aa}$), aryl, aralkyl, heterocyclic, heteroaryl, heteroarylalkyl, amino (—N$R_{bb}R_{cc}$), imino(=N$R_{bb}$), amido (—C(O)N$R_{bb}R_{cc}$ or —N($R_{bb}$)C(O)$R_{aa}$), azido (—$N_3$), nitro (—$NO_2$), cyano (—CN), carbamido (—OC(O)N$R_{bb}R_{cc}$ or —N($R_{bb}$)C(O)O$R_{aa}$), ureido (—N($R_{bb}$)C(O)N$R_{bb}R_{cc}$), thioureido (—N($R_{bb}$)C(S)N$R_{bb}R_{cc}$), guanidinyl (—N($R_{bb}$)C(=N$R_{bb}$)N$R_{bb}R_{cc}$), amidinyl (—C(=N$R_{bb}$)N$R_{bb}R_{cc}$ or —N($R_{bb}$)C(N$R_{bb}$)$R_{aa}$), thiol (—S$R_{bb}$), sulfinyl (—S(O)$R_{bb}$), sulfonyl (—S(O)$_2R_{bb}$), sulfonamidyl (—S(O)$_2$N$R_{bb}R_{cc}$ or —N($R_{bb}$)S(O)$_2R_{bb}$) and conjugate groups. Wherein each $R_{aa}$, $R_{bb}$ and $R_{cc}$ is H, an optionally linked chemical functional group or a further substituent group with a preferred list including without limitation H, alkyl, alkenyl, alkynyl, aliphatic, alkoxy, acyl, aryl, aralkyl, heteroaryl, alicyclic, heterocyclic and heteroarylalkyl.

In certain embodiments, linking groups or bifunctional linking moieties such as those known in the art may be useful in the bis-modified bicyclic nucleosides or oligomeric compounds provided herein. Linking groups are useful for attachment of chemical functional groups, conjugate groups, reporter groups and other groups to selective sites in a parent compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, oligomeric compounds are modified by covalent attachment of one or more 5' or 3'-terminal groups. The term "terminal group" as used herein is meant to include useful groups known to the art skilled that can be placed on one or both of the 3' and 5'-ends of an oligomeric compound for various purposes such as enabling the tracking of the oligomeric compound (a fluorescent label or other reporter group), improving the pharmacokinetics or pharmacodynamics of the oligomeric compound (a group for enhancing uptake and delivery) or enhancing one or more other desirable properties of the oligomeric compound (group for improving nuclease stability or binding affinity). In certain embodiments, 3' and 5'-terminal groups include without limitation, one or more modified or unmodified nucleosides, conjugate groups, capping groups, phosphate moieties and protecting groups.

The term "hydrocarbyl" includes groups comprising C, O and H. Included are straight, branched and cyclic groups having any degree of saturation. Such hydrocarbyl groups can include one or more heteroatoms selected from N, O and S and can be further mono or poly substituted with one or more substituent groups.

The term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substitutent groups.

The term "alkenyl," as used herein, refers to a straight or branched hydrocarbon chain radical containing up to twenty four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substitutent groups.

The term "alkynyl," as used herein, refers to a straight or branched hydrocarbon radical containing up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substitutent groups.

The term "aminoalkyl" as used herein, refers to an amino substituted alkyl radical. This term is meant to include $C_1$-$C_{12}$ alkyl groups having an amino substituent at any position and wherein the alkyl group attaches the aminoalkyl group to the parent molecule. The alkyl or amino portions of the aminoalkyl group can be further substituted with substituent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups, interrupted by heteroatoms include without limitation polyalkoxys, such as polyalkylene glycols, polyamines, and polyimines. Aliphatic groups as used herein may optionally include further substitutent groups.

The term "alicyclic" or "alicyclyl" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substitutent groups.

The term "alkoxy," as used herein, refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substitutent groups.

The terms "halo" and "halogen," as used herein, refer to an atom selected from fluorine, chlorine, bromine and iodine.

The terms "aryl" and "aromatic," as used herein, refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20 carbon atoms in one or more rings. Aryl groups as used herein may optionally include further substitutent groups.

The terms "aralkyl" and "arylalkyl," as used herein, refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substitutent groups attached to the alkyl, the aryl or both groups that form the radical group.

The term "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substitutent groups.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substitutent groups.

The term "heteroarylalkyl," as used herein, refers to a heteroaryl group as previously defined having an alkyl radical that can attach the heteroarylalkyl group to a parent molecule. Examples include, but are not limited to, pyridinylmethyl, pyrimidinylethyl, napthyridinylpropyl and the like. Heteroarylalkyl groups as used herein may optionally include further substitutent groups.

The term "mono or poly cyclic structure" as used herein includes all ring systems that are single or polycyclic having rings that are fused or linked and is meant to be inclusive of single and mixed ring systems individually selected from aliphatic, alicyclic, aryl, heteroaryl, aralkyl, arylalkyl, heterocyclic, heteroaryl, heteroaromatic, heteroarylalkyl. Such mono and poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. In another aspect, mono or poly cyclic structures can be attached to a parent molecule directly through a ring atom, through a substituent group or a bifunctional linking moiety.

The term "acyl," as used herein, refers to a radical formed by removal of a hydroxyl group from an organic acid and has the general formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups. The term "oxo" refers to the group (=O).

The compounds described herein can be prepared by any of the applicable techniques of organic synthesis, as, for example, illustrated in the examples below. Many such techniques are well known in the art. However, many of the known techniques are elaborated in *Compendium of Organic Synthetic Methods* (John Wiley & Sons, New York) Vol. 1, Ian T. Harrison and Shuyen Harrison (1971); Vol. 2, Ian T. Harrison and Shuyen Harrison (1974); Vol. 3, Louis S. Hegedus and Leroy Wade (1977); Vol. 4, Leroy G. Wade Jr., (1980); Vol. 5, Leroy G. Wade Jr. (1984); and Vol. 6, Michael B. Smith; as well as March, J., *Advanced Organic Chemistry*, 3rd Edition, John Wiley & Sons, New York (1985); *Comprehensive Organic Synthesis. Selectivity, Strategy & Efficiency in Modern Organic Chemistry, In 9 Volumes*, Barry M. Trost, Editor-in-Chief, Pergamon Press, New York (1993); *Advanced Organic Chemistry, Part B: Reactions and Synthesis*, 4th Ed.; Carey and Sundberg; Kluwer Academic/Plenum Publishers: New York (2001); *Advanced Organic Chemistry, Reactions, Mechanisms, and Structure*, 2nd Edition, March, McGraw Hill (1977); *Greene's Protective Groups in Organic Synthesis*, 4th Edition, Greene, T. W., and Wutz, P. G. M., John Wiley & Sons, New York (2007); and *Comprehensive Organic Transformations*, 2nd Edition, Larock, R. C., John Wiley & Sons, New York (1999).

In certain embodiments, oligomeric compounds provided herein are modified by covalent attachment of one or more conjugate groups. In general, conjugate groups modify one or more properties of the attached oligomeric compound including but not limited to pharmakodynamic, pharmacokinetic, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, drug groups such as ibuprofen, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

The term "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in *Greene's Protective Groups in Organic Synthesis*, 4th Edition, Greene, T. W., and Wutz, P. G. M., John Wiley & Sons, New York (2007).

Groups can be selectively incorporated into oligomeric compounds provided herein as precursors. For example an amino group can be placed into a compound as an azido group that can be chemically converted to the amino group at a desired point in the synthesis. Generally, groups are protected or present as a precursor that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, triisopropylsilyl, [(triisopropylsilyl)oxymethyl (TOM), monomethoxytrityl, dimethoxytrityl (DMT), trimethoxytrityl, 1 (2-fluorophenyl)-4-methoxypiperidin-4-yl (FPMP), 9-phenylxanthine-9-yl (Pixyl) and 9-(p-methoxyphenyl)xanthine-9-yl (MOX), triphenylmethyl (trityl), 4,4'-dimethoxytrityl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate. Where more preferred hydroxyl protecting groups include, but are not limited to, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include, but are not limited to, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include, but are not limited to, triphenylmethyl (trityl), benzyl (Bn), and the like.

In some preferred embodiments oligomeric compounds are prepared by connecting nucleosides with optionally protected phosphorus containing internucleoside linkages. Representative protecting groups for phosphorus containing internucleoside linkages such as phosphodiester and phosphorothioate linkages include β-cyanoethyl, diphenylsilylethyl, 6-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725, 677 and Re. 34,069 (β-cyanoethyl); Beaucage, S. L. and Iyer, R. P., Tetrahedron, 49 No. 10, pp. 1925-1963 (1993); Beaucage, S. L. and Iyer, R. P., Tetrahedron, 49 No. 46, pp. 10441-10488 (1993); Beaucage, S. L. and Iyer, R. P., Tetrahedron, 48 No. 12, pp. 2223-2311 (1992).

As used herein, the term "orthogonally protected" refers to functional groups which are protected with different classes of protecting groups, wherein each class of protecting group can be removed in any order and in the presence of all other classes (see, Barany, G. and Merrifield, R. B., *J. Am. Chem. Soc.*, 1977, 99, 7363; idem, 1980, 102, 3084.) Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired Compound or oligomeric Compound.

In certain embodiments, provided herein are compounds having reactive phosphorus groups useful for forming internucleoside linkages including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. A preferred synthetic solid phase synthesis utilizes phosphoramidites ($P^{III}$ chemistry) as reactive phosphites. The intermediate phosphite compounds are subsequently oxidized to the Pv state using known methods to yield, in preferred embodiments, phosphodiester or phosphorothioate internucleotide linkages. Additional reactive phosphates and phosphites are disclosed in Tetrahedron Report Number 309 (Beaucage and Iyer, *Tetrahedron*, 1992, 48, 2223-2311).

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, non-phosphorus containing internucleoside linking groups such as formacetyl and methyleneimino, and neutral non-ionic internucleoside linking groups such as amide-3 (3'-$CH_2$—C(=O)—N(H)-5'), amide-4 (3'-$CH_2$—N(H)—C(=O)-5').

Specific examples of oligomeric compounds useful herein include oligonucleotides containing modified e.g. non-naturally occurring internucleoside linkages. Two main classes of internucleoside linkages are defined by the presence or absence of a phosphorus atom. Modified internucleoside linkages having a phosphorus atom include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Modified internucleoside linkages not having a phosphorus atom include, but are not limited to, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

The compounds described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)- such as for amino acids et al. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

In certain embodiments, the term "oligomeric compound" refers to a polymer having at least a region that is capable of hybridizing to a nucleic acid molecule. The term "oligomeric compound" includes oligonucleotides, oligonucleotide analogs and oligonucleosides as well as nucleotide mimetics and/or mixed polymers comprising nucleic acid and non-nucleic acid components. Oligomeric compounds are routinely prepared linearly but can be joined or otherwise prepared to be circular and may also include branching. Oligomeric compounds can form double stranded constructs such as for example two strands hybridized to form double stranded compositions. The double stranded compositions can be linked or separate and can include overhangs on the ends. In general, an oligomeric compound comprises a backbone of linked monomeric subunits where each linked monomeric subunit is directly or indirectly attached to a heterocyclic base moiety. Oligomeric compounds may also include monomeric subunits that are not linked to a heterocyclic base moiety thereby providing abasic sites. The linkages joining the monomeric subunits, the sugar moieties or surrogates and the heterocyclic base moieties can be independently modified. The linkage-sugar unit, which may or may not include a heterocyclic base, may be substituted with a mimetic such as the monomers in peptide nucleic acids. The ability to modify or substitute portions or entire monomers at each position of an oligomeric compound gives rise to a large number of possible motifs.

In certain embodiments, the term "oligomeric compound" refers to a contiguous sequence of linked monomeric subunits. In general each linked monomeric subunits is directly or indirectly attached to a heterocyclic base moiety but abasic sites are also possible. At least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having a plurality of non-naturally occurring nucleoside mimetics and or nucleosides having sugar surrogate groups. When preparing oligomeric compounds having specific motifs as disclosed herein it can be advantageous to mix non-naturally occurring monomer subunits such as the bis-modified bicyclic nucleosides as provided herein with other non-naturally occurring monomer subunits, naturally occurring monomer subunits (nucleosides) or mixtures thereof. In certain embodiments, oligomeric compounds are provided herein comprising a contiguous sequence of linked monomeric subunits wherein at least one monomeric subunit is a bis-modified bicyclic nucleoside as provided herein. In certain embodiments, oligomeric compounds are provided comprising a plurality of bis-modified bicyclic nucleosides as provided herein.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond however, open linear structures are generally desired. Within the oligonucleotide structure, the phosphate groups are commonly referred to as forming the internucleoside linkages of the oligonucleotide. The normal internucleoside linkage of RNA and DNA is a 3' to 5' phosphodiester linkage.

In certain embodiments, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more non-naturally occurring portions. Such non-naturally occurring oligonucleotides are often desired over naturally occurring forms because of desirable properties such as, for example, enhanced cellular uptake, enhanced affinity for nucleic acid target and increased stability in the presence of nucleases.

In certain embodiments, the term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include, but are not limited to, siloxane, sulfide, sulfoxide, sulfone, acetyl, formacetyl, thioformacetyl, methylene formacetyl, thioformacetyl, alkenyl, sulfamate; methyleneimino, methylenehydrazino, sulfonate, sulfonamide, amide and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

The term "nucleobase" or "heterocyclic base moiety" as used herein, is intended to by synonymous with "nucleic acid base or mimetic thereof." In general, a nucleobase is any substructure that contains one or more atoms or groups of atoms capable of hydrogen bonding to a base of a nucleic acid. The term heterocyclic base moiety includes, purines, pyrimidines, heterocyclic bases, modified bases, modified nucleobases and natural and non-naturally occurring nucleobases.

As used herein, "unmodified" or "natural" nucleobases include the purine bases adenine (A) and guanine (G), and the pyrimidine bases thymine (T), cytosine (C) and uracil (U). Modified nucleobases include, but are not limited to other synthetic and natural nucleobases such as for example 5-methylcytosine (5-me-C), 5-hydroxymethyl cytosine, xanthine, hypoxanthine and 2-aminoadenine. Modified nucleobases may also include those in which the purine or pyrimidine base is replaced with other heterocycles, for example 7-deazaadenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al, *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993.

Modified nucleobases include, but are not limited to, universal bases, hydrophobic bases, promiscuous bases, size-expanded bases, and fluorinated bases as defined herein. Certain of these nucleobases are particularly useful for increasing the binding affinity of the oligomeric compounds provided herein. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-

278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

In addition to having at least one bis-modified bicyclic nucleoside, oligomeric compounds provided herein may also contain one or more additional nucleosides having modified sugar moieties. The furanosyl sugar ring can be modified in a number of ways including substitution with a substituent group, bridging to form a BNA and substitution of the 4'-O with a heteroatom such as S or N(R). Some representative U.S. patents that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920, 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety. A representative list of preferred modified sugars includes but is not limited to substituted sugars having a 2'-F, 2'-OCH$_2$ or a 2'-O(CH$_2$)$_2$—OCH$_3$ substituent group; 4'-thio modified sugars and bicyclic modified sugars.

In certain embodiments, the oligomeric compounds provided herein may also contain one or more nucleosides having modified sugar moieties. The furanosyl sugar ring can be modified in a number of ways including substitution with a substituent group, bridging to form a BNA and substitution of the 4'-O with a heteroatom such as S or N(R). Some representative U.S. patents that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety. A representative list of preferred modified sugars includes but is not limited to substituted sugars having a 2'-F, 2'-OCH$_2$ or a 2'-O(CH$_2$)$_2$—OCH$_3$ substituent group; 4'-thio modified sugars and bicyclic modified sugars.

As used herein the term "nucleoside mimetic" is intended to include those structures used to replace the sugar or the sugar and the base not the linkage at one or more positions of an oligomeric compound such as for example nucleoside mimetics having morpholino or bicyclo[3.1.0]hexyl sugar mimetics e.g. non furanose sugar units with a phosphodiester linkage. The term "sugar surrogate" overlaps with the slightly broader term "nucleoside mimetic" but is intended to indicate replacement of the sugar unit (furanose ring) only. The term "nucleotide mimetic" is intended to include those structures used to replace the nucleoside and the linkage at one or more positions of an oligomeric compound such as for example peptide nucleic acids or morpholinos (morpholinos linked by —N(H)—C(=O)—O— or other non-phosphodiester linkage.

In certain embodiments, oligomeric compounds provided herein can comprise from about 8 to about 80 nucleosides and/or modified nucleosides or mimetics in length. One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleosides and/or modified nucleosides or mimetics in length, or any range therewithin.

In certain embodiments, the oligomeric compounds of the invention are 8 to 40 nucleosides and/or modified nucleosides or mimetics in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleosides and/or modified nucleosides or mimetics in length, or any range therewithin.

In certain embodiments, the oligomeric compounds provided herein are 8 to 20 nucleosides and/or modified nucleosides or mimetics in length. One having ordinary skill in the art will appreciate that this embodies oligomeric compounds of 8, 9, 10, 11, 12, 13, 14, 15, 16, 17, 18, 19 or 20 nucleosides and/or modified nucleosides or mimetics in length, or any range therewithin.

In certain embodiments, the oligomeric compounds provided herein are 10 to 16 nucleosides and/or modified nucleosides or mimetics in length. One having ordinary skill in the art will appreciate that this embodies oligomeric compounds of 10, 11, 12, 13, 14, 15 or 16 nucleosides and/or modified nucleosides or mimetics in length, or any range therewithin.

In certain embodiments, the oligomeric compounds provided herein are 10 to 14 nucleosides and/or modified nucleosides or mimetics in length. One having ordinary skill in the art will appreciate that this embodies oligomeric compounds of 10, 11, 12, 13 or 14 nucleosides and/or modified nucleosides or mimetics in length, or any range therewithin.

In certain embodiments, oligomeric compounds provided herein comprise from about 12 to 16 monomer subunits in length. One having ordinary skill in the art will appreciate that this embodies oligomeric compounds of 12, 13, 14, 15 or 16 monomer subunits in length, or any range therewithin.

In certain embodiments, oligomeric compounds of any of a variety of ranges of lengths of linked monomer subunits are provided. In certain embodiments, oligomeric compounds are provided consisting of X-Y linked monomer subunits, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-29, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked monomer subunits.

In certain embodiments, ranges for the length of the oligomeric compounds provided herein are 8-16, 8-40, 10-12, 10-14, 10-16, 10-18, 10-20, 10-21, 12-14, 12-16, 12-18, 12-20 and 12-24 linked monomer subunits.

In certain embodiments, the ranges for the oligomeric compounds listed herein are meant to limit the number of monomer subunits in the oligomeric compounds, however such oligomeric compounds may further include protecting groups such as hydroxyl protecting groups, optionally linked conjugate groups, 5' and/or 3'-terminal groups and/or other substituents.

In certain embodiments, the oligomerization of modified and unmodified nucleosides and mimetics thereof is performed according to literature procedures for DNA (Protocols for Oligonucleotides and Analogs, Ed. Agrawal (1993), Humana Press) and/or RNA (Scaringe, Methods (2001), 23, 206-217; Gait et al., Applications of Chemically synthesized RNA in RNA:Protein Interactions, Ed. Smith (1998), 1-36; Gallo et al., *Tetrahedron* (2001), 57, 5707-5713) synthesis as appropriate. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

Commercially available equipment routinely used for the support medium based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), Oligonucleotides and Analogues, a Practical Approach, Oxford University Press, New York (1991).

The synthesis of RNA and related analogs relative to the synthesis of DNA and related analogs has been increasing as efforts in RNAi increase. The primary RNA synthesis strategies that are presently being used commercially include 5'-O-DMT-2'-O-t-butyldimethylsilyl (TBDMS), 5'-O-DMT-2'-O-[1 (2-fluorophenyl)-4-methoxypiperidin-4-yl] (FPMP), 2'-O-[(triisopropylsilyl)oxy]methyl (2'-O—CH$_2$—O—Si (iPr)$_3$ (TOM), and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. Such an activator would also be amenable herein.

The primary groups being used for commercial RNA synthesis are:

TBDMS=5'-O-DMT-2'-O-t-butyldimethylsilyl;
TOM=2'-O-[(triisopropylsilyl)oxy]methyl;
DOD/ACE=(5'-O-bis(trimethylsiloxy)cyclododecyloxysilyl ether-2'-O-bis(2-acetoxyethoxy)methyl
FPMP=5'-O-DMT-2'-O-[1(2-fluorophenyl)-4-methoxypiperidin-4-yl].

All of the aforementioned RNA synthesis strategies are amenable herein. Strategies that would be a hybrid of the above e.g. using a 5'-protecting group from one strategy with a 2'-O-protecting from another strategy is also amenable herein.

In certain embodiments, "hybridization" means the pairing of complementary strands of oligomeric compounds. In certain embodiments, one mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound is specifically hybridizable when binding of the compound to the target nucleic acid interferes with the normal function of the target nucleic acid to cause a loss of activity, and there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

"Complementary," as used herein, refers to the capacity for precise pairing of two nucleobases regardless of where the two are located. For example, if a nucleobase at a certain position of an oligomeric compound is capable of hydrogen bonding with a nucleobase at a certain position of a target nucleic acid, the target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). The oligomeric compounds provided herein can comprise at least about 70%, at least about 80%, at least about 90%, at least about 95%, or at least about 99% sequence complementarity to a target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present disclosure. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Further included herein are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds provided herein may elicit the action of one or more enzymes or structural proteins to effect modification of the target nucleic acid.

In certain embodiments, single stranded oligomers are provided that hybridize to a nucleic acid target and degrade the target by recruitment of an endonuclease enzyme. One non-limiting example of such an enzyme is RNAse H, a cellular endonuclease which cleaves the RNA strand of an RNA:DNA duplex. It is known in the art that single-stranded oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed in further investigative studies of the function of the peptide, or for use as a research, diagnostic, or therapeutic agent in accordance with the present disclosure.

In certain embodiments, suitable target segments may also be combined with their respective complementary antisense oligomeric compounds to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature*, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., *Genes Dev.* 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The oligomeric compounds provided herein can also be applied in the areas of drug discovery and target validation. In certain embodiments, the use of the oligomeric compounds and targets identified herein in drug discovery efforts to elucidate relationships that exist between proteins and a disease state, phenotype, or condition are provided. These methods include detecting or modulating a target peptide comprising contacting a sample, tissue, cell, or organism with the oligomeric compounds provided herein, measuring the nucleic acid or protein level of the target and/or a related phenotypic or chemical endpoint at some time after treatment, and optionally comparing the measured value to a non-treated sample or sample treated with a further oligomeric compound provided herein. These methods can also be performed in parallel or in combination with other experiments to determine the function of unknown genes for the process of target validation or to determine the validity of a particular gene product as a target for treatment or prevention of a particular disease, condition, or phenotype.

Effect of nucleoside modifications on RNAi activity is evaluated according to existing literature (Elbashir et al., Nature (2001), 411, 494-498; Nishikura et al., Cell (2001), 107, 415-416; and Bass et al., Cell (2000), 101, 235-238.)

The oligomeric compounds provided herein can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. The oligomeric compounds provided herein, either alone or in combination with other oligomeric compounds or therapeutics, can be used as tools in differential and/or combinatorial analyses to elucidate expression patterns of a portion or the entire complement of genes expressed within cells and tissues. Oligomeric compounds can also be effectively used as primers and probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of the antisense oligonucleotides, particularly the primers and probes, with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

As one nonlimiting example, expression patterns within cells or tissues treated with one or more oligomeric compounds are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., *Electrophoresis,* 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (To, Comb. Chem. High Throughput Screen, 2000, 3, 235-41).

While in certain embodiments, the bis-modified bicyclic nucleosides and oligomeric compounds that can be prepared therefrom provided herein can be utilized as described, the following examples serve only to illustrate and are not intended to be limiting.

EXAMPLE 1

Preparation of (1R,3R,4R,7S)-7-[2-cyanoethoxy (diisopropylamino)phosphinoxy]-1-[1-(S)-(4,4'-dimethoxytrityl)oxy-ethyl]-3-(uracil-1-yl)-2,5-dioxa-bicyclo[2.2.1]heptane (19a)

Scheme 1

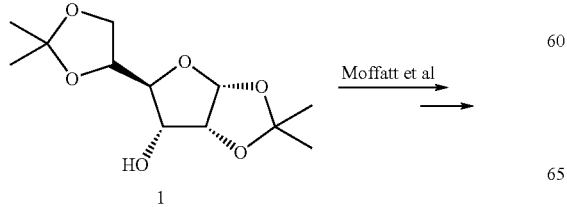

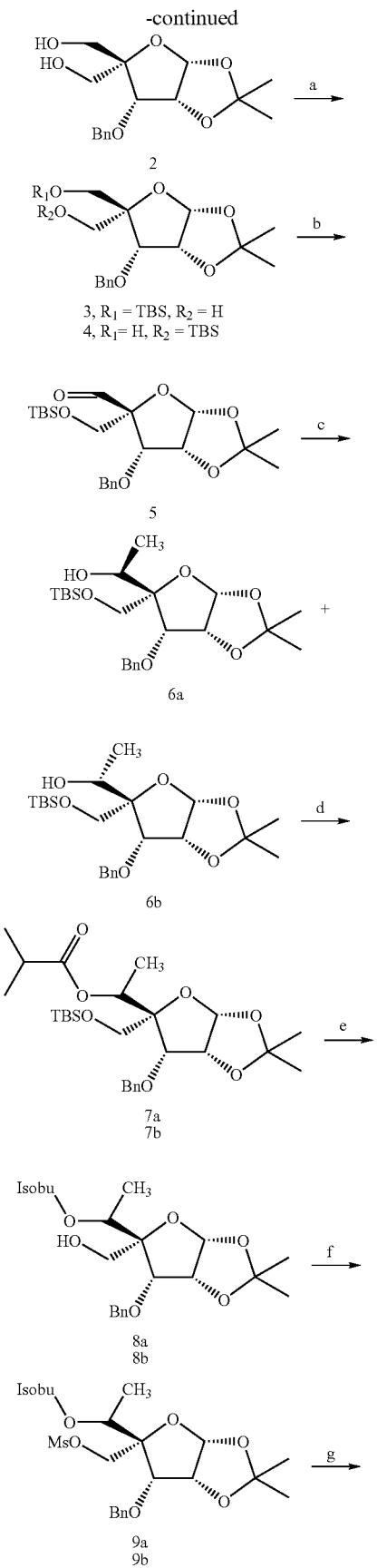

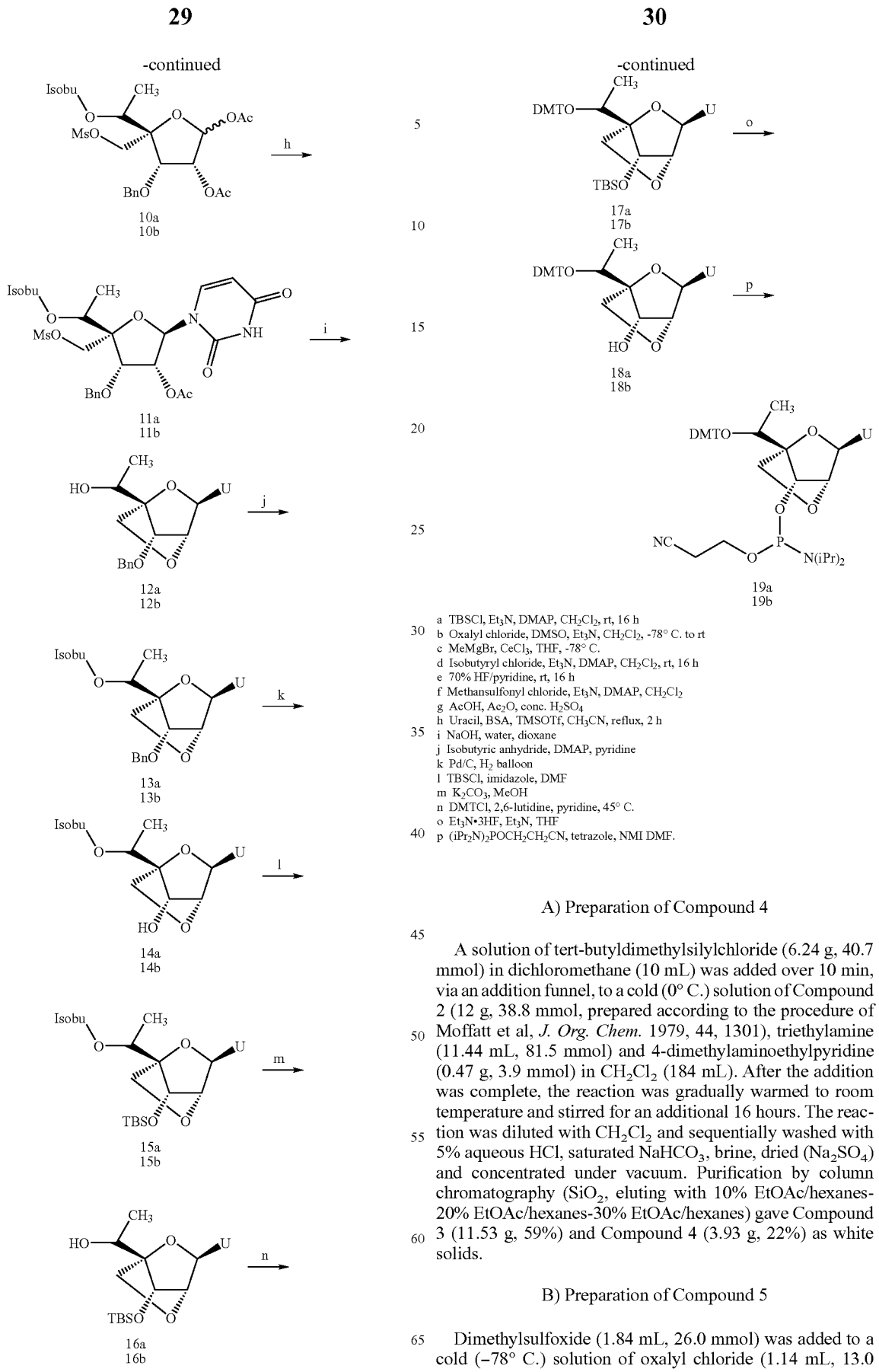

a TBSCl, Et₃N, DMAP, CH₂Cl₂, rt, 16 h
b Oxalyl chloride, DMSO, Et₃N, CH₂Cl₂, -78° C. to rt
c MeMgBr, CeCl₃, THF, -78° C.
d Isobutyryl chloride, Et₃N, DMAP, CH₂Cl₂, rt, 16 h
e 70% HF/pyridine, rt, 16 h
f Methansulfonyl chloride, Et₃N, DMAP, CH₂Cl₂
g AcOH, Ac₂O, conc. H₂SO₄
h Uracil, BSA, TMSOTf, CH₃CN, reflux, 2 h
i NaOH, water, dioxane
j Isobutyric anhydride, DMAP, pyridine
k Pd/C, H₂ balloon
l TBSCl, imidazole, DMF
m K₂CO₃, MeOH
n DMTCl, 2,6-lutidine, pyridine, 45° C.
o Et₃N•3HF, Et₃N, THF
p (iPr₂N)₂POCH₂CH₂CN, tetrazole, NMI DMF.

A) Preparation of Compound 4

A solution of tert-butyldimethylsilylchloride (6.24 g, 40.7 mmol) in dichloromethane (10 mL) was added over 10 min, via an addition funnel, to a cold (0° C.) solution of Compound 2 (12 g, 38.8 mmol, prepared according to the procedure of Moffatt et al, *J. Org. Chem.* 1979, 44, 1301), triethylamine (11.44 mL, 81.5 mmol) and 4-dimethylaminoethylpyridine (0.47 g, 3.9 mmol) in CH₂Cl₂ (184 mL). After the addition was complete, the reaction was gradually warmed to room temperature and stirred for an additional 16 hours. The reaction was diluted with CH₂Cl₂ and sequentially washed with 5% aqueous HCl, saturated NaHCO₃, brine, dried (Na₂SO₄) and concentrated under vacuum. Purification by column chromatography (SiO₂, eluting with 10% EtOAc/hexanes-20% EtOAc/hexanes-30% EtOAc/hexanes) gave Compound 3 (11.53 g, 59%) and Compound 4 (3.93 g, 22%) as white solids.

B) Preparation of Compound 5

Dimethylsulfoxide (1.84 mL, 26.0 mmol) was added to a cold (−78° C.) solution of oxalyl chloride (1.14 mL, 13.0 mmol) in CH₂Cl₂ (70 mL). The solution was stirred at −78° C.

for 30 minutes and a solution of Compound 4 (3.93 g, 9.3 mmol) in $CH_2Cl_2$ (20 mL) was added via a cannula. The stirring was continued for 45 minutes and triethylamine (5.48 mL, 39.0 mmol) was added to the reaction. The reaction was stirred for an additional 40 minutes after which it was poured into $CH_2Cl_2$ and the organic layer was sequentially washed with 5% aqueous HCl, saturated $NaHCO_3$, brine, dried ($Na_2SO_4$) and concentrated under vacuum to provide Compound 5, which was used without purification in the next step.

C) Preparation of Compound 6a and Compound 6b

A suspension of cerium III chloride (4.57 g, 18.6 mmol) in THF (55 mL) was stirred at room temperature for 90 minutes. The reaction was cooled in an ice bath and methyl magnesium bromide (13.3 mL of a 1M solution in THF) was added over 5 minutes and the stirring continued for another 90 minutes. A solution of crude Compound 5 (from above) in THF (15 mL) was added to the reaction. After stirring for another 90 minutes, the reaction was quenched with sat $NH_4Cl$ solution and poured into EtOAc. The organic layer was sequentially washed with 5% aqueous HCl, saturated $NaHCO_3$, brine, dried ($Na_2SO_4$) and concentrated under vacuum. Purification by column chromatography ($SiO_2$, eluting sequentially with $CHCl_3$; 3% acetone/$CHCl_3$; and finally 5% acetone/$CHCl_3$) gave Compound 6a (2.25 g, 55% from Compound 4) and Compound 6b (1.84 g, 45% from Compound 4).

6a $^1$H NMR (300 MHz, $CDCl_3$) δ: 7.44-7.29 (m, 5H), 5.68 (d, 1H, J=3.8), 4.76 (d, 1H, J=12.0), 4.62 (d, 1H, J=12.0), 4.58 (m, 1H), 4.44 (d, 1H, J=10.3), 4.08 (d, 1H, J=5.3), 3.95 (m, 1H), 3.81 (d, 1H, J=10.3), 2.84 (d, 1H, J=7.5), 1.60 (s, 3H), 1.30 (s, 3H), 1.20 (d, 3H, J=6.4), 0.88 (s, 9H), 0.08 (s, 3H), 0.05 (s, 3H).

6b $^1$H NMR (300 MHz, $CDCl_3$) δ: 7.39-2.29 (m, 5H), 5.73 (d, 1H, J=3.9), 4.76 (d, 1H, J=11.7), 4.58 (m, 1H, partially overlapped), 4.56 (d, 1H, J=11.7), 4.16 (d, 1H, J=5.2), 4.14-4.04 (m, 3H), 2.43 (d, 1H, J=3.8), 1.62 (s, 3H), 1.32 (s, 3H), 1.17 (d, 3H, J=6.52), 0.88 (s, 9H), 0.08 (s, 3H), 0.05 (s, 3H).

D) Preparation of Compound 7a

Isobutyryl chloride (0.67 mL, 6.3 mmol) was added to a cold (0° C.) solution of Compound 6a (2.29 g, 5.3 mmol), triethylamine (1.06 mL, 7.6 mmol) and 4-dimethylaminopyridine (77 mg, 0.6 mmol) in $CH_2Cl_2$ (6 mL). After stirring at room temperature for 16 hours, the reaction was poured into EtOAc and the organic layer was sequentially washed with 5% aqueous HCl, saturated $NaHCO_3$, brine, dried ($Na_2SO_4$) and concentrated under vacuum to provide Compound 7a, which was used without purification in the next step.

E) Preparation of Compound 8a

70% HF/pyridine (1.25 mL) was added to a solution of crude Compound 7a in THF (25 mL) in a polypropylene tube. After stirring at room temperature for 16 hours, triethylamine (1.25 mL) was added to the reaction. After 10 minutes, the reaction was poured into EtOAc and extracted with water, brine, dried ($Na_2SO_4$) and filtered. Additional triethylamine (1.25 mL) was added to the EtOAc solution and the reaction was concentrated under vacuum to provide Compound 8a, which was used without further purification in the next step.

F) Preparation of Compound 9a

Methanesulfonyl chloride (0.46 mL, 5.8 mmol) was added to a cold (0° C.) solution of crude Compound 8a, triethylamine (1.1 mL, 7.8 mmol) and 4-dimethylaminopyridine (60 mg, 0.5 mmol) in $CH_2Cl_2$ (21 mL). After stirring at room temperature for 1 hour, the reaction was poured into $CHCl_3$ and the organic layer was sequentially washed with 5% aqueous HCl, saturated $NaHCO_3$, brine, dried ($Na_2SO_4$) and concentrated under vacuum to give Compound 9a, which was used without purification in the next step.

G) Preparation of Compound 10a

Concentrated $H_2SO_4$ (1 drop) was added to a solution of crude Compound 9a in glacial acetic acid (9 mL) and acetic anhydride (1.3 mL). After stirring at room temperature for 1 hour, the reaction was poured into EtOAc and the organic layer was washed with water, saturated $NaHCO_3$, brine, dried ($Na_2SO_4$) and concentrated under vacuum. Purification by column chromatography ($SiO_2$, eluting with 40% EtOAc/hexanes) gave Compound 10 a (2.71 g, 99% from Compound 6a) as a colorless oil.

H) Preparation of Compound 11a

N,O-Bis(trimethylsilyl)acetamide (3.9 mL, 15.7 mmol) was added to a suspension of Compound 10a (2.7 g, 5.2 mmol) and uracil (0.73 g, 6.5 mmol) in MeCN (16 mL). After heating at 40° C. for 15 minutes to get a clear solution, trimethylsilyl triflate (1.23 mL, 6.8 mmol) was added to the reaction. After refluxing for 2 hours, the reaction was cooled to room temperature and poured into EtOAc. The organic layer was washed with saturated $NaHCO_3$, brine, dried ($Na_2SO_4$) and concentrated under vacuum to give Compound 11a, which was used without purification in the next step.

I) Preparation of Compound 12a

A solution of NaOH (2M, 11 mL) was added to a solution of crude Compound 11a in 1,4-dioxane:$H_2O$ (1:1, 12 mL). After stirring at room temperature for 16 hours, the reaction was neutralized with 5% aqueous HCl (pH ~7) and extracted with a mixture of 25% pyridine/EtOAc. The organic layer was further washed with 50% brine, brine, dried ($Na_2SO_4$) and concentrated under vacuum. Purification by column chromatography ($SiO_2$, 5% MeOH/$CHCl_3$) gave Compound 12a as a white solid (1.56 g, 83% from Compound 10a). $^1$H NMR (300 MHz, $CDCl_3$) δ: 8.48 (s, br, 1H), 7.71 (d, 1H, J=8.2), 7.40-7.29 (m, 5H), 5.71 (d, 1H, J=8.3), 5.67 (s, 1H), 4.67 (d, 2H, J=11.5), 4.54 (d, 1H, J=11.5), 4.48 (s, 1H), 4.19 (m, 1H), 4.03 (s, 1H, J=7.8), 3.91 (s, 1H), 3.76 (d, 1H, J=7.8), 1.32 (d, 3H, J=6.6).

J) Preparation of Compound 13a

Isobutyric anhydride (0.86 mL, 5.2 mmol) was added to a cold solution (0° C.) of Compound 12a (1.56 g, 4.3 mmol) and 4-dimethylaminopyridine (10 mg) in pyridine (8.6 mL). The reaction was stirred for 16 hours during which it gradually warmed to room temperature. The reaction was poured into EtOAc and extracted with brine, dried ($Na_2SO_4$) and concentrated under vacuum. Purification by column chromatography ($SiO_2$, 50% EtOAc/hexanes) gave Compound 13a (1.68 g, 90%) as a white solid.

K) Preparation of Compound 14a

MeOH (20 mL) was carefully added to a mixture of Pd/C (10% w/w, 190 mg) and Compound 13a (1.68 g, 3.9 mmol). The above mixture was hydrogenated using a $H_2$ balloon for 16 hours. The catalyst was removed by filtration through celite and concentrated to provide a crude mixture of Compounds 13a and 14a. The above procedure was repeated until Compound 13a could not be detected (TLC) in the reaction mixture. Purification by column chromatography (SiO$_2$, 7% MeOH/CHCl$_3$) gave Compound 14a as a white solid (1.35 g, 92%).

L) Preparation of Compound 15a tert-Butyldimethylsilyl chloride (1.95 g, 13.0 mmol) was added to a solution of Compound 14a (1.35 g, 4 mmol) and imidazole (1.76 g, 25.9 mmol) in DMF (8 mL). After stirring at room temperature for 16 hours, the reaction was poured into EtOAc and extracted with brine, dried (Na$_2$SO$_4$) and concentrated under vacuum. Purification by column chromatography (5% MeOH/CHCl$_3$) gave Compound 15a as a white solid (1.63 g, 90%).

M) Preparation of Compound 16a

K$_2$CO$_3$ (0.99 g, 7.1 mmol) was added to a solution of Compound 16a in MeOH (20 mL). After stirring at room temperature for 16 hours, the reaction was concentrated and purified by column chromatography (SiO$_2$, 10% MeOH/CHCl$_3$) to give Compound 16a as a white solid (1.15 g, 75%).

N) Preparation of Compound 17a 4,4'-Dimethoxytrityl chloride (DMTCl) (2.53 g, 7.5 mmol) was added to a solution of Compound 16a (1.15 g, 3.0 mmol) and 2,6-lutidine (0.87 mL, 7.5 mmol) in pyridine (20 mL). The reaction was heated at 45° C. for 24 hours after which additional DMTCl (0.43 g, 1.3 mmol) and 2,6-lutidine (0.15 mL, 1.27 g) was added. After heating at 45° C. for an additional 24 hours, the reaction was poured into EtOAc and extracted with brine, dried (Na$_2$SO$_4$) and concentrated. Purification by column chromatography (SiO$_2$, 25% EtOAc/hexanes-50% EtOAc/hexanes) gave Compound 17a as a yellowish foam (2.0 g, 97%). 17a $^1$H NMR (300 MHz, CDCl$_3$) δ: 8.75 (s, br, 1H), 8.09 (d, 1H, J=8.2), 7.49-7.19 (m, 9H), 6.82 (m, 4H), 5.68 (s, 1H), 5.66 (d, 1H, J=8.2, partially overlapped), 4.33 (s, 1H), 4.24 (s, 1H), 3.86 (d, 1H, J=7.6), 3.80 (s, 6H), 3.72 (m, 2H), 0.96 (d, 3H, J=6.5), 0.77 (s, 9H), 0.03 (s, 3H), −0.10 (s, 3H).

N) Preparation of Compound 18a

Triethylamine trihydrofluoride (1.29 mL, 8.0 mmol) was added to a solution of Compound 17a (1.09 g, 1.6 mmol) and triethylamine (0.45 mL, 3.2 mmol) in THF (8 mL) in a polypropylene tube. After stirring at room temperature for 48 hours, the reaction was poured into EtOAc and the organic phase was sequentially washed with H$_2$O, saturated NaHCO$_3$, brine, dried (Na$_2$SO$_4$) and concentrated under vacuum. Purification by column chromatography (SiO$_2$, eluting with 25% acetone/CHCl$_3$-40% acetone/CHCl$_3$) gave Compound 18a (0.79 g, 86%) as a white foam.

O) Preparation of (1R,3R,4R,7S)-7-[2-cyanoethoxy (diisopropylaminophosphinoxy]-1-[1-(S)-(4,4'-dimethoxytrityl)oxy-ethyl]-3-(uracil-1-yl)-2,5-dioxabicyclo[2.2.1]heptane, Compound 19a 2-cyanoethyl N,N'-tetraisopropylphosphoramidite (0.43 mL, 2.0 mmol) was added to a solution of Compound 18a (0.78 g, 1.4 mmol), tetrazole (76.0 mg, 1.1 mmol), N-methylimidazole (28 µL, 0.3 mmol) in DMF (7 mL). After stirring for 8 hours at room temperature, the reaction was poured into EtOAc and the organic phase was washed with 90% brine, brine, dried (Na$_2$SO$_4$) and concentrated under vacuum. Purification by column chromatography (SiO2, eluting with 60% EtOAc/hexanes-75% EtOAc/hexanes) gave Compound 19a (0.91 g, 87%) as a white solid. 19a 31p NMR (300 MHz, CDCl$_3$) δ: 149.1, 148.5.

EXAMPLE 2

Preparation of (1R,3R,4R,7S)-7-[2-cyanoethoxy (diisopropylamino)phosphinoxy]-1-[1-(R)-(4,4'-dimethoxytrityl) oxyethyl]-3-(uracil-1-yl)-2,5-dioxabicyclo[2.2.1]heptane, Compound 19b (Scheme 1)

A) Preparation of Compound 7b

Isobutyryl chloride (0.55 mL, 5.2 mmol) was added to a cold (0° C.) solution of Compound 6b (1.90 g, 4.4 mmol), triethylamine (0.88 mL, 6.3 mmol) and 4-dimethylaminopyridine (53 mg, 0.4 mmol) in CH$_2$Cl$_2$ (5 mL). After stirring at room temperature for 16 hours, the reaction was poured into EtOAc and the organic layer was sequentially washed with 5% aqueous HCl, saturated NaHCO$_3$, brine, dried (Na$_2$SO$_4$) and concentrated under vacuum to give Compound 7b which was used without purification in the next step.

B) Preparation of Compound 8b

70% HF/pyridine (2.0 mL) was added to a solution of crude Compound 7b in THF (30 mL) in a polypropylene tube. After stirring at room temperature for 16 hours, triethylamine (2.0 mL) was added to the reaction. After 10 minutes, the reaction was poured into EtOAc and extracted with water, brine, dried (Na$_2$SO$_4$) and filtered. Additional triethylamine (2.0 mL) was added to the EtOAc solution and the reaction was concentrated under vacuum to provide Compound 8b, which was used without further purification in the next step.

C) Preparation of Compound 9b

Methanesulfonyl chloride (0.40 mL, 5.2 mmol) was added to a cold (0° C.) solution of crude Compound 8b, triethylamine (0.88 mL, 6.3 mmol) and 4-dimethylaminopyridine (53 mg, 0.4 mmol) in CH$_2$Cl$_2$ (16 mL). After stirring at room temperature for 1 hour, the reaction was poured into CHCl$_3$ and the organic layer was sequentially washed with 5% aqueous HCl, saturated NaHCO$_3$, brine, dried (Na$_2$SO$_4$) and concentrated under vacuum to give Compound 9b, which was used without purification in the next step.

D) Preparation of Compound 10b

Concentrated H$_2$SO$_4$ (1 drop) was added to a solution of crude Compound 9b in glacial acetic acid (9 mL) and acetic anhydride (1.3 mL). After stirring at room temperature for 1 hour, the reaction was poured into EtOAc and the organic layer was washed with water, saturated NaHCO$_3$, brine, dried (Na$_2$SO$_4$) and concentrated under vacuum. Purification by column chromatography (SiO$_2$, eluting with 40% EtOAc/hexanes) gave Compound 10b (2.0 g, 90% from 6b) as a colorless oil.

E) Preparation of Compound 11b

N,O-Bis(trimethylsilyl)acetamide (2.73 mL, 11.0 mmol) was added to a suspension of Compound 10b (2.0 g, 3.9 mmol) and uracil (0.52 g, 4.6 mmol) in CH$_3$CN (11 mL). After heating at 40° C. for 15 minutes to get a clear solution, trimethylsilyl triflate (0.87 mL, 4.8 mmol) was added to the reaction. After refluxing for 2 hours the reaction was cooled to room temperature and poured into EtOAc. The organic layer was washed with saturated NaHCO$_3$, brine, dried (Na$_2$SO$_4$) and concentrated under vacuum to give crude Compound 11b, which was used without purification in the next step.

F) Preparation of Compound 12b

A solution of NaOH (2M, 8.0 mL) was added to a solution of crude Compound 11b in 1,4-dioxane:H$_2$O (1:1, 8 mL). After stirring at room temperature for 16 hours, the reaction was neutralized with 5% aqueous HCl (pH ~7) and extracted with a mixture of 25% pyridine/EtOAc. The organic layer was further washed with 50% brine, brine, dried (Na$_2$SO$_4$) and concentrated under vacuum. Purification by column chromatography (SiO$_2$, 5% MeOH/CHCl$_3$) provided Compound 12b as a white solid (1.30 g, 98% from Compound 10b). 12b $^1$H NMR (300 MHz, CDCl$_3$) δ: 8.90 (s, br, 1H), 7.52 (d, 1H, J=8.2), 7.43-7.29 (m, 5H), 5.72 (d, 1H, J=8.2), 5.64 (s, 1H), 4.68 (d, 1H, J=11.5), 4.59 (s, 1H), 4.51 (d, 1H, J=11.5), 4.31 (m, 1H, partially overlapped), 4.24 (d, 1H, J=8.1), 3.96 (d, 1H, J=8.1), 3.79 (s, 1H), 2.25 (d, 1H, J=5.2), 1.34 (d, 3H, J=6.6).

G) Preparation of Compound 13b

Isobutyric anhydride (0.60 mL, 3.6 mmol) was added to a cold solution (0° C.) of Compound 12b (1.08 g, 3.0 mmol) and 4-dimethylaminopyridine (5 mg) in pyridine (6 mL). The reaction was stirred for 16 hours during which it gradually warmed to room temperature. The reaction was poured into EtOAc and extracted with brine, dried (Na$_2$SO$_4$) and concentrated under vacuum to give Compound 13b, which was used without further purification in the next step.

H) Preparation of Compound 14b

MeOH (20 mL) was carefully added to a mixture of Pd/C (10% w/w, 170 mg) and Compound 13b. The above mixture was hydrogenated using a H$_2$ balloon for 16 hours. The catalyst was removed by filtration through celite and concentrated to provide a crude mixture of Compounds 13b and 14b. The above procedure was repeated until Compound 13b could not be detected (TLC) in the reaction mixture. Purification by column chromatography (SiO$_2$, 7% MeOH/CHCl$_3$) gave Compound 14b as a white solid (0.84 g, 83% from Compound 12b).

I) Preparation of Compound 15b tert-Butyldimethylsilyl chloride (1.49 g, 9.9 mmol) was added to a solution of Compound 14b (0.84 g, 2.5 mmol) and imidazole (1.35 g, 19.9 mmol) in DMF (5 mL). After stirring at room temperature for 16 hours, the reaction was poured into EtOAc and extracted with brine, dried (Na$_2$SO$_4$) and concentrated under vacuum. Purification by column chromatography (5% MeOH/CHCl$_3$) gave Compound 15b as a white solid (0.92 g, 81%).

J) Preparation of Compound 16b

K$_2$CO$_3$ (0.70 g, 5.1 mmol) was added to a solution of Compound 15b in MeOH (10 mL). After stirring at room temperature for 16 hours, the reaction was concentrated and partitioned between 90% brine and 25% pyridine/EtOAc. The organic phase was collected, dried (Na$_2$SO$_4$) and concentrated under vacuum to give crude Compound 16b, which was used without further purification in the next step.

K) Preparation of Compound 17b 4,4'-Dimethoxytrityl chloride (DMTCl) (1.87 g, 5.5 mmol) was added to a solution of Compound 16b (0.71 g, 1.8 mmol) and 2,6-lutidine (0.64 mL, 5.5 mmol) in pyridine (20 mL). After heating at 45° C. for 48 hours, the reaction was poured into EtOAc and extracted with brine, dried (Na$_2$SO$_4$) and concentrated. Purification by column chromatography (SiO$_2$, 25% EtOAc/hexanes-50% EtOAc/hexanes) gave Compound 17b as a yellowish foam (1.29 g, 93% from Compound 15b). 17b $^1$H NMR (300 MHz, CDCl$_3$) δ: 8.70 (s, br, 1H), 7.61 (d, 1H, J=8.2), 7.49-7.16 (m, 9H), 6.82 (d, 4H, J=8.9), 5.63 (s, 1H), 5.56 (d, 1H, J=8.2), 4.25 (s, 1H), 3.97 (d, 1H, J=8.1), 3.85 (s, 1H), 3.79 (s, 6H), 3.70 (d, 1H, J=8.1), 3.58 (m, 1H), 1.12 (d, 3H, J=6.6), 0.79 (s, 9H), 0.01 (s, 3H), −0.01(3H)

L) Preparation of Compound 18b

Triethylamine trihydrofluoride (1.06 mL, 6.5 mmol) was added to a solution of Compound 17b (0.89 g, 1.3 mmol) and triethylamine (0.46 mL, 3.3 mmol) in THF (6.5 mL) in a polypropylene tube. After stirring at room temperature for 48 hours, the reaction was poured into EtOAc and the organic phase was sequentially washed with H$_2$O, saturated NaHCO$_3$, brine, dried (Na$_2$SO$_4$) and concentrated under vacuum. Purification by column chromatography (SiO$_2$, eluting with 30% acetone/CHCl$_3$-45% acetone/CHCl$_3$) gave Compound 18b (0.73 g, 98%) as a white foam.

M) Preparation of (1R,3R,4R,7S)-7-[2-cyanoethoxy (diisopropylamino)phosphinoxy]-1-[1-(R)-(4,4'-dimethoxytrityl)oxy-ethyl]-3-(uracil-1-yl)-2,5-dioxabicyclo[2.2.1]heptane, Compound 19b 2-Cyanoethyl N,N'-tetraisopropylphosphoramidite (0.60 mL, 1.9 mmol) was added to a solution of Compound 18b (0.73 g, 1.3 mmol), tetrazole (71 mg, 1.0 mmol), N-methylimidazole (26 µL, 0.3 mmol) in DMF (6 mL). After stirring for 8 hours at rt, the reaction was poured into EtOAc and the organic phase was washed with 90% brine, brine, dried (Na$_2$SO$_4$) and concentrated under vacuum. Purification by column chromatography (SiO$_2$, eluting with 10% acetone/CHCl$_3$-15% acetone/CHCl$_3$) gave Compound 19b (0.89 g, 91a %) as a white solid. 19b $^{31}$P NMR (300 MHz, CDCl$_3$) δ: 149.4, 148.6.

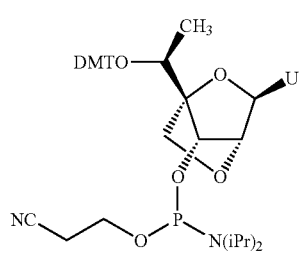

19a

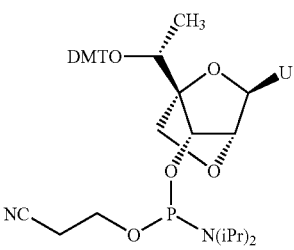

Compound 19a is prepared following the procedures illustrated for compound 19b using compounds 6a-18a in place of 6b-18b as illustrated in the schemes above.

EXAMPLE 3

Preparation of (1R,3R,4R,7S)-7-[2-cyanoethoxy (diisopropylamino)phosphinoxy]-1-[1-(S)-(4,4'-dimethoxytrityl)oxy-ethyl]-3-(4-N-benzoylcytosin-1-yl)-2,5-dioxa-bicyclo[2.2.1]heptane, Compound 24a

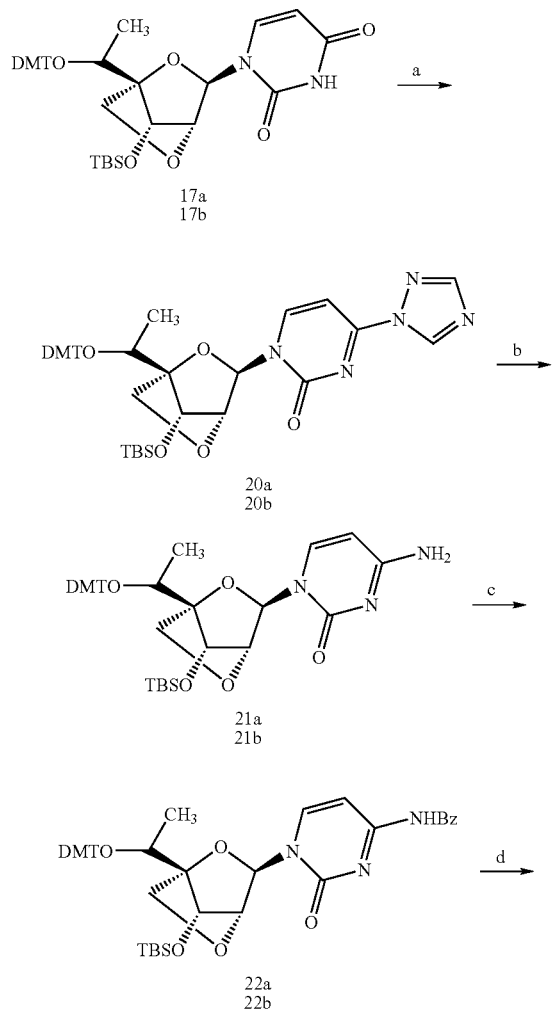

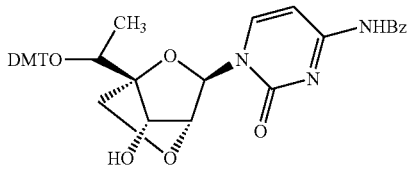

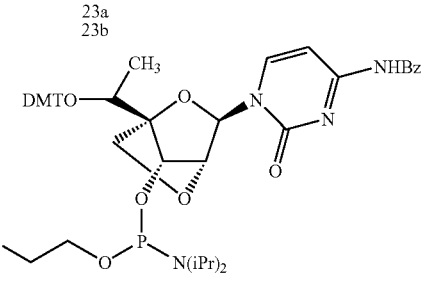

a 1,2,4-Triazole, POCl₃, Et₃N, CH₃CN
b Aq. NH₃, dioxane
c Benzoic anhydride, DMF
d Et₃N·3HF, Et₃N, THF
e (iPr₂N)₂POCH₂CH₂CN, NMI, tetrazole, DMF A) Preparation of Compound 20a Phosphorus oxychloride (0.98 mL, 10.5 mmol) was added dropwise to a cold (0° C.) suspension of 1,2,4-triazole (3.10 g, 44.9 mmol) in CH₃CN (17 mL). After stirring for 10 minutes, triethylamine (7.4 mL, 51.8 mmol) was added to the reaction and stirring was continued for 30 minutes. A solution of Compound 17a (0.91 g, 1.3 mmol) in CH₃CN (8 mL) was added to the reaction and the stirring was continued for 4 hours at room temperature. The reaction was poured into EtOAc and the organic layer was washed with H₂O, saturated NaHCO₃, brine, dried (Na₂SO₄) and concentrated to give crude Compound 20a, which was used without further purification in the next step.

B) Preparation of Compound 21a

Aqueous ammonia solution (4 mL) was added to a solution of Compound 20a in 1,4-dioxane (20 mL). After stirring for 16 hours at room temperature, the reaction was concentrated under vacuum. Purification by column chromatography (SiO₂, eluting with 5% MeOH/CHCl₃) gave Compound 21a (0.80 g, 89% from Compound 17a) as a white solid.

C) Preparation of Compound 22a

Benzoic anhydride (0.41 g, 1.8 mmol) was added to a solution of Compound 21a (0.80 g, 1.2 mmol) in N,N-dimethylformamide (3 mL). After stirring for 16 hours at room temperature, the reaction was concentrated under high vacuum. Purification by column chromatography (SiO₂, eluting with 50% EtOAc/hexanes) gave Compound 22a (0.81 g, 88%).

D) Preparation of Compound 23a

Triethylamine trihydroflouride (1.00 mL, 6.1 mmol) was added to a solution of Compound 22a (0.81 g, 1.1 mmol) and triethylamine (0.35 mL, 2.5 mmol) in THF (7 mL). After stirring at room temperature for 48 hours, the reaction was poured into EtOAc and the organic layer was washed with H$_2$O, saturated NaHCO$_3$, brine, dried (Na$_2$SO$_4$) and concentrated. Purification by column chromatography (SiO$_2$, eluting with 90% EtOAc/hexanes) gave Compound 23a (0.68 g, 99%).

E) Preparation of (1R,3R,4R,7S)-7-[2-cyanoethoxy (diisopropylamino)phosphinoxy]-1-[1-(S)-(4,4'-dimethoxytrityl)oxy-ethyl]-3-(4-N-Benzoylcytosin-1-yl)-2,5-dioxa-bicyclo[2.2.1]heptane, Compound 24a 2-cyanoethyl N,N'-tetraisopropylphosphoramidite (0.48 mL, 1.5 mmol) was added to a solution of Compound 23a (0.68 g, 1.0 mmol), tetrazole (56 mg, 0.81 mmol), N-methylimidazole (20 µL, 0.3 mmol) in DMF (5 mL). After stirring for 8 hours at room temperature, the reaction was poured into EtOAc and the organic phase was washed with 90% brine, brine, dried (Na$_2$SO$_4$) and concentrated under vacuum. Purification by column chromatography (SiO$_2$, eluting with 60% EtOAc/hexanes—90% EtOAc/hexanes) gave Compound 24a (0.73 g, 84%) as a white solid. 24a $^{31}$P NMR (300 MHz, CDCl$_3$) δ: 149.4, 148.6.

EXAMPLE 4

Preparation of (1R,3R,4R,7S)-7-[2-cyanoethoxy (diisopropylamino)phosphinoxy]-1-[1-(R)-(4,4'-dimethoxytrityl)oxy-ethyl]-3-(4-N-benzoylcytosin-1-yl)-2,5-dioxa-bicyclo[2.2.1]heptane, Compound 24b (Scheme 2)

A) Preparation of Compound 20b

Phosphorus oxychloride (1.3 mL, 14.0 mmol) was added dropwise to a cold (0° C.) suspension of 1,2,4-triazole (4.10 g, 59.5 mmol) in CH$_3$CN (30 mL). After stirring for 10 minutes, triethylamine (9.80 mL, 70.0 mmol) was added to the reaction and stirring was continued for 30 minutes. A solution of the Compound 17b (1.20 g, 1.8 mmol) in CH$_3$CN (10 mL) was added to the reaction and the stirring was continued for 4 hours at room temperature. The reaction was poured into EtOAc and the organic layer was washed with H$_2$O, saturated NaHCO$_3$, brine, dried (Na$_2$SO$_4$) and concentrated to give crude Compound 20b, which was used without further purification in the next step.

B) Preparation of Compound 21b

Aqueous ammonia solution (5 mL) was added to a solution of triazolide 20b (from above) in 1,4-dioxane (25 mL). After stirring for 16 hours at room temperature, the reaction was concentrated to provide Compound 21b which was dried under high vacuum for 24 hours and used without further purification in the next step.

C) Preparation of Compound 22b

Benzoic anhydride (0.59 g, 2.6 mmol) was added to a solution of Compound 21b (0.80 g, 1.2 mmol) in N,N-dimethylformamide (3 mL). After stirring for 16 hours at room temperature, the reaction was concentrated under high vacuum. Purification by column chromatography (SiO$_2$, eluting with 50% EtOAc/hexanes) gave Compound 22b (1.36 g, 87% from Compound 17b).

D) Preparation of Compound 23b

Triethylamine trihydroflouride (1.66 mL, 10.2 mmol) was added to a solution of Compound 23b (1.35 g, 1.7 mmol) and triethylamine (0.57 mL, 4.1 mmol) in THF (12 mL). After stirring at room temperature for 48 hours, the reaction was poured into EtOAc and the organic layer was washed with H$_2$O, saturated NaHCO$_3$, brine, dried (Na$_2$SO$_4$) and concentrated. Purification by column chromatography (SiO$_2$, eluting with 20% to 40% acetone in chloroform) gave Compound 23b (1.03 g, 90%).

E) Preparation of (1R,3R,4R,7S)-7-[2-cyanoethoxy (diisopropylamino)-phosphinoxy]-1-[1-(R)-(4,4'-dimethoxytrityl)oxy-ethyl]-3-(4-N-benzoylcytosin-1-yl)-2,5-dioxa-bicyclo[2.2.1]heptane, Compound 24b 2-Cyanoethyl N,N'-tetraisopropylphosphoramidite (0.73 mL, 2.3 mmol) was added to a solution of Compound 23b (1.03 g, 1.53 mmol), tetrazole (85 mg, 1.2 mmol), N-methylimidazole (31 µL, 0.38 mmol) in DMF (7.7 mL). After stirring for 8 hours at room temperature, the reaction was poured into EtOAc and the organic phase was washed with 90% brine, brine, dried (Na$_2$SO$_4$) and concentrated under vacuum. Purification by column chromatography (SiO$_2$, eluting with 60% to 90% EtOAc/hexanes) gave Compound 24b (1.22 g, 91%) as a white solid. 24b $^{31}$P NMR (300 MHz, CDCl$_3$) δ: 149.5, 148.8.

EXAMPLE 5

Preparation of (1R,3R,4R,7S)-7-[2-cyanoethoxy (diisopropylamino)phosphinoxy]-1-[1-(S)-(4,4'-dimethoxytrityl)oxy-ethyl]-3-(6-N-benzoyladenin-9-yl)-2,5-dioxa-bicyclo[2.2.1]heptane, Compound 33a

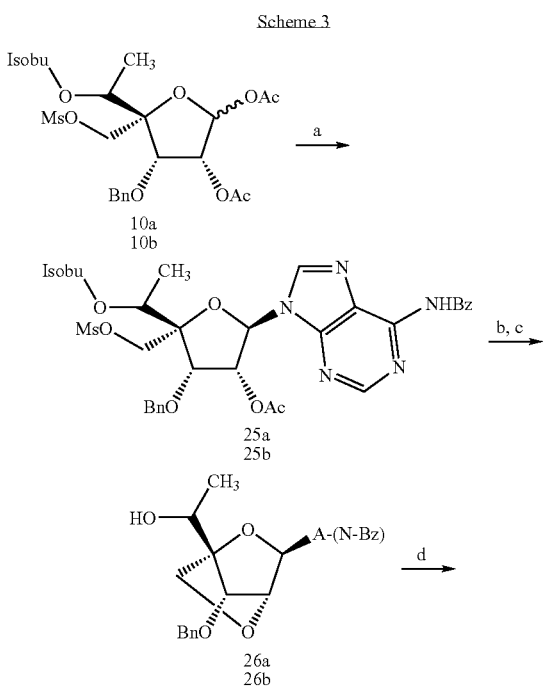

-continued

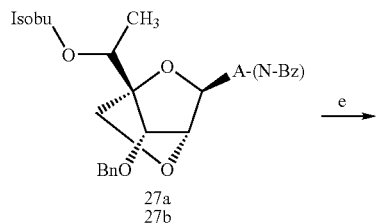

27a
27b

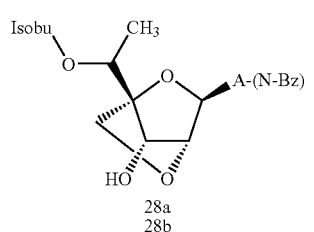

28a
28b

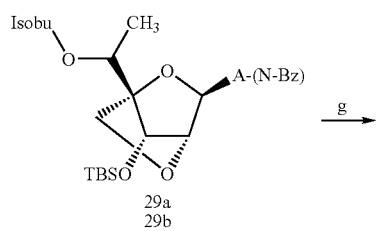

29a
29b

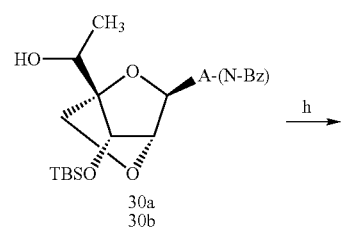

30a
30b

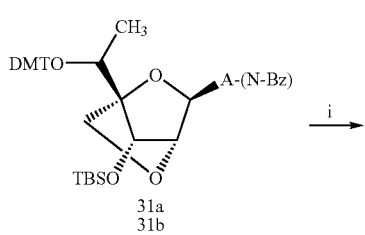

31a
31b

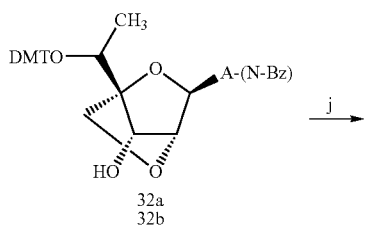

32a
32b

-continued

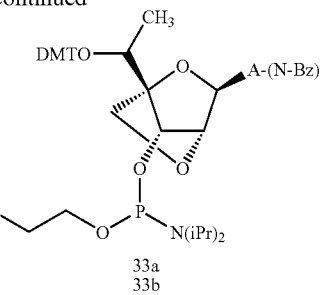

33a
33b a   6-N-Bz-adenine, BSA, TMSOTf
b   $K_2CO_3$, MeOH
c   TMSCl, Pyridine then BzCl, aq. $NH_3$
d   Isobutyric anhydride, DMAP, pyridine, 16 h, rt
e   10% Pd/C, $H_2$ balloon, 24 h to 48
f   TBSCl, imidazole, DMF, rt, 48 h
g   $K_2CO_3$, MeOH, rt, 16 h
h   DMTCl, 2,6-lutidine, pyridine, 45° C., 48 h
i   $Et_3N$•3HF, $Et_3N$, THF, rt, 48 h
j   $(iPr_2)NPO(CH_2)_2CN$, NMI, tetrazole, DMF

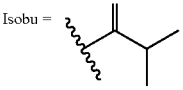

Compound 25a is prepared by the Vorbruggen reaction of Compound 10a using 6-N-Bz-Adenine, BSA and TMSOTf in refluxing dichloroethane. Subsequent reaction of 25a with sodium hydroxide in dioxane/water, followed by reprotection of the 4-amino group with benzoyl chloride provides nucleoside Compound 26a. The phosphoramidite, Compound 33a is prepared from nucleoside Compound 26a following the same steps as illustrated for Compound 19a from Compound 11a.

EXAMPLE 6

Preparation of (1R,3R,4R,7S)-7-[2-cyanoethoxy (diisopropylamino)phosphinoxy]-1-[1-(R)-(4,4'-dimethoxytrityl)oxy-ethyl]-3-(6-N-benzoyladenin-9-yl)-2,5-dioxa-bicyclo[2.2.1]heptane, Compound 33b (Scheme 3)

Compound 25b is prepared by the Vorbruggen reaction of Compound 10b using 6-N-Bz-Adenine, BSA and TMSOTf in refluxing dichloroethane. Subsequent reaction of 25b with sodium hydroxide in dioxane/water, followed by reprotection of the 4-amino group with benzoyl chloride provides nucleoside Compound 26b. The phosphoramidite, Compound 33b is prepared from nucleoside Compound 26b following the same steps as illustrated for Compound 19b from Compound 11b.

EXAMPLE 7

Preparation of (1R,3R,4R,7S)-7-[2-cyanoethoxy (diisopropylamino)phosphinoxy]-1-[1-(S)-(4,4'-dimethoxytrityl)oxy-ethyl]-3-(2-N-isobutyrylguanin-9-yl)-2,5-dioxa-bicyclo[2.2.1]heptane, Compound 42a Scheme 4

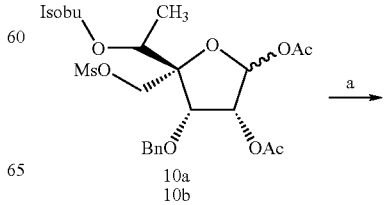

10a
10b a 2-amino-6-chloropurine, BSA, TMSOTf, DCE, reflux;
b 3-Hydroxypropionitrile, NaH, THF, 4 h;
c Isobutyric anhydride, DMAP, pyridine;
d Pd/C, H₂ balloon;
e TBSCl, Imidazole, DMF, rt;
f K₂CO₃, MeOH, rt, 16 h
g DMTCl, 2,6-lutidine, pyridine, 45° C., 48 h
h Et₃N·3HF, Et₃N, THF, rt, 48 h
i (iPr₂)NPO(CH₂)₂CN, NMI, tetrazole, DMF Compound 34a is prepared by the Vorbruggen reaction of Compound 10a using 2-amino-6-chloropurine, BSA and TMSOTf in refluxing dichloroethane. Reaction of nucleoside 34a with 3-hydroxypropionitrile and sodium hydride provides the cyclized nucleoside 35a. The phosphoramidite, Compound 42a is prepared from nucleoside Compound 35a following the same steps as illustrated for Compound 19a from Compound 11a.

EXAMPLE 8

Preparation of (1R,3R,4R,7S)-7-[2-cyanoethoxy (diisopropylamino)phosphinoxy]-1-[1-(R)-(4,4'-dimethoxytrityl)oxy-ethyl]-3-(2-N-isobutyrylguanin-9-yl)-2,5-dioxa-bicyclo[2.2.1]heptane, Compound 42b (Scheme 4)

Compound 34b is prepared by the Vorbruggen reaction of Compound 10b using 2-amino-6-chloropurine, BSA and TMSOTf in refluxing dichloroethane. Reaction of nucleoside 34b with 3-hydroxypropionitrile and sodium hydride provides the cyclized nucleoside 35b. The phosphoramidite, Compound 42b is prepared from nucleoside Compound 35b following the same steps as illustrated for Compound 19b from Compound 11b.

EXAMPLE 9

Preparation of Compound 48

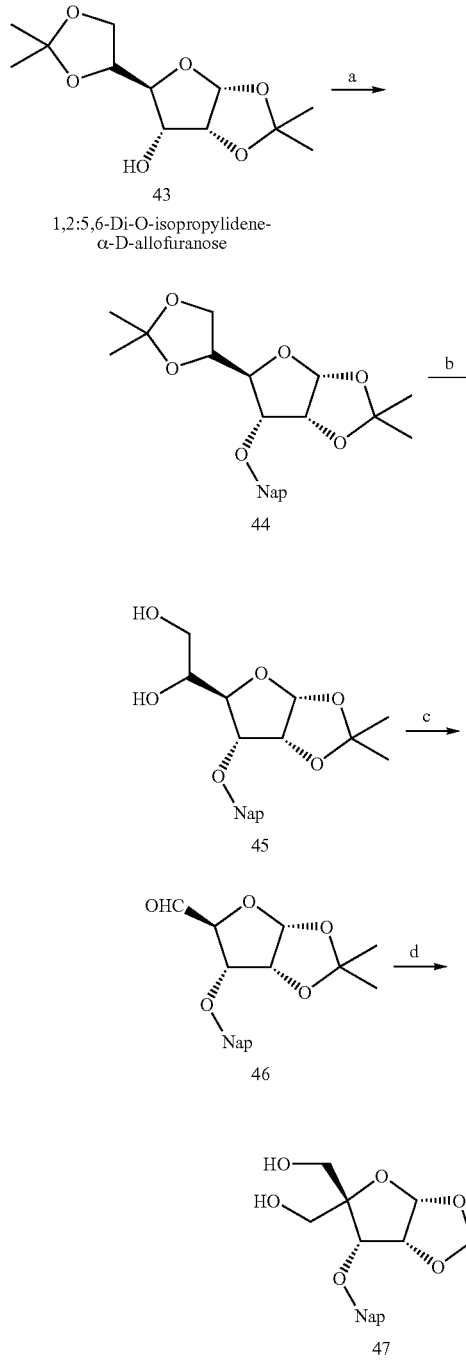

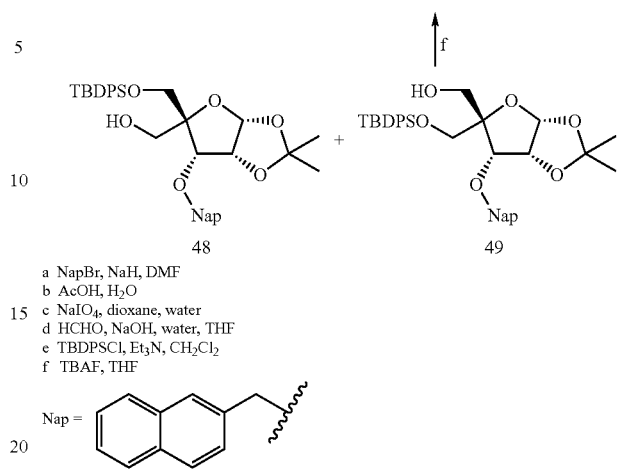

a NapBr, NaH, DMF
b AcOH, H$_2$O
c NaIO$_4$, dioxane, water
d HCHO, NaOH, water, THF
e TBDPSCl, Et$_3$N, CH$_2$Cl$_2$
f TBAF, THF

A) Preparation of Compound 44

Commercially available 1,2;5,6-di-O-isopropylidene-α-D-allofuranose, Compound 43, (135 g, 519.0 mmol) and 2-(bromomethyl)-naphthalene (126 g, 570.0 mmol) were dissolved in DMF (500 mL) in a three-necked flask (500 mL) and the reaction was cooled in an ice bath. Sodium hydride (60% w/w, 29 g, 727.0 mmol) was carefully added (6 g portions every 10 minutes) to the reaction and the stirring was continued for another 60 minutes after the addition was complete. At this time TLC analysis showed no more starting sugar 43. The reaction was carefully poured onto crushed ice (ca. 500 g) and the resulting slurry was stirred vigorously until all the ice melted. The resulting off-white solid was collected by filtration and suspended in water. The suspension was stirred vigorously using a mechanical stirrer for 30 minutes after which the solid was collected by filtration and suspended in hexanes. The suspension was stirred vigorously for 30 minutes after which the solid was collected by filtration and air dried for 4-6 hours and then dried under high vacuum over P$_2$O$_5$ for 16 hours to provide Compound 44 (206.0 g, 99%) as an off-white solid. $^1$H NMR (300 MHz, CDCl$_3$) δ: 7.85 (m, 4H), 7.48 (m, 3H), 5.74 (s, 1H), 4.92 (d, 1H, J=11.7), 4.75 (d, 1H, J=11.6), 4.58 (m, 1H), 4.36 (m, 1H), 4.15 (m, 1H), 4.03-3.86 (m, 3H), 1.61 (s, 3H), 1.36 (s, 9H).

B) Preparation of Compound 45

Compound 44 (200.0 g, 0.5 moles) was added in small portions to a solution of acetic acid (2.2 L) and water (740 mL). The reaction was stirred at room temperature for 16 h after which, TLC analysis (30% EtOAc/hexanes) indicated complete consumption of 44. The reaction was then concentrated under reduced pressure until most of the acetic acid was removed. The remaining solution was poured into a stirred mixture of EtOAc (1 L) and water (1 L). Solid KOH was then added to the above mixture until the aqueous layer was strongly basic (pH>12). The organic layer was then separated, washed with saturated sodium bicarbonate solution, brine, dried (Na$_2$SO$_4$), filtered and concentrated under reduced pressure to provide Compound 45 as a yellow foam, which was used without any further purification.

C) Preparation of Compound 46

A solution of NaIO$_4$ (107.0 g) in water (3 L) was added over 40 minutes to a stirred (mechanical stirrer) solution of Compound 45 (crude from above) in dioxane (1.5 L) After 60 minutes the reaction mixture was poured into EtOAc (1.5 L) and the organic layer was separated, washed with water (1 L), brine (1 L), dried (Na$_2$SO$_4$) and concentrated to provide Compound 46 as a yellow oil, which was used without any further purification.

D) Preparation of Compound 47

Compound 46 (crude from above) was dissolved in a mixture of THF (500) and water (500 mL) and the reaction was cooled in an ice bath. 2N NaOH (600 mL) and formaldehyde (250 mL of a 37% aqueous solution) were added to the reaction and the stirring was continued at room temperature for 3 days. The reaction was then poured into EtOAc (1 L) and washed with water (1 L), brine (1 L) and evaporated under reduced pressure until approximately 200 mL of EtOAc was left (a white precipitate was formed in the process). Hexanes (300 mL) was added to the precipitate and the mixture was allowed to stand for 16 hours after which the white solid was collected by filtration, washed with hexanes and dried under high vacuum over P$_2$O$_5$ to provide Compound 47 as a white solid (124 g, 66% from 44). $^1$H NMR (300 MHz, CDCl$_3$) δ: 7.85 (m, 4H), 7.48 (m, 3H), 5.75 (d, 1H, J=3.9), 4.96 (d, 1H, J=11.8), 4.75 (d, 1H, J=11.8), 4.66 (m, 1H), 4.26 (d, 1H, J=5.2), 3.95 (m, 2H), 3.79 (m, 1H), 3.63 (m, 1H), 2.39 (m, 1H, OH), 1.66 (s, 3H), 1.34 (s, 3H).

E) Preparation of Compounds 48 and 49 tert-Butyldiphenylchlorosilane (305.0 mmol, 84.0 mL) was added to a cold (0° C.) stirring solution of Compound 47 (278.0 mmol, 100.0 g) and triethylamine (305 mmol, 43.0 mL) in dichloromethane (600 mL). After the addition was complete, the reaction was warmed to room temperature and the stirring was continued for 16 hours. MeOH (50 mL) was added (to quench the excess TBDPSCl) to the reaction and the stirring was continued for another 2 hours at room temperature. The reaction was then diluted with chloroform and the organic layer was washed with 10% HCl, saturated NaHCO$_3$, brine, dried (Na$_2$SO$_4$) and concentrated to provide a thick oil. Hexanes (150 mL) was added to the oil and the mixture was sonicated until a solution resulted. The solution was now seeded with a small amount of 6 (previously isolated by column chromatography). After standing for 16 hours additional hexanes was added to the thick slurry and the solid was collected by filtration. The solid was then resuspended in hexanes and stirred vigorously for 30 minutes. The solid was collected by filtration to provide 6 (80.5, 48% g) after drying under high vacuum for 16 hours. The filtrates were combined and concentrated under reduced pressure. The resulting oil was redissolved in minimum amount of hexanes and passed through a plug of silica gel (eluting with 20% EtOAc in hexanes). Fractions containing the product 6 were combined, concentrated and crystallized as described above to provide a second crop of 6 (20 g, 12%) as a white solid. Further elution of the silica gel plug with 50% EtOAc in hexanes provided pure Compound 48 (40.0 g, 24%) as a thick oil. In addition a mixture of 48 and 49 (ca 15 g, 9%) was also isolated as a thick oil. Diol 48; $^1$H NMR (300 MHz, CDCl$_3$) δ: 7.83 (m, 4H), 7.56 (m, 7H), 7.30 (m, 6H), 5.80 (s, 1H), 4.97 (d, 1H, J=11.4), 4.70 (m, 2H), 4.46 (m, 1H), 3.92-3.66 (m, 4H), 2.39 (m, 1H, OH), 1.67 (s, 3H), 1.37 (s, 3H), 0.92 (s, 9H). Diol 7; $^1$H NMR (300 MHz, CDCl$_3$) δ: 7.9-7.3 (m, 17H), 5.71 (d, 1H, J=3.9), 4.86 (d, 1H, J=12.2), 4.74 (d, 1H, J=12.2), 4.56 (m, 1H), 4.22 (d, 1H, J=11.1), 4.18 (m, 1H), 4.07 (d, 1H, J=11.1), 4.02 (dd, 1H, J=4.2, 12.0), 3.64 (dd, 1H, J=9.4, 11.9), 1.89 (m, 1H), 1.25 (s, 6H), 1.05 (s, 9H).

F) Recover Compound 47 from Compound 49

Tetrabutylammonium fluoride (70 mL of a 1 M solution in THF) was added to a cold (0° C.) stirring solution of diol 49 (62.7 mmol, 37.5 g) in THF (250 mL) after which, the reaction was allowed to warm to room temperature gradually. After stirring for an additional 72 hours, the reaction was concentrated under vacuum and the residue was poured onto crushed ice. The flask was rinsed with some additional THF (3 times) and added to the above suspension. The supernatant was removed by decantation and the solid at the bottom was added to a stirring mixture of hexanes (200 mL) and water (200 mL). After stirring for 2 hours, the flocculent solid was collected by filtration, washed with additional water and hexanes and dried under high vacuum to provide Compound 47 (20 g, 89%) as a white solid.

EXAMPLE 10

Preparation of Compound 60

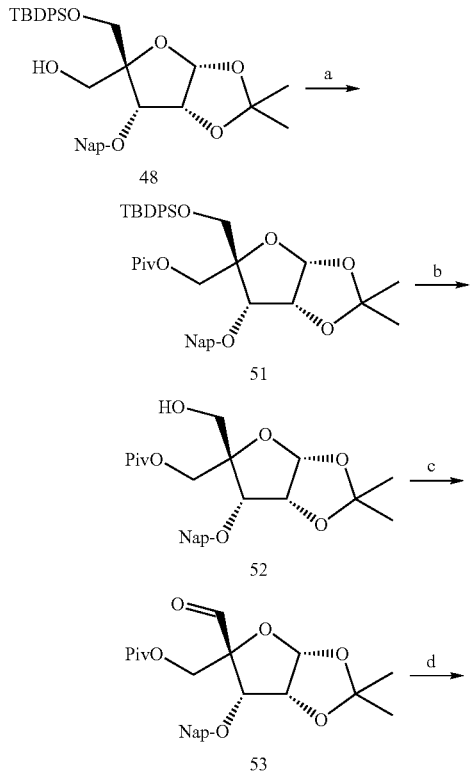

Scheme 6

-continued

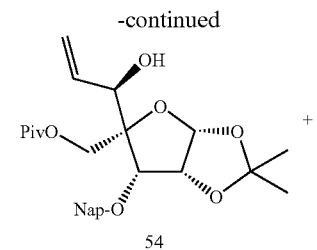

54

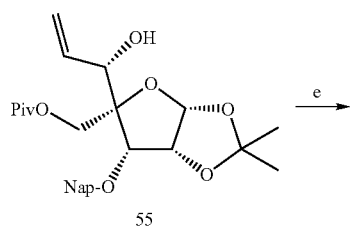

55

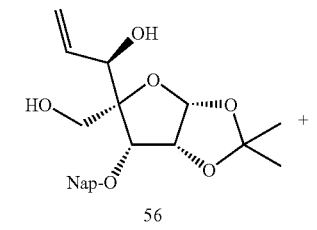

56

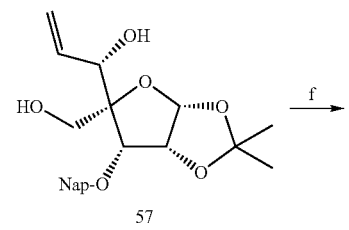

57

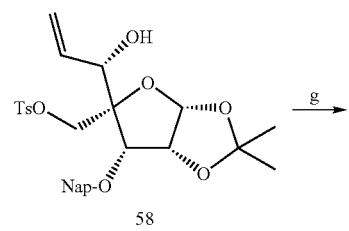

58

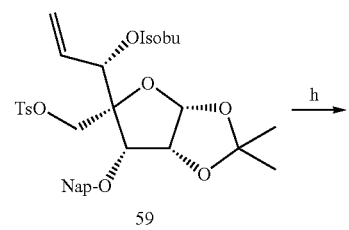

59

-continued

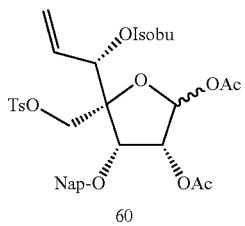

60 a Pivaloyl chloride, DIPEA, DMAP, CH$_2$Cl$_2$
b 70% HF/pyridine, THF
c Oxalyl chloride, DMAP, Et$_3$N, CH$_2$Cl$_2$
d Vinyl MgBr, THF
e NaOH, MeOH, water
f TsCl, pyridine
g Isobutyryl chloride, DIPEA, DMAP, CH$_2$Cl$_2$ Isobu = [structure with C(=O)CH(Me)Me]

A) Preparation of Compound 51

Pivaloyl chloride (25 mmol, 3.0 mL) was added dropwise to a cold (0° C.) solution of Compound 48 (16.7 mmol, 10.0 g), diisopropylethylamine (25.0 mmol, 4.4 mL) and dimethylaminomethylpyridine (2.5 mmol, 0.30 g) in dichloromethane (35 mL). After stirring at room temperature for 16 hours, the reaction was diluted with chloroform and the organic layer was washed with 5% HCl, saturated NaHCO$_3$, brine, dried (Na$_2$SO$_4$) and concentrated to provide crude Compound 51, which was used without any further purification.

B) Preparation of Compound 52

70% HF/pyridine (4.2 mL) was added to a cold (0° C.) solution of crude 51 (from above). After stirring for 16 hours at room temperature, additional 70% HF/pyridine (2.5 mL) was added to the reaction. After stirring another 2 days at room temperature, triethylamine (7.5 mL) was carefully added to the reaction. After stirring for 1 hour, the reaction was carefully quenched with saturated NaHCO$_3$ until pH>10. The reaction was diluted with EtOAc and the organic layer was further washed with brine, dried (Na$_2$SO$_4$) and concentrated. Purification by column chromatography (SiO$_2$, eluting with 25 to 40% EtOAc in hexanes) provided Compound 52 (7.01 g, 95% from Compound 48) as an oil.

C) Preparation of Compound 53

DMSO (3.30 mL, 46.7 mmol) was added to a cold (−78° C.) solution of oxalyl chloride (23.3 mmol, 2.0 mL) in dichloromethane (120 mL). After stirring for 30 minutes, Compound 52 (15.6 mmol, 6.91 g) in dichloromethane (30 mL) was added to the reaction via a cannula. After stirring for 45 minutes at −78° C., triethylamine (70.0 mmol, 9.60 mL) was added and the reaction was allowed to warm up to 0° C. TLC analysis at this time indicated no starting material, Compound 52, so the reaction was diluted with chloroform and the organic layer was washed with 10% HCl, saturated NaHCO$_3$, brine, dried (Na$_2$SO$_4$) and concentrated to provide Compound 53, which was used without any further purification.

D) Preparation of Compounds 54 and 55

Vinyl magnesium bromide (1 M in THF, 31.1 mL) was slowly added to a cold (−78° C.) solution of Compound 53 in THF (120 mL). After stirring at −78° C. for 2 hours, the reaction was quenched with saturated NH$_4$Cl and the reaction was diluted with EtOAc. The organic layer was washed with 10% HCl, saturated NaHCO$_3$, brine, dried (Na$_2$SO$_4$) and concentrated to provide Compound 54 and Compound 55 as a mixture, which was used without any further purification.

E) Preparation of Compounds 56 and 57

A solution of NaOH (4M, 12.5 mL) was added to a solution of Compounds 54 and Compound 55 in dioxane/methanol (30 mL/10 mL). After stirring for 4 hours at room temperature, the solvents were evaporated under reduced pressure and the residue was dissolved in EtOAc. The organic layer was washed with water, brine, dried (Na$_2$SO$_4$) and concentrated. Purification by column chromatography (SiO$_2$, eluting with 33 to 40% EtOAc in hexanes) provided Compound 57 (2.42 g, 40% from 53) as an oil. Increasing polarity (60% EtOAc in hexanes) of the eluant provided Compound 56 (0.82 g, 14% from Compound 53). 57 $^1$H NMR (300 MHz, CDCl$_3$) δ: 7.94-7.73 (m, 4H), 7.60-7.46 (m, 3H), 6.04-5.85 (m, 1H), 5.69 (d, 1H, J=3.6), 5.36 (d, 1H, J=17.3), 5.24 (d, 1H, J=10.6), 4.97 (d, 1H, J=11.7), 4.74 (d, 1H, J=11.7), 4.59 (m, 1H), 4.33 (m, 2H), 4.19 (d, 1H, J=11.9), 3.85 (d, 1H, J=11.9), 1.65 (s, 3H), 1.34 (s, 3H).

F) Preparation of Compound 58

Tosyl chloride (9.3 mmol, 1.77 g) was added to a cold (0° C.) solution of Compound 57 (2.43 g, 6.29 mmol) in pyridine (12.6 mL). After stirring at 0° C. for 8 hours, the reaction was quenched with water and diluted with EtOAc. The organic layer was washed with 5% HCl, saturated NaHCO$_3$, brine, dried (Na$_2$SO$_4$) and concentrated. Purification by column chromatography (SiO$_2$, eluting with 15 to 25% EtOAc in hexanes) provided Compound 58 (2.58 g, 76%) as a white solid. Unreacted 57 (0.0.39 g, 16%) was also isolated.

G) Preparation of Compound 59

Isobutyryl chloride (6.9 mmol, 0.73 mL) was added to a cold (0° C.) solution of Compound 58 (4.6 mmol, 2.48 g), diisopropylethylamine (6.9 mmol, 0.88 mL) and dimethylaminomethylpyridine (0.68 g, 83 mg) in dichloromethane (9 mL). After 2 hours at 0° C., additional isobutyryl chloride (6.9 mmol, 0.73 mL) and diisopropylethylamine (6.9 mmol, 0.88 mL) were added to the reaction. After another 2 hours at 0° C., additional isobutyryl chloride (6.9 mmol, 0.73 mL) and diisopropylethylamine (6.9 mmol, 0.88 mL) were added to the reaction and the reaction was stirred at 0° C. for 16 hours. Water was carefully added to the reaction to quench any unreacted acid chloride and the stirring was continued for 1 hour at room temperature. The reaction was then diluted with chloroform and the organic layer was washed with 5% HCl, saturated NaHCO$_3$, brine, dried (Na$_2$SO$_4$) and concentrated. Purification by column chromatography (SiO$_2$, eluting with 25% EtOAc in hexanes) provided Compound 59 (2.2 g, 83%) as an oil. Unreacted 58 (0.31 g, 13%) was also isolated after purification.

H) Preparation of Compound 60

Concentrated sulfuric acid (3-4 drops) was added to a solution of Compound 59 (3.6 mmol, 2.20 g) in acetic acid (11 mL) and acetic anhydride (3 mL). After stirring for 2 hours at room temperature, the solvents were removed under high vacuum on a rotary evaporator (no heat) and the residue was dissolved in EtOAc. The organic layer was carefully washed with saturated NaHCO$_3$, brine, dried (Na$_2$SO$_4$) and concentrated to provide Compound 60, which was dried under high vacuum over P$_2$O$_5$ and used without any further purification. 60 LCMS: M+23 calcd. 677.2, found 677.1; LC retention time 2.05 min.

EXAMPLE 11

Preparation of (1R,3R,4R,7S)-7-[2-cyanoethoxy (diisopropylamino)phosphinoxy]-1-[1-(S)-(4,4'-dimethoxytrityl)oxy-(3-propenyl)]-3-(uracil-1-yl)-2,5-dioxa-bicyclo[2.2.1]heptane (69)

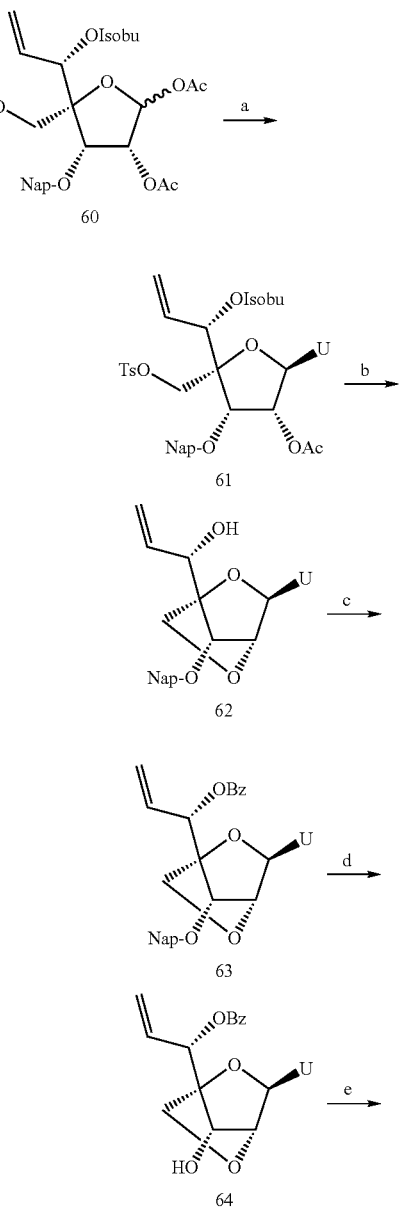

Scheme 7

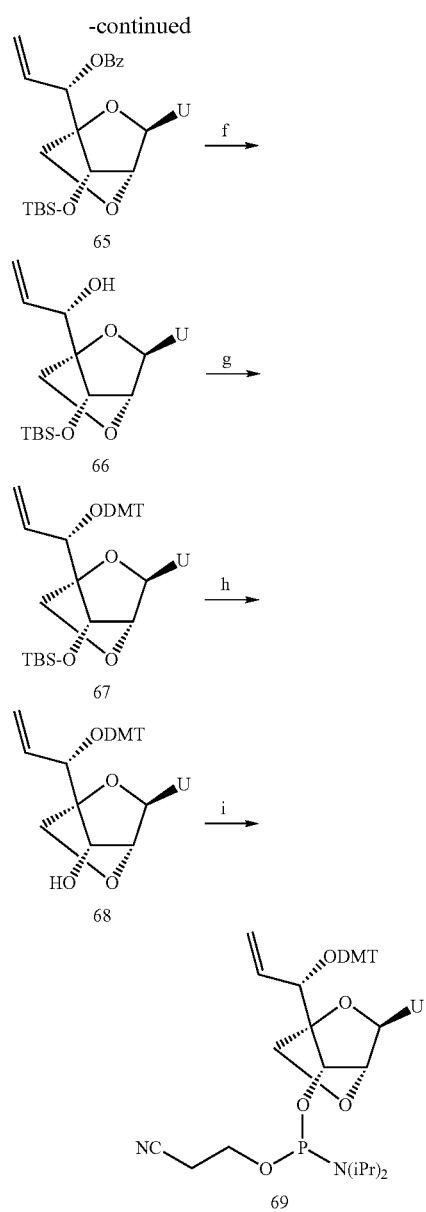

a Uracil, BSA, TMSOTf, CH₃CN
b NaOH, dioxane, water
c BzCl, pyridine
d DDQ, CH₂Cl₂, water
e TBSCl, imidazole, DMF
f t-BuNH₂ or aqueous ammonia
g DMTCl, pyridine, 2,6-lutidine
h Et₃N·3HF, Et₃N, THF
i (iPr₂N)₂POCH₂CH₂CN, tetrazole, NMI, DMF

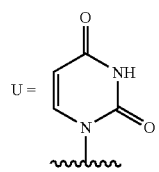

A) Preparation of Compound 61

N,O-bis-trimethylsilylamide (18.0 mmol, 4.4 mL) was added to a suspension of Compound 60 (3.6 mmol, crude from above) and uracil (7.2 mmol, 0.81 g) in acetonitrile (18 mL) and the suspension was gently heated (using a heat gun) until a solution resulted. The reaction was cooled in an ice bath and TMSOTf (7.2 mmol, 1.3 mL) was added to the reaction. After the addition was complete, the ice bath was removed and the reaction was refluxed for 2 hours after which it was cooled to room temperature, diluted with EtOAc and carefully quenched with saturated NaHCO₃ solution. The organic layer was further washed with brine, dried (Na₂SO₄) and concentrated to provide crude Compound 61, which was used without any further purification.

B) Preparation of Compound 62

A solution of NaOH (2M, 7.2 mL) was added to a cold (0° C.) solution of crude Compound 61 (from above) in dioxane (10 mL). After 2 hours at 0° C., an additional amount of NaOH (2M, 10 mL) was added to the reaction. After stirring for 16 hours at room temperature, the reaction was acidified with 5% HCl (pH 4-5), diluted with EtOAc and the organic layer was washed with water, brine, dried (Na₂SO₄) and concentrated. A white precipitate was formed, which was carefully washed with ether and dried over high vacuum to provide nucleoside Compound 62 (0.97 g, 64%). Purification of the ether washes by column chromatography (SiO₂, eluting with 25% acetone in chloroform) provided an additional amount of partially pure Compound 62 (0.10 g, 7%).

C) Preparation of Compound 63

Benzoic anhydride (2.8 mmol, 0.64 g) was added to a solution of Compound 62 (2.0 mmol, 0.85 g) in pyridine (4 mL). After stirring at room temperature for 6 hours, the reaction was quenched with water and diluted with EtOAc. The organic layer was washed with saturated NaHCO₃, brine, dried (Na₂SO₄) and concentrated. Purification by column chromatography (SiO₂, eluting with 50% EtOAc in hexanes) provided Compound 63 (1.069 g, quantitative) as a white solid.

D) Preparation of Compound 64

DDQ (3.8 mmol, 0.86 g) was added to a solution of Compound 64 (1.9 mmol, 1.0 g) in dichloromethane (19 mL) and water (1 mL). After stirring at room temperature for 24 hours, the reaction was concentrated under reduced pressure. The residue was dissolved in EtOAc and the organic layer was washed with water, 10% sodium bisulfite, saturated NaHCO₃, brine, dried (Na₂SO₄) and concentrated. Purification by column chromatography (SiO₂, eluting with 75% EtOAc in hexanes) provided Compound 64 (0.74 g, quantitative).

E) Preparation of Compound 65

TBSCl (5.8 mmol, 0.87 g) was added to a solution of Compound 64 (1.9 mmol, 0.75 g) and imidazole (11.6 mmol, 0.79 g) in DMF (5 mL). After stirring at room temperature for 16 hours, the reaction was diluted with EtOAc and the organic layer was washed with water, brine, dried (Na₂SO₄) and concentrated. Purification by column chromatography (SiO₂, 50% EtOAc in hexanes) provided Compound 65 (0.89 g, 94%) as a white foam.

F) Preparation of Compound 66

Compound 65 (1.6 mmol, 0.8 mmol) was dissolved in a solution of ammonia in methanol (7M, 25 mL). After heating in a sealed vessel at 45° C. for 4 days, the solvent was removed under reduced pressure. Purification by chromatography (SiO₂, 2 to 4% methanol in chloroform) provided compound 66 (0.65 g, quantitative) as a white solid. 66 ¹H NMR (300 MHz, CDCl₃) δ: 8.57 (s, br, 1H), 7.84 (d, 1H, J=8.2), 6.10-5.96 (m, 1H), 5.74 (d, 1H, J=8.2), 5.64 (s, 1H), 5.41-5.44 (m, 2H), 4.35 (m, 1H), 4.26 (s, 1H), 4.13 (s, 1H), 3.95 (d, 1H, J=7.8), 3.66 (d, 1H, J=7.8), 2.04 (d, 1H, J=4.3), 0.90 (s, 9H), 0.11 (s, 3H), 0.10 (s, 3H).

G) Preparation of Compound 67

A solution of compound 66 (0.25 mmol, 0.1 g), DMTCl (0.63 mmol, 0.21 g) and 2,6-lutidine (0.63 mmol, 73 µL) in pyridine (1.25 mL) was heated at 45° C. for 10 days. The reaction was cooled to room temperature and diluted with EtOAc. The organic layer was washed with saturated sodium bicarbonate, brine, dried (Na₂SO₄) and concentrated under reduced pressure. Purification by column chromatography (SiO₂, eluting with 15 to 45% EtOAc in hexanes) provided compound 67 (0.16 g, 93%) as a white solid. 67 ¹H NMR (300 MHz, CDCl₃) δ: 8.92 (s, br, 1H), 8.26 (d, 1H, J=8.2), 7.53-7.24 (m, 9H), 6.97-6.78 (m, 4H), 6.08-5.88 (m, 1H), 5.73 (s, 1H), 5.68 (d, 1H, J=8.2), 4.83 (s, 1H, J=11.0), 4.58 (d, 1H, J=17.3), 4.37 (s, 1H), 4.04 (d, 1H, J=9.5), 3.84 (s, 6H, 3.78, m, 1H, partially overlapped), 3.55 (d, 1H, J=7.9), 0.83 (s, 9H), 0.11 (s, 3H), 0.00 (s, 3H).

H) Preparation of Compound 68

Triethylamine trihydroflouride (1.3 mmol, 0.21 mL) was added to a solution of compound 67 (0.22 mmol, 0.15 g) and triethylamine (0.54 mmol, 75 µL) in THF (2 mL). After stirring at room temperature for 2 days, the reaction was diluted with EtOAc and the organic layer was washed with saturated NaHCO₃, brine, dried (Na₂SO₄) and concentrated. LCMS: M+23 calcd. 607.2, found 607.2; LC retention time 3.51 min

I) Preparation of Compound 69

Phosphoramidite compound 69 is prepared from compound 68 according to the procedure described for the preparation of phosphoramidite 19a from compound 18a in example 1.

EXAMPLE 12

Preparation of (1R,3R,4R,7S)-7-[2-cyanoethoxy(diisopropylamino)phosphinoxy]-1-[1-(S)-(4,4'-dimethoxytrityl)oxy-(3-propenyl)]-3-(4-N-benzoyl-cytosin-1-yl)-2,5-dioxa-bicyclo[2.2.1]heptane (73)

Scheme 8

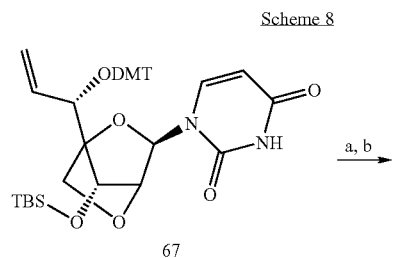

Phosphoramidite 73 is prepared from Compound 67 using the same general procedures described in example 3 for the preparation of phosphoramidite 24a from Compound 17a.

EXAMPLE 13

Alternate Route for the Preparation of (1R,3R,4R,7S)-7-[2-cyanoethoxy(diisopropylamino)-phosphinoxy]-1-[1-(S)-(4,4'-dimethoxytrityl)oxy-(3-propenyl)]-3-(4-N-benzoylcytosin-1-yl)-2,5-dioxa-bicyclo[2.2.1]heptane (73)

Scheme 9

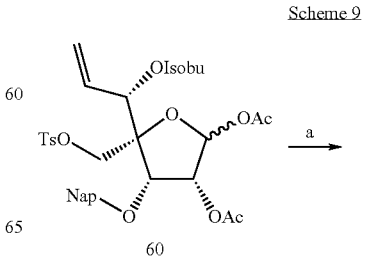

a POCl₃, 1,2,4-triazole, Et₃N, CH₃CN
b Aqueous Ammonia
c Bz₂O, DMF
d Et₃N·3HF, Et₃N, THF
e (iPr₂N)₂POCH₂CH₂CN, tetrazole, NMI, DMF -continued

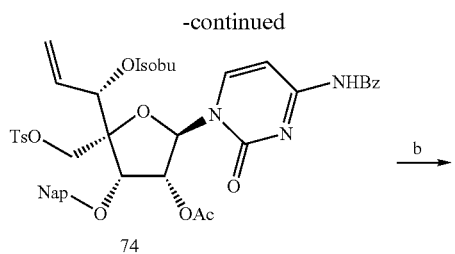
74

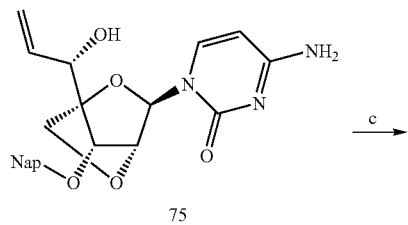
75

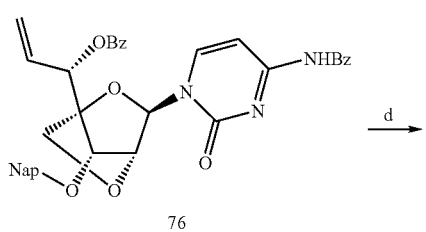
76

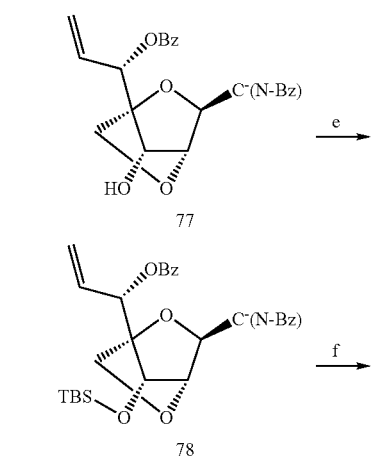
77
78
79
71

-continued

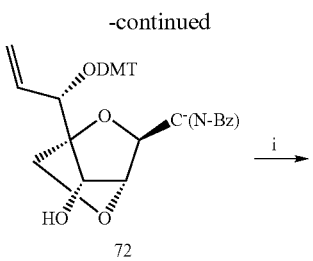
72

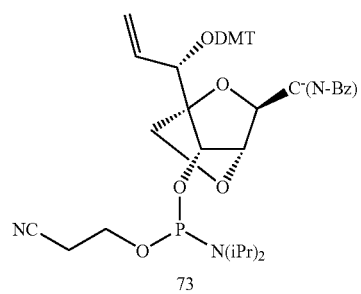
73 a N-Benzoyl-Cytosine, BSA, TMSOTf
b NaOH, MeOH, water
c BzCl, pyridine
d DDQ, CH$_2$Cl$_2$, water
e TBSCl, imidazole, DMF
f t-BuNH$_2$ or aqueous ammonia
g DMTCl, 2,6-lutidine, pyridine
h Et$_3$N·3HF, Et$_3$N, THF
i (iPr$_2$N)$_2$POCH$_2$CH$_2$CN, tetrazole, NMI, DMF Compound 73 is prepared using the same general procedures described for the preparation of phosphoramidite Compound 69 from Compound 60 in example 11. Vorbruggen reaction of Compound 60 with N-benzoyl-cytosine, BSA and TMSOTf in refluxing acetonitrile provides nucleoside Compound 74. Treatment of 74 with aqueous NaOH solution effects cyclization to Compound 75. Protection of the 5'-hydroxyl group and the exocyclic amine with BzCl in pyridine provides Compound 76. Further processing of Compound 76 to phosphoramidite Compound 71 is similar to the procedures described for the preparation of phosphoramidite Compound 69 from Compound 63.

EXAMPLE 14

Preparation of (1R,3R,4R,7S)-7-[2-cyanoethoxy(diisopropylamino)phosphinoxy]-1-[1-(S)-(4,4'-dimethoxytrityl)oxy-(3-propenyl)]-3-(6-N-benzoyladenin-9-yl)-2,5-dioxa-bicyclo[2.2.1]heptane (88)

Scheme 10

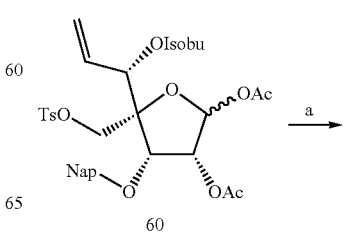
60

-continued

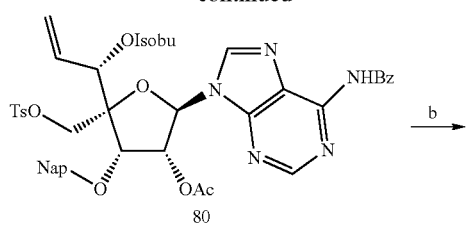
80

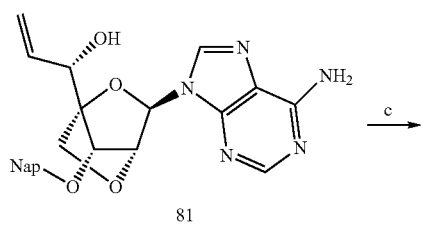
81

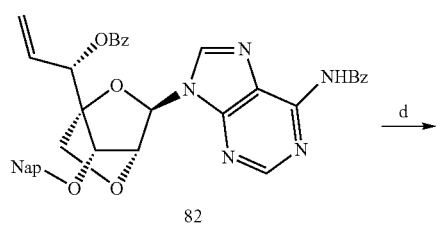
82

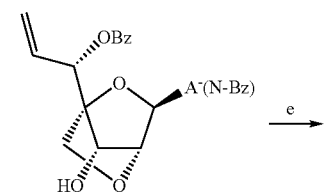
83

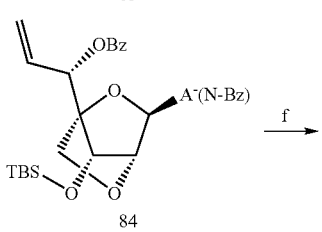
84

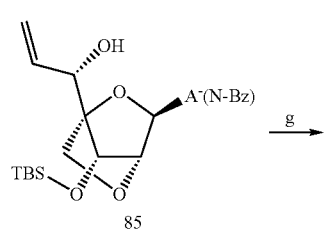
85

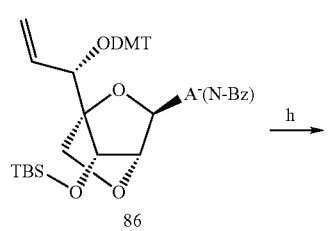
86

-continued

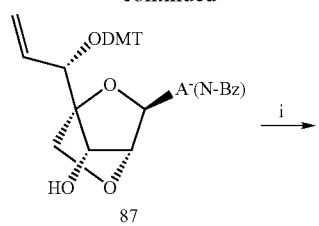
87

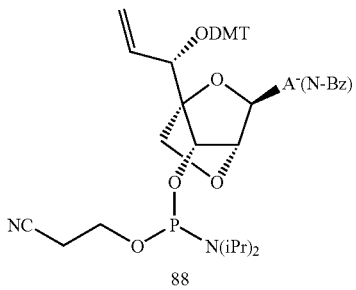
88 a  N-Benzoyl-Adenine, BSA, TMSOTf
b  NaOH, MeOH, water
c  BzCl, pyridine
d  DDQ, CH$_2$Cl$_2$, water
e  TBSCl, imidazole, DMF
f  t-BuNH$_2$ or aqueous ammonia
g  DMTCl, 2,6-lutidine, pyridine
h  Et$_3$N•3HF, Et$_3$N, THF
i  (iPr$_2$N)$_2$POCH$_2$CH$_2$CN, tetrazole, NMI, DMF Compound 88 is prepared using the same general procedures described for the preparation of phosphoramidite Compound 69 from Compound 60 in example 11. Vorbruggen reaction of Compound 60 with N-benzoyl-adenine, BSA and TMSOTf in refluxing dichloroethane provides nucleoside Compound 80. Treatment of 80 with aqueous NaOH solution effects cyclization to Compound 81. Protection of the 5'-hydroxyl group and the exocyclic amine with BzCl in pyridine provides Compound 82. Further processing of Compound 82 to phosphoramidite Compound 88 is similar to the procedures described for the preparation of phosphoramidite Compound 69 from Compound 63.

EXAMPLE 15

Preparation of (1R,3R,4R,7S)-7-[2-cyanoethoxy (diisopropylamino)phosphinoxy]-1-[1-(S)-(4,4'-dimethoxytrityl)oxy-(3-propenyl)]-3-(2-N-isobutyrylguanin-9-yl)-2,5-dioxa-bicyclo[2.2.1]heptane (97)

Scheme 11

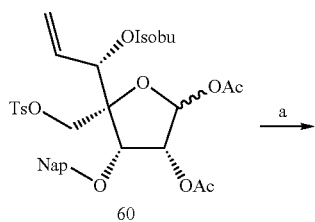
60

-continued

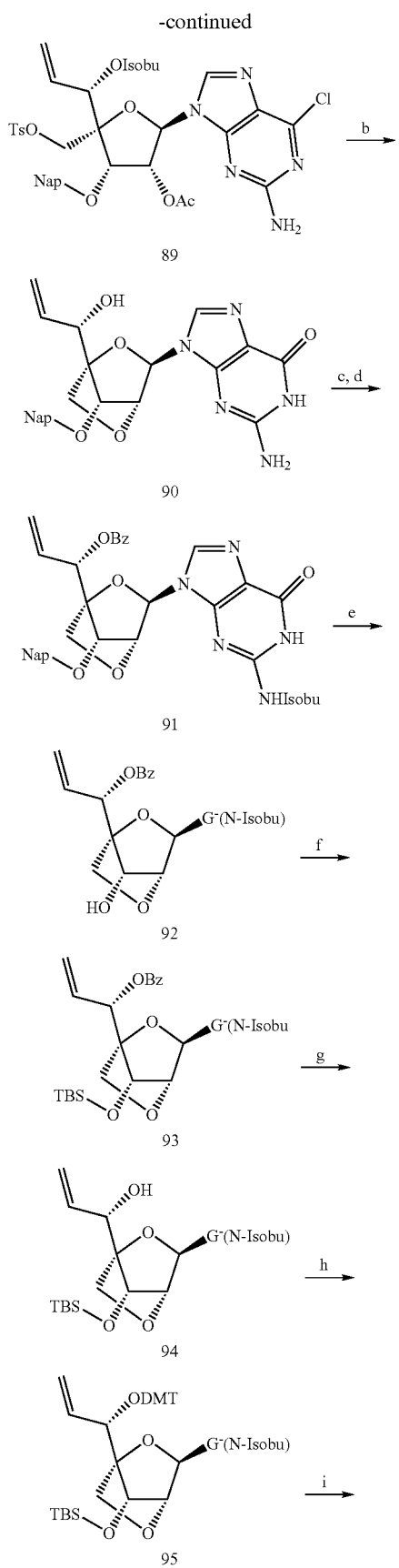

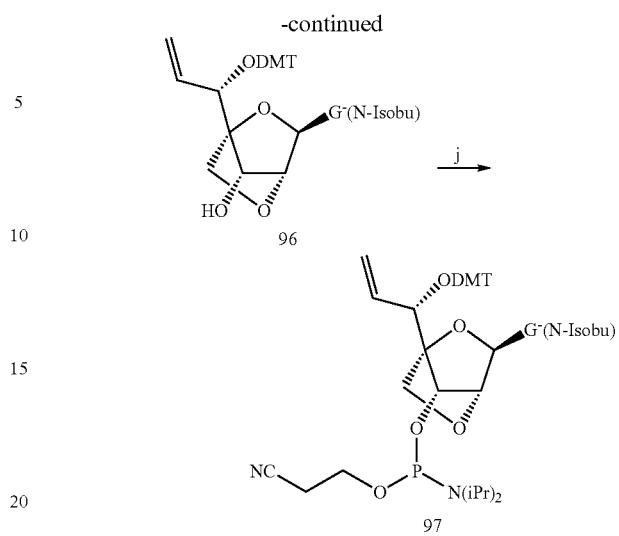

a 2-amino-6-chloropurine, BSA, TMSOTf
b 3-Hydroxypropionitrile, NaH, THF
c TMSCl, pyridine, isobutyryl chloride,
d BzCl, pyridine
e DDQ, CH$_2$Cl$_2$, water
f TBSCl, imidazole, DMF
g t-BuNH$_2$ or aqueous ammonia
h DMTCl, 2,6-lutidine, pyridine
i Et$_3$N•2HF, Et$_3$N, THF
j (iPr$_2$N)$_2$POCH$_2$CH$_2$CN, tetrazole, NMI, DMF Compound 97 is prepared using the same general procedures described for the preparation of phosphoramidite Compound 69 from Compound 60 in example 11. Vorbruggen reaction of Compound 60 with 2-amino-6-chloropurine, BSA and TMSOTf in refluxing dichloroethane provides nucleoside Compound 89. Treatment of Compound 89 with 3-hydroxypropionitrile and sodium hydride effects cyclization to Compound 90. Transient protection of the 5'hydroxyl group as the trimethylsilyl ether is followed by protection of the exocyclic amino group with isobutyryl chloride. Deprotection of the trimethyl silyl ether during aqueous workup conditions, followed by protection of the 5'hydroxyl group as the benzoate ester (benzoyl chloride, pyridine) provides Compound 91. Further processing of Compound 91 to phosphoramidite Compound 97 is similar to the procedures described for the preparation of phosphoramidite Compound 69 from Compound 63.

EXAMPLE 16

Preparation of (1R,3R,4R,7S)-7-[2-cyanoethoxy (diisopropylamino)phosphinoxy]-1-[1-(S)-(4,4'-dimethoxytrityl)oxy-(3-propyl)]-3-(selected base, optionally protected)-2,5-dioxa-bicyclo[2.2.1]heptane (110-113)

Scheme 12

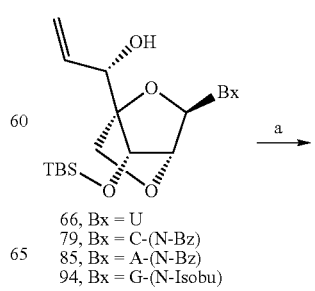

66, Bx = U
79, Bx = C-(N-Bz)
85, Bx = A-(N-Bz)
94, Bx = G-(N-Isobu)

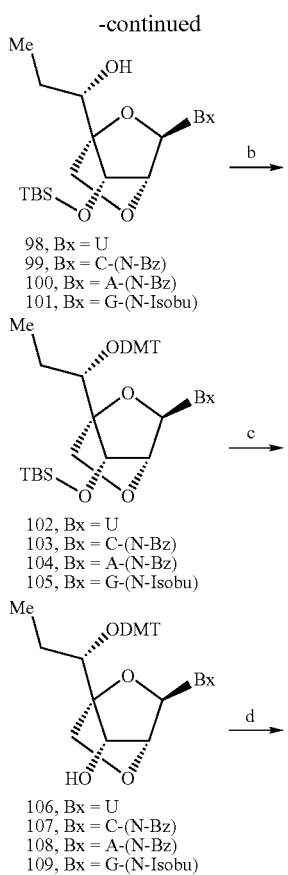

98, Bx = U
99, Bx = C-(N-Bz)
100, Bx = A-(N-Bz)
101, Bx = G-(N-Isobu)

102, Bx = U
103, Bx = C-(N-Bz)
104, Bx = A-(N-Bz)
105, Bx = G-(N-Isobu)

106, Bx = U
107, Bx = C-(N-Bz)
108, Bx = A-(N-Bz)
109, Bx = G-(N-Isobu)

110, Bx = U
111, Bx = C-(N-Bz)
112, Bx = A-(N-Bz)
113, Bx = G-(N-Isobu)

a Pd/C, H$_2$ balloon
b DMTCl, 2,6-lutidine, pyridine
c ET$_3$N•3HF, Et$_3$N, THF
d (iPr$_2$N)$_2$POCH$_2$CH$_2$CN, tetrazole, NMI, DMF A) Preparation of Compound 98

A mixture of Palladium on activated carbon (5 mg) and compound 66 (0.25 mmol, 0.10 g) in MeOH (2 mL) was hydrogenated using a hydrogen balloon. After 1 hour, the reaction was filtered through celite and the filter bed was washed with EtOAc. The solvents were evaporated under reduced pressure to provide 98, which was further dried under high vacuum and used without any purification.

B) Preparation of Compound 102

A solution of compound 98 (0.25 mmol, 0.1 g), DMTCl (0.63 mmol, 0.21 g) and 2,6-lutidine (0.63 mmol, 73 μL) in pyridine (1.25 mL) was heated at 45° C. for 7 days. The reaction was cooled to room temperature and diluted with EtOAc. The organic layer was washed with saturated sodium bicarbonate, brine, dried (Na$_2$SO$_4$) and concentrated under reduced pressure. Purification by column chromatography (SiO$_2$, eluting with 15 to 45% EtOAc in hexanes) provided compound 102 (0.10 g, 58%) as a white solid. 102 ($^1$H NMR (300 MHz, CDCl$_3$) δ: 9.1 (s, br, 1H), 8.26 (d, 1H, J=8.2), 7.42-7.20 (m, 9H), 6.84-6.78 (m, 4H), 5.69 (s, 1H), 5.66 (d, 1H, overlapped), 4.33 (s, 1H), 4.32 (s, 1H), 3.85 (d, 1H, J=7.5), 3.8 (s, 6H), 3.75 (d, 1H, J=7.5), 3.42 (d, 1H, J=8.2), 1.65 (m, 1H), 1.47 (m, 1H), 0.79 (s, 9H), 0.25 (t, 3H, J=7.5), 0.02 (s, 3H), −0.18 (s, 3H).

C) Preparation of Compound 110

Phosphoramidite compound 110 is prepared from compound 102 using the same general procedure described for the preparation of phosphoramidite compound 19a from compound 17a in example 1. Phosphoramidite Compounds 111-113 are prepared from nucleoside Compounds 79, 85 and 94. Hydrogenation of the double bond using catalytic Palladium on carbon and hydrogen provides Compounds 98-101 respectively. Protection of the 5' hydroxyl group as the dimethoxytrityl ether followed by removal of the silyl protecting group and a phosphitylation reaction (as described in example 1) provides phosphoramidite Compounds 110-113.

EXAMPLE 17

Preparation of Compounds 116a, 116b, 116c and 116d

Scheme 13

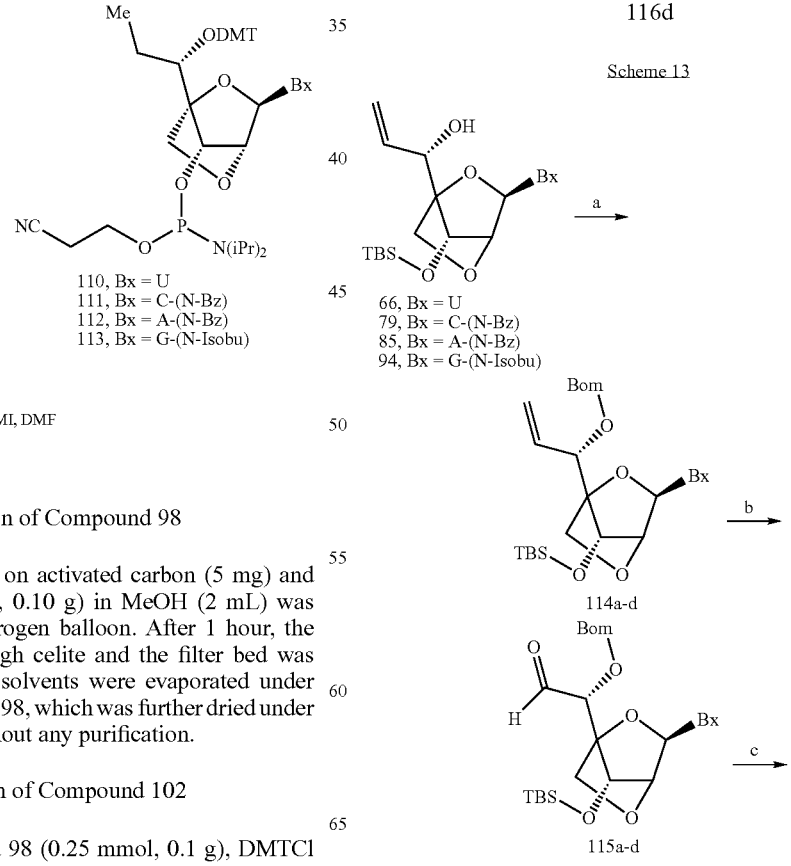

66, Bx = U
79, Bx = C-(N-Bz)
85, Bx = A-(N-Bz)
94, Bx = G-(N-Isobu)

114a-d 115a-d

-continued

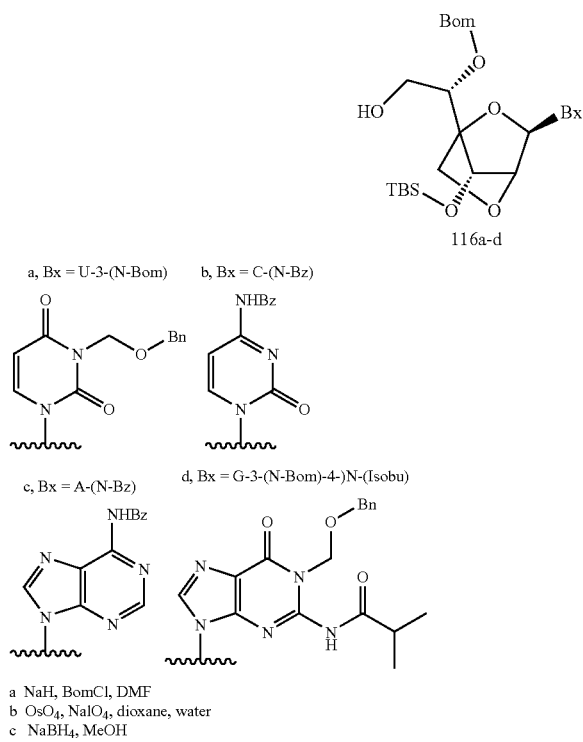

116a-d a, Bx = U-3-(N-Bom)   b, Bx = C-(N-Bz)
c, Bx = A-(N-Bz)   d, Bx = G-3-(N-Bom)-4-)N-(Isobu)

a NaH, BomCl, DMF
b OsO₄, NaIO₄, dioxane, water
c NaBH₄, MeOH

A) Preparation of Compound 114a

Sodium hydride (60%, 1.0 mmol, 40 mg) was added to a cold (0° C.) solution of Compound 66 (0.25 mmol, 0.10 g) and benzyloxymethyl chloride (BomCl, 0.75 mmol, 0.1 mL) in DMF (1 mL). After 1 hour, the reaction was quenched with water and diluted with EtOAc. The organic layer was then washed with water, brine, dried (Na$_2$SO$_4$) and concentrated. Purification of the residue by chromatography (SiO$_2$, 30% EtOAc in hexanes) provided Compound 114a (0.15 g, 93%) as a white solid.

B) Preparation of Compound 115a

A solution of osmium tetroxide (2.5% in isopropanol, 0.12 mL) was added to a mixture of Compound 114a (0.17 g, 0.11 g), sodium periodate (0.70 mmol, 0.15 g) and 2-6-lutidine (0.12 mL) in dioxane (2 mL) and water (0.5 mL). After stirring at room temperature for 36 h, the reaction was diluted with EtOAC and washed with water, 10% sodium thiosulfate, brine, dried (Na$_2$SO$_4$) and concentrated to provide crude Compound 115a, which was used without any further purification.

C) Preparation of Compound 116a

Sodium borohydride (25 mg) was added to a solution of crude Compound 115a (from above) in MeOH (1 mL). After stirring at room temperature for 1 hour, the reaction was diluted with EtOAc and the organic layer was washed with 10% HCl, saturated sodium bicarbonate, brine, dried (Na$_2$SO$_4$) and concentrated. Purification of the residue by chromatography (SiO$_2$, eluting with 50% EtOAc in hexanes) provided Compound 116a (73 mg, 65% from 115a) as an oil. 116a ($^1$H NMR (300 MHz, CDCl$_3$) δ: 7.69 (d, 1H, J=8.2), 7.49-7.24 (m, 10H), 5.77 (d, 1H, J=8.2), 5.61 (s, 1H), 5.47 (m, 2H), 4.98 (d, 1H, J=6.9), 4.84 (d, 1H, J=6.9), 4.80 (d, 1H, J=11.8), 4.69 (s, 2H), 4.66 (d, 1H, J=11.8), 4.29 (s, 1H), 4.03 (s, 1H), 3.96-3.79 (m, 3H), 3.67 (m, 1H), 3.22 (m, 1H), 0.87 (s, 9H), 0.07 (s, 3H), 0.04 (s, 3H).

D) Preparation of Compounds 116b-d

Reaction of Compounds 79, 85 and 94 with benzyloxymethyl chloride and sodium hydride provides nucleoside Compounds 114b-d respectively. Cleavage of the double bond with osmium tetroxide provides aldehydes Compounds 115b-d. Further reduction of the aldehyde functional group using sodium borohydride provides Compounds 116b-d respectively.

EXAMPLE 18

Preparation of Nucleosides 117a-d to 128a-d

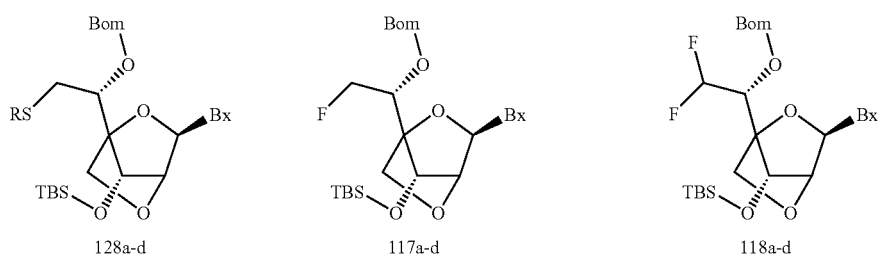

128a-d   117a-d   118a-d

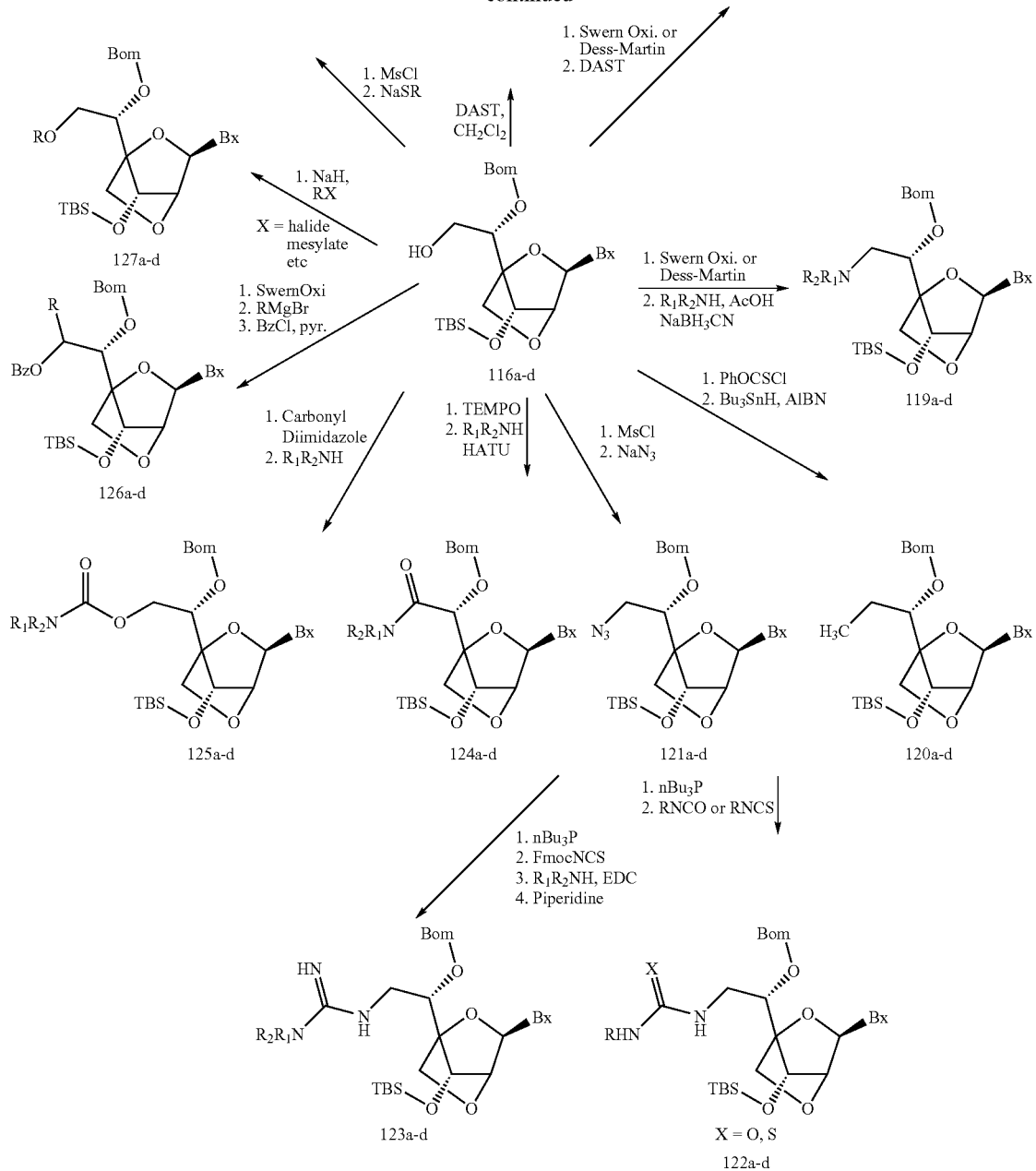

each R, R₁ and R₂ is a H or a substituent group

A) Preparation of Compound 127a (R=Me)

Sodium hydride (60%, 0.23 mmol, 9 mg) was added to a cold (0° C.) solution of Compound 116a (0.11 mmol, 73 mg), iodomethane (0.57 mmol, 40 μL) in DMF (0.25 mL). After stirring at 0° C. for 1 hour, the reaction was quenched with water and diluted with EtOAC. The organic layer was further washed with brine, dried ($Na_2SO_4$) and concentrated. Purification by chromatography ($SiO_2$, eluting with 20 to 40% EtOAc in hexanes) provided compound 127a (27 mg, 37%) as an oil. 127a ($^1$H NMR (300 MHz, $CDCl_3$) δ: 7.79 (d, 1H, J=8.2), 7.45-7.28 (m, 10H), 5.74 (d, 1H, J=8.2), 5.62 (s, 1H), 5.48 (m, 2H), 4.90 (m, 2H), 4.74 (d, 1H, J=11.9), 4.69 (s, 1H), 4.60 (s, 1H, J=11.9), 4.29 (s, 1H), 4.04 (s, 1H), 4.04 (m, 1H, overlapped), 3.99 (d, 1H, J=8.3), 3.84 (d, 1H, J=8.2), 3.72-3.48 (m, 2H), 3.35 (s, 3H), 0.87 (s, 9H), 0.07 (s, 3H), 0.04 (s, 3H).

B) Preparation of Compounds 117a-d through 123a-d

Compounds 117a-d are prepared from Compounds 116a-d by treatment with a fluorinating agent such as DAST using dichloromethane as the solvent. Compounds 118a-d are prepared from Compounds 116a-d by first oxidizing the primary hydroxyl group with Dess-Martin periodinane or under Swern conditions followed by treatment of the resulting aldehyde with DAST. Compounds 119a-d are prepared from Compounds 116a-d by first oxidizing the primary hydroxyl group with Dess-Martin periodinane or under Swern conditions followed by reductive amination of the resulting aldehyde with a primary or a secondary amine in the presence of glacial acetic acid and a reducing agent such as sodium cyanoborohydride. Compounds 120a-d are prepared from Compounds 116a-d by converting the hydroxyl group to a thiocarbonate derivative followed by a radical deoxygenation procedure using nBu$_3$SnH. Compounds 121a-d are prepared from Compounds 116a-d by converting the hydroxyl group to a leaving group (mesylate, tosylate, halide) followed by heating with excess sodium azide. Compounds 124a-d are prepared from Compounds 116a-d by oxidation of the primary alcohol to a carboxylic acid followed by reaction with a amine in the presence of HATU or any other peptide coupling reagent. Compounds 125a-b are prepared from Compounds 116a-d by activating the hydroxyl group with carbonyl diimidazole followed by reaction with a amine. Compounds 126a-d are prepared from Compounds 116a-d by oxidizing the primary alcohol under Swern or Dess-Martin conditions followed by reaction with a suitable organometallic reagent. Compounds 127b-d (127a prepared in section A, R=CH$_3$ above) are prepared from Compounds 116b-d by deprotonating the hydroxyl group with an appropriate base followed by quenching the anion with an alkylating reagent. Compounds 128a-d are prepared from Compounds 116a-d by converting the hydroxyl group to a leaving group followed by displacement with a thiol nucleophile. Compounds 122a-d are prepared from Compounds 121a-d by reduction of the azide group followed by reaction with an isocyanate or an isothiocyanate. Compounds 123a-d are prepared from Compounds 121a-d by reduction of the azido group and reaction with FmocNCS to provide an activated thiourea. Further reaction of the fmoc activated thiourea with an amine in the presence of EDC provides the substituted guanidine. Removal of the fmoc protecting group liberates Compounds 123a-d.

EXAMPLE 19

Preparation of Phosphoramidites 141-144

Scheme 15

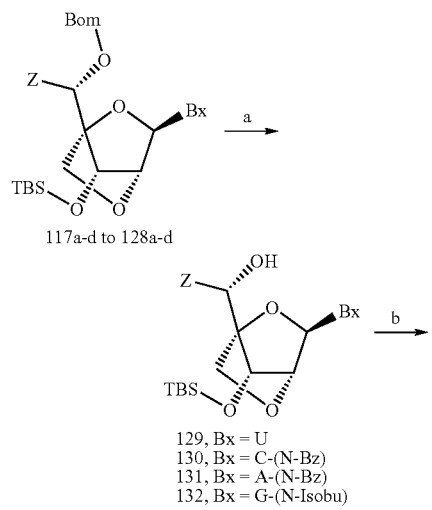

129, Bx = U
130, Bx = C-(N-Bz)
131, Bx = A-(N-Bz)
132, Bx = G-(N-Isobu)

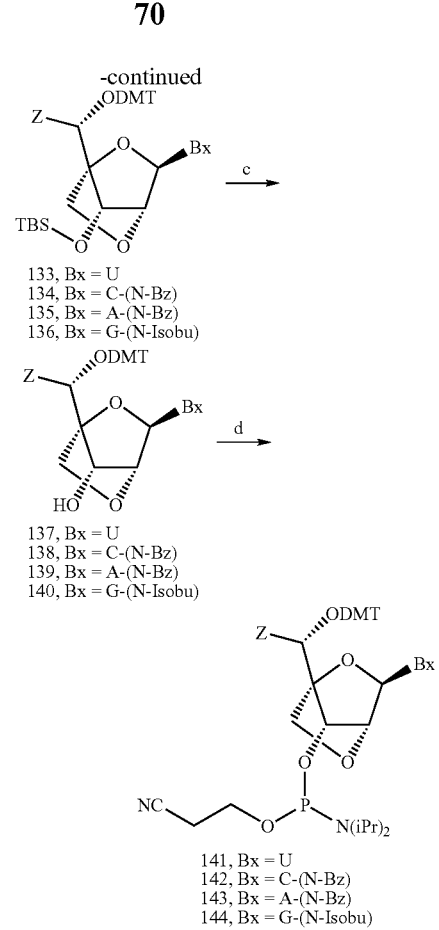

133, Bx = U
134, Bx = C-(N-Bz)
135, Bx = A-(N-Bz)
136, Bx = G-(N-Isobu)

137, Bx = U
138, Bx = C-(N-Bz)
139, Bx = A-(N-Bz)
140, Bx = G-(N-Isobu)

141, Bx = U
142, Bx = C-(N-Bz)
143, Bx = A-(N-Bz)
144, Bx = G-(N-Isobu)

a Pd/C, H$_2$
b DMTCl, 2,6-lutidine, pyridine
c Et$_3$N•3HF, Et$_3$N, THF
d (iPr$_2$N)$_2$POCH$_2$CH$_2$CN, tetrazole, NMI, DMF A) Preparation of Compound 129 (Z=CH$_2$OMe)

A mixture of Palladium on activated carbon (3 mg) and compound 127a (0.04 mmol, 27 mg) in MeOH (1 mL) was hydrogenated using a hydrogen balloon. After 24 hours, the reaction was filtered through celite and the filter bed was washed with EtOAc. The solvents were evaporated under reduced pressure and the residue was redissolved in MeOH (1 mL) and triethylamine (2 drops). After stirring at room temperature for 2 hours, the solvents were removed under reduced pressure to provide 129. 129 ($^1$H NMR (300 MHz, CDCl$_3$) δ: 7.89 (d, 1H, J=8.2), 5.75 (d, 1H, J=8.2), 5.63 (s, 1H), 4.22 (s, 1H), 4.17 (s, 1H), 4.08 (m, 1H), 3.98 (d, 1H, J=7.6), 3.71 (d, 1H, J=7.6), 3.60 (t, 1H, J=9.1), 3.44 (s, 3H), 3.42 (m, 1H, overlapped), 0.88 (s, 9H), 0.10 (s, 3H), 0.09 (s, 3H).

B) Preparation of Compound 141

Compound 129 is converted to phosphoramidite compound 141 using the same general procedures described for the preparation of phosphoramidite compound 19a from 16a in example 1

C) Preparation of Compounds 142-144

Compounds 130-132 are prepared by hydrogenation of the benzyloxymethyl protecting group using catalytic palladium on carbon and hydrogen gas. Protection of the 5' hydroxyl group as the dimethoxytrityl ether followed by removal of the silyl protecting group and a phosphitylation reaction (as described in example 1) provides phosphoramidite Compounds 142-144.

EXAMPLE 20

Preparation of Compounds 159 and 160

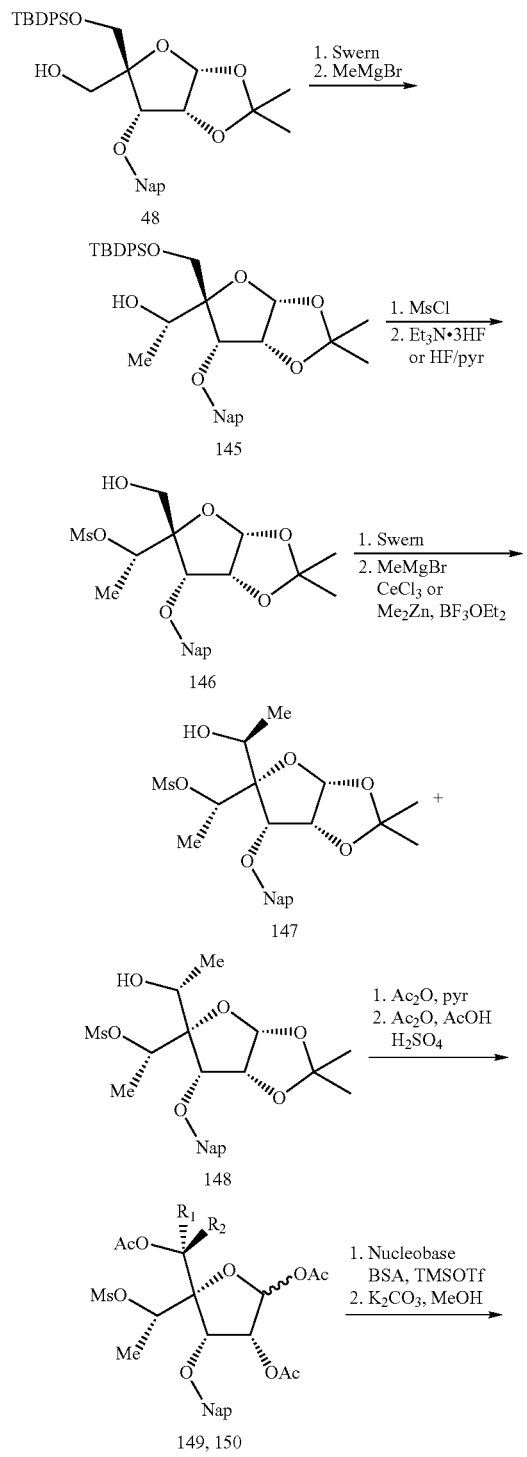

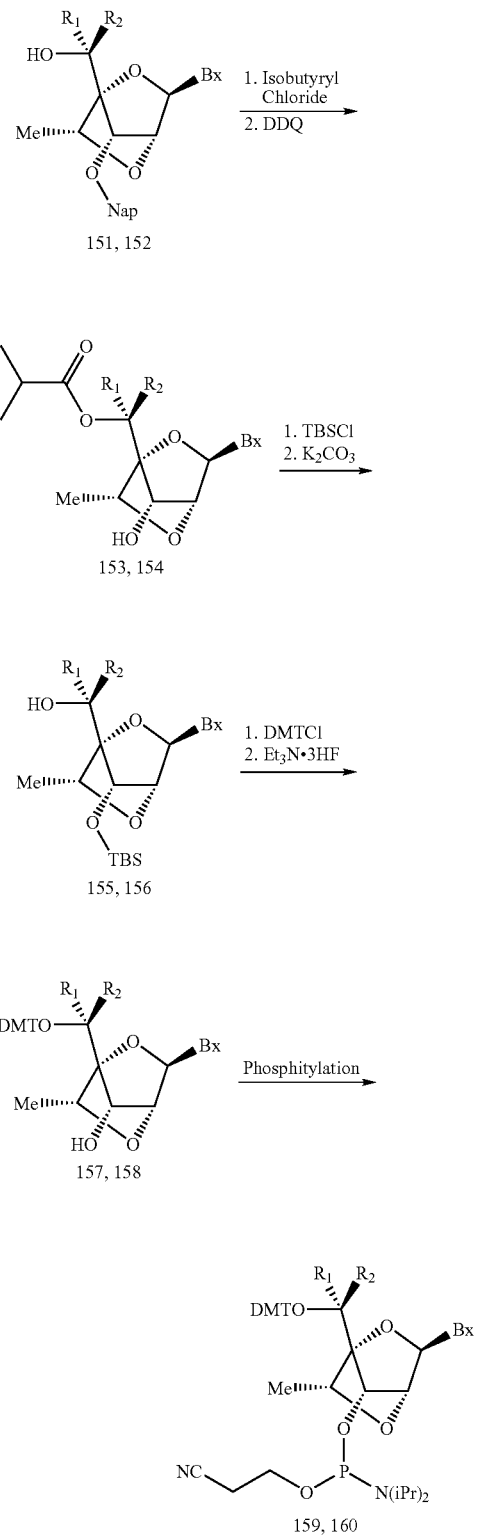

$R_1$ = Me, $R_2$ = H: 149, 151, 153, 155, 157, 159
$R_1$ = H, $R_2$ = Me: 150, 152, 154, 156, 158, 160

Compound 48 is prepared as per the procedures illustrated in Example 9.

EXAMPLE 21

Preparation of Compounds 175 and 176

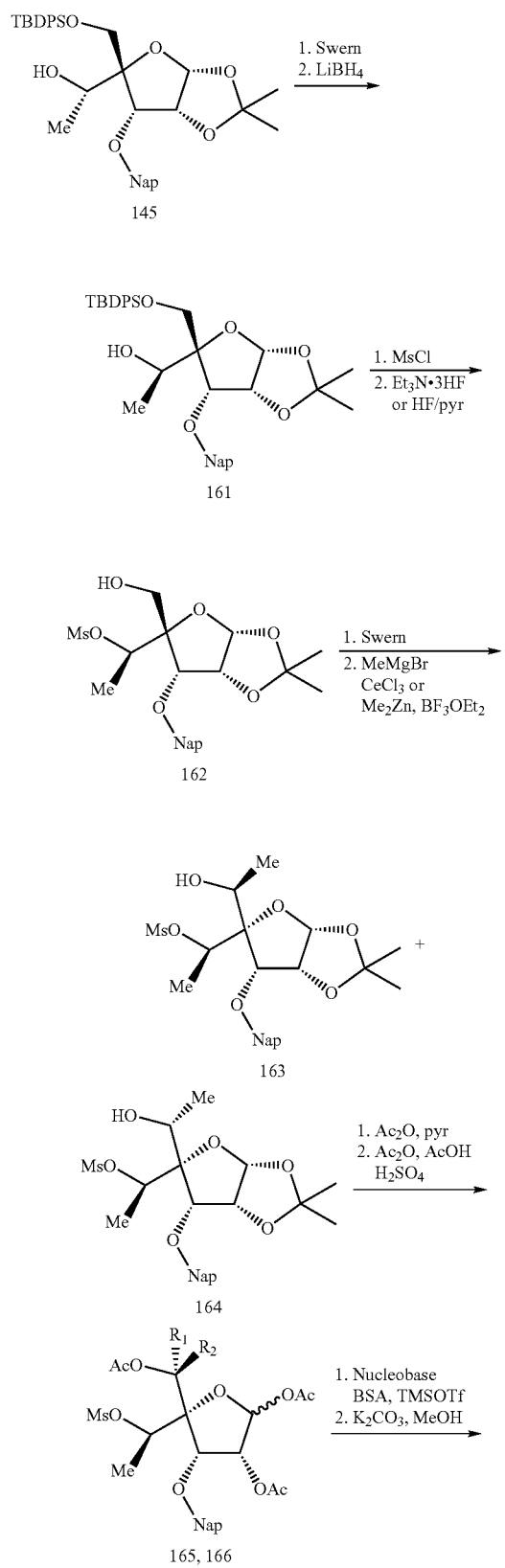

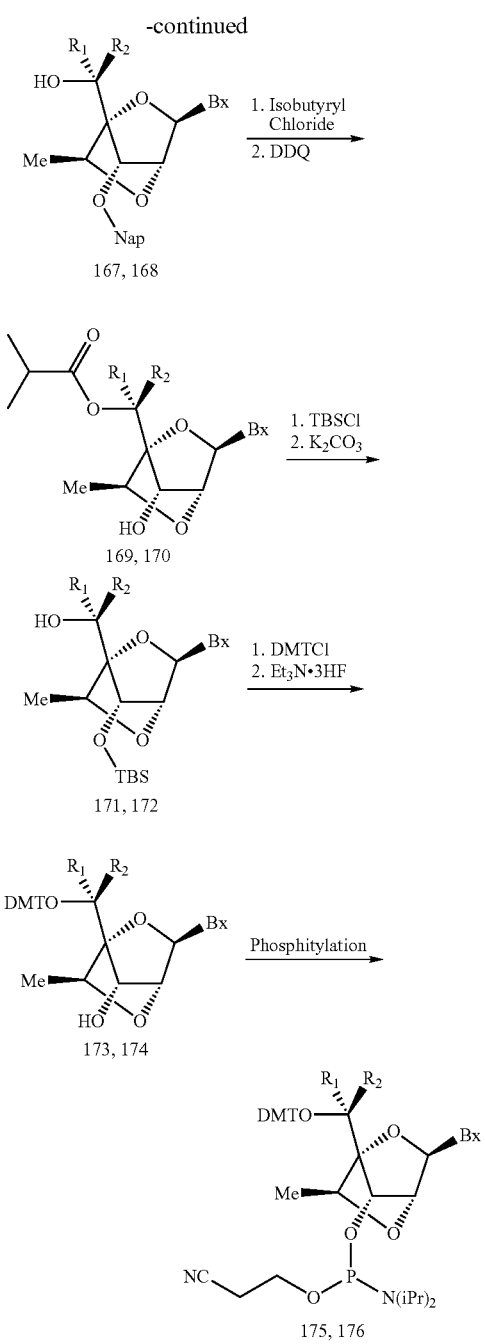

$R_1 = Me, R_2 = H$: 165, 167, 169, 171, 173, 175
$R_1 = H, R_2 = Me$: 166, 168, 170, 172, 174, 176

Compound 145 is prepared as per the procedures illustrated in Example 20.

EXAMPLE 22

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

EXAMPLE 23

Oligonucleotide and Oligonucleoside Synthesis

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides can be synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligonucleotides are recovered by precipitating with >3 volumes of ethanol from a 1 M $NH_4OAc$ solution. Phosphinate oligonucleotides can be prepared as described in U.S. Pat. No. 5,508,270.

Alkyl phosphonate oligonucleotides can be prepared as described in U.S. Pat. No. 4,469,863.

3'-Deoxy-3'-methylene phosphonate oligonucleotides can be prepared as described in U.S. Pat. No. 5,610,289 or 5,625,050.

Phosphoramidite oligonucleotides can be prepared as described in U.S. Pat. No. 5,256,775 or U.S. Pat. No. 5,366,878.

Alkylphosphonothioate oligonucleotides can be prepared as described in published PCT applications PCT/US94/00902 and PCT/US93/06976 (published as WO 94/17093 and WO 94/02499, respectively).

3'-Deoxy-3'-amino phosphoramidate oligonucleotides can be prepared as described in U.S. Pat. No. 5,476,925.

Phosphotriester oligonucleotides can be prepared as described in U.S. Pat. No. 5,023,243.

Borano phosphate oligonucleotides can be prepared as described in U.S. Pat. Nos. 5,130,302 and 5,177,198.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal linked oligonucleosides can be prepared as described in U.S. Pat. Nos. 5,264,562 and 5,264,564.

Ethylene oxide linked oligonucleosides can be prepared as described in U.S. Pat. No. 5,223,618.

EXAMPLE 24

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M $NH_4OAc$ with >3 volumes of ethanol. Synthesized oligonucleotides are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32+/−48). For some studies oligonucleotides are purified by HPLC, as described by Chiang et al., J. Biol. Chem. 1991, 266, 18162-18171. Results obtained with HPLC-purified material are generally similar to those obtained with non-HPLC purified material.

EXAMPLE 25

Oligonucleotide Synthesis

96 Well Plate Format

Oligonucleotides can be synthesized via solid phase P(III) phosphoramidite chemistry on an automated synthesizer capable of assembling 96 sequences simultaneously in a 96-well format. Phosphodiester internucleotide linkages are afforded by oxidation with aqueous iodine. Phosphorothioate internucleotide linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites are purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides are cleaved from support and deprotected with concentrated $NH_4OH$ at elevated temperature (55-60° C.) for 12-16 hours and the released product then dried in vacuo. The dried product is then re-suspended in sterile water to afford a master plate from which all analytical and test plate samples are then diluted utilizing robotic pipettors.

EXAMPLE 26

Oligonucleotide Analysis Using 96-Well Plate Format

The concentration of oligonucleotide in each well is assessed by dilution of samples and UV absorption spectroscopy. The full-length integrity of the individual products is evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

EXAMPLE 27

Cell Culture and Oligonucleotide Treatment

The effect of oligomeric compounds on target nucleic acid expression can be tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells were routinely cultured in DMEM, high glucose (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached approximately 90% confluence. Cells were seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

LIPOFECTIN™

When cells reached 65-75% confluency, they are treated with oligonucleotide. Oligonucleotide is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 µg/mL per 100 nM oligonucleotide. This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture is replaced with fresh culture medium. Cells are harvested 16-24 hours after oligonucleotide treatment.

Other suitable transfection reagents known in the art include, but are not limited to, CYTOFECTIN™, LIPOFECTAMINE™, OLIGOFECTAMINE™, and FUGENE™. Other suitable transfection methods known in the art include, but are not limited to, electroporation.

EXAMPLE 28

Analysis of Oligonucleotide Inhibition of a Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

EXAMPLE 29

Design of Phenotypic Assays and In Vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the a target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

EXAMPLE 30

RNA Isolation

Poly(A)+ mRNA Isolation

Poly(A)+ mRNA is isolated according to Miura et al., (Clin. Chem., 1996, 42, 1758-1764). Other methods for poly (A)+ mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 µL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

EXAMPLE 31

Real-Time Quantitative PCR Analysis of Target mRNA Levels

Quantitation of a target mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents were obtained from Invitrogen Life Technologies (Carlsbad, Calif.). RT, real-time PCR was carried out by adding 20 µL PCR cocktail (2.5×PCR buffer minus MgCl$_2$, 6.6 mM MgCl$_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

EXAMPLE 32

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 1).

```
Forward primer:
AATGGCTAAGTGAAGATGACAATCAT      (SEQ ID NO:2)

Reverse primer:
TGCACATATCATTACACCAGTTCGT       (SEQ ID NO:3)
```

And the PCR probe:

```
FAM-TTGCAGCAATTCACTGTAAAGCTGGAAAGG-   (SEQ ID NO:4)
TAMRA,
``` where FAM is the fluorescent dye and TAMRA is the quencher dye.

EXAMPLE 33

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

EXAMPLE 34

Preparation of Oligomeric Compounds

Following synthetic procedures well know in the art, some of which are illustrated herein, oligomeric compounds are prepared having at least one bis-modified bicyclic nucleoside having Formula III, using one or more of the phosphoramidite compounds 159, 160, 175 or 175 illustrated in Examples 20 and 21.

EXAMPLE 35

Nuclease Stability of 5'-(S) and (R)—CH$_3$—BNA Modified Oligomers Treated with SVPD The nuclease stability of 5'-CH$_3$—BNA modified oligomers was determined using snake venom phosphodiesterase (SVPD). Each oligomer was prepared as a 500 µL mixture containing: 5 µL 100 µM oligomer, 50 µL phosphodiesterase I @ 0.5 Units/mL in SVPD buffer (50 mM Tris-HcL, pH 7.5, 8 mM MgCl$_2$) final concentration 0.05 Units/mL, 445 µL SVP buffer. Samples were incubated at 37° C. in a water bath. Aliquots (100 µL) were taken at 0, 1, 2 and 4 days with fresh enzyme added at days 1 and 2. EDTA was added to aliquots immediately after removal to quench enzyme activity. Samples were analyzed on IP HPLC/MS.

| SEQ ID NO./ ISIS NO. | Composition (5' to 3') | % full length at day 4 |
|---|---|---|
| 05/392747 | C$_S$U$_S$TAGCACTGGCC$_S$U$_S$ | >80 |
| 05/392746 | C$_R$U$_R$TAGCACTGGCC$_R$U$_R$ | >80 |
| 05/392745 | C$_1$U$_1$TAGCACTGGCC$_1$U$_1$ | 40-50 |
| 05/392753 | C$_e$U$_e$TAGCACTGGCC$_e$U$_e$ | 30-40 |

All internucleoside linkages are phosphodiester, subscript S or R indicates the configuration at the 5' carbon atom for 5'-CH$_3$—BNA nucleosides which also have a 4'-CH$_2$—O-2' bridge group. A subscript e indicates 2'-O-MOE nucleosides and subscript 1 indicates 4'-CH$_2$—O-2' modified nucleosides. The 5-methyl substituted BNA-containing compounds (392746 and 392747) had a marked improvement over the unsubstituted BNA-containing compound (392745).

| SEQ ID NO./ ISIS NO. | % Composition at 24 hours | % Composition at 48 hours | % Composition at 96 hours |
|---|---|---|---|
| 05/392747 | 100% | 86% | 82% |
| 05/392746 | 100% | 90% | 84%. |
| 05/392745 | 67% | 56% | 48% |
| 05/392753 | 58% | 46% | 36%. |

EXAMPLE 36

Nuclease Stability of 5'-(S)—CH$_3$—BNA and 2'-O-MOE Modified Oligomers Treated with SVPD The nuclease stability of 5'-CH$_3$—BNA modified oligomers was determined using snake venom phosphodiesterase (SVPD). Each oligomer was prepared as a 90 µL mixture containing 5 µL oligomer (2 µL of 5 µM oligomer and 3 µL of 5' $^{32}$P-labeled oligomer) 75 µL H$_2$O, and 10 µL 10× buffer (500 mM Tris-HCl, 700 mM NaCl, and 140 mM MgCl$_2$ at pH 8.6). At time equals 0 min, 9 µL were removed from the oligomer sample prepared above and added to 10 µL stop buffer (6.67 M urea, 16.67% formamide and 83.3 mM EDTA) followed by 1 µL of H$_2$O and heated at 100° C. for 2.5 to 3 min. The kinetics of the assay began by the addition of 9 µL of SVPD (0.5 Units/mL). Final enzyme concentration was 0.05 Units/mL. Each aliquot of 10 µL of oligomer kinetics solution were added to 10 µL of stop buffer and heat deactivated as described above. Kinetic time points were taken at 1, 3, 9, 27, 80, 240 and 1290 min. Samples were analyzed by 12% acrylomide PAGE run for 2 hours at 45 Watts/gel.

| SEQ ID NO./ ISIS NO. | Composition (5' to 3') | modification |
|---|---|---|
| 06/395421 | TTTTTTTTTT$_e$T$_e$ | 2'-O-MOE |
| 07/395423 | TTTTTTTTTU$_1$U$_1$ | 4'-CH$_2$—O-2' |
| 07/395427 | TTTTTTTTTU$_S$U$_S$ | 5'-(S)—CH$_3$ BNA |
| 06/7157 | TTTTTTTTTTT | unmodified (2'-H) |

All internucleoside linkages are phosphodiester, subscript S indicates the configuration at the 5' carbon atom for 5'-CH$_3$—BNA nucleosides which also have a 4'-CH$_2$—O-2' bridge group, subscript e indicates 2'-O-MOE nucleosides and subscript 1 indicates 4'-CH$_2$—O-2' BNAs. All non subscripted T's are 2'-H. The 5-methyl substituted BNA-containing compound (395427) had a marked improvement over the unsubstituted BNA-containing compound (395423) and the MOE-containing compound (395421).

| SEQ ID NO. ISIS No. | % Comp. at 3 min. | % Comp. at 27 min. | % Comp. at 80 min. | % Comp. at 240 min. | % Comp. at 1290 min. |
|---|---|---|---|---|---|
| 06/395421 | 68.7 | 27.9 | 17.2 | 11.6 | 9.0 |
| 07/395423 | 32.6 | 4.7 | 2.5 | 2.2 | 2.2 |
| 07/395427 | 100.0 | 91.6 | 86.6 | 76.0 | 61.1 |
| 06/7157 | 5.2 | 1.2 | 2.0 | 1.7 | 0.9. |

EXAMPLE 37

5'-(S)—CH$_3$—BNA and 5'-(R)—CH$_3$—BNA 2-10-2 Gapped Oligomers Targeted to PTEN: In Vitro Study In accordance with the present invention, oligomeric compounds were synthesized and tested for their ability to reduce PTEN expression over a range of doses. b.END cells were treated with the 5'-CH$_3$—BNA modified oligomers at concentrations of 0.3125, 0.0625, 1.25, 2.5, 5, 10 or 20 nM using methods described herein. Expression levels of PTEN were determined using real-time PCR and normalized to RIBOGREEN™ as described in other examples herein. The percent reduction of PTEN mRNA relative to untreated control cells (% UTC) at a drug concentration of 20 nM is tabulated below. Resulting dose-response curves were used to determine the IC50 of 392747 as shown below. Tm's were assessed in 100 mM phosphate buffer, 0.1 mM EDTA, pH 7, at 260 nm using 4 µM 5'-CH$_3$—BNA modified oligomers and 4 µM complementary RNA.

| SEQ ID NO./ ISIS NO. | Composition (5' to 3') | % UTC | IC$_{50}$ | Tm ° C. |
|---|---|---|---|---|
| 05/392746 | C$_R$U$_R$TAGCACTGGCC$_R$U$_R$ | 75 | | 47.3 |
| 05/392747 | C$_S$U$_S$TAGCACTGGCC$_S$U$_S$ | 28 | 8.6 | 57.0 |

All internucleoside linkages are phosphorothioate and subscripts R and S indicate the configuration at the 5' carbon atom for 5'-CH$_3$—BNA nucleosides which also have a 4'-CH$_2$—O-2' bridge group.

EXAMPLE 38

5'-(S)—CH$_3$—BNA and 5'-(R)—CH$_3$—BNA 2-10-2 Gapped Oligomers Targeted to PTEN: In Vivo Study Six week old Balb/c mice (Jackson Laboratory, Bar Harbor, Me.) were injected twice weekly for 3 weeks with a 5'-CH$_3$—BNA modified oligomers (either 5'-(S) or 5'-(R)) targeted to PTEN at a dose of 0.5 or 2 μmol/kg. The mice were sacrificed 48 hours following the final administration. Liver tissues were homogenized and mRNA levels were quantitated using real-time PCR as described herein for comparison to untreated control levels (% UTC).

| SEQ ID NO./ ISIS NO. | Composition (5' to 3') | dose (μmol/kg) | % UTC |
|---|---|---|---|
| saline | | | 100 |
| 05/392746 | C$_R$U$_R$TAGCACTGGCC$_R$U$_R$ | 2.0 | 56 |
| 05/392746 | C$_R$U$_R$TAGCACTGGCC$_R$U$_R$ | 0.5 | 71 |
| 05/392747 | C$_S$U$_S$TAGCACTGGCC$_S$U$_S$ | 2.0 | 28 |
| 05/392747 | C$_S$U$_S$TAGCACTGGCC$_S$U$_S$ | 0.5 | 91 |

All internucleoside linkages are phosphorothioate and subscripts R and S indicates the configuration at the 5' carbon atom for 5'-CH$_3$—BNA nucleosides which also have a 4'-CH$_2$—O-2' bridge group.

EXAMPLE 39

5'-(S)—CH$_3$—BNA 2-10-2 Gapped Oligomers Targeted to PTEN: In Vivo Study

Six week old Balb/c mice (Jackson Laboratory, Bar Harbor, Me.) were injected once with a 5'-(S)—CH$_3$—BNA modified oligomer targeted to PTEN at a dose of 1, 2, 4 or 8 μmol/kg. The mice were sacrificed 72 hrs following administration. Liver tissues were homogenized and mRNA levels were quantitated using real-time PCR as described herein for comparison to untreated control levels (% UTC).

| SEQ ID NO./ ISIS NO. | Composition (5' to 3') | dose (μmol/kg) | % UTC |
|---|---|---|---|
| saline | | | 100 |
| 05/392747 | C$_S$U$_S$TAGCACTGGCC$_S$U$_S$ | 1 | 92 |
| 05/392747 | C$_S$U$_S$TAGCACTGGCC$_S$U$_S$ | 2 | 65 |
| 05/392747 | C$_S$U$_S$TAGCACTGGCC$_S$U$_S$ | 4 | 33 |
| 05/392747 | C$_S$U$_S$TAGCACTGGCC$_S$U$_S$ | 8 | 13 |

All internucleoside linkages are phosphorothioate and subscript S indicates the configuration at the 5' carbon atom for 5'-CH$_3$—BNA nucleosides which also have a 4'-CH$_2$—O-2' bridge group.

EXAMPLE 40

5'-(S)—CH$_3$—BNA and 2'-O-MOE Gapped Oligomers Targeted to PTEN in a Three-Week, Multiple Dose In Vivo Study Six week old Balb/c mice (Jackson Laboratory, Bar Harbor, Me.) were injected twice weekly for three weeks with 5'-(S)—CH$_3$—BNA (2-10-2, 14-mer), 4'-CH$_2$—O-2'-BNA (2-10-2, 14-mer) and 2'—O-MOE (5-10-5, 20-mer) modified oligomers targeted to PTEN at a dose of 3.2, 1.0, 0.32 and 0.1 μmol/kg (only the 3.2 and 1 μmol/kg data is shown below). The mice were sacrificed 48 hrs following last administration. Liver tissues were homogenized and mRNA levels were quantitated using real-time PCR as described herein for comparison to untreated control levels (% UTC). Plasma chemistries and liver weights were determined after sacrifice.

| SEQ ID NO./ ISIS NO. | Composition (5' to 3') | dose (μmol/kg) | % UTC | ALT |
|---|---|---|---|---|
| saline | | | | |
| 05/392747 | C$_S$U$_S$TAGCACTGGCC$_S$U$_S$ | 3.2 | 15 | 17.5 |
| 05/392747 | C$_S$U$_S$TAGCACTGGCC$_S$U$_S$ | 1 | 53 | 21.3 |
| 08/392063 | $^{Me}$C$_l$T$_l$TAGCACTGGC$^{Me}$C$_l$T$_l$ | 3.2 | 4.2 | 279.3 |
| 08/392063 | $^{Me}$C$_l$T$_l$TAGCACTGGC$^{Me}$C$_l$T$_l$ | 1 | 26 | 41.0 |
| 09/116847 | $^{Me}$C$_e$T$_e$G$_e$$^{Me}$C$_e$T$_e$AG$^{Me}$C$^{Me}$CT$^{Me}$CTGGAT$_e$T$_e$T$_e$G$_e$A$_e$ | 1 | 53 | 41.3 |

All internucleoside linkages are phosphorothioate, subscript S indicates the configuration at the 5' carbon atom for 5'-CH$_3$—BNA nucleosides which also have a 4'-CH$_2$—O-2' bridge group, subscript 1 indicates a 4'-CH$_2$—O-2' BNA, subscript e indicates a 2'-O-MOE and $^{Me}$C indicates a 5'-methyl cytosine nucleoside.

At the culmination of the study, animals in the high dose group showed significant increase in liver weights for the 4'-CH$_2$—O-2' BNA (392063, 3.2 μmol/Kg dose group) containing oligomers (153% relative to saline). In contrast, the liver weights for 5'-(S)—CH$_3$ BNA (392747, 3.2 μmol/Kg dose group) containing oligomers were 121% relative to saline. Liver weights for 2'-O-MOE containing oligomers (116847, 1.0 μmol/Kg dose group) were 116% relative to saline. This example demonstrates that the 5'-(S)—CH$_3$—BNA modification allows for the design of antisense oligomers which show a dramatic improvement in the ALT levels over the 4'-CH$_2$—O-2' BNA modified compounds.

EXAMPLE 41

5'(S)-Me-BNA and 4'-CH$_2$—O-2' BNA 2-10-2 Gapped Oligomers Targeted to PTEN: In Vivo Study Six week old Balb/c mice (Jackson Laboratory, Bar Harbor, Me.) were injected once with modified 5'-(S)—CH$_3$ (396569), 4'-CH$_2$—O-2' BNA 2-10-2 gapped oligomers targeted to PTEN at a dose of 2.5, 5, 10 and 20 μmol/kg (only 5 and 10 μmol/Kg data shown). The mice were sacrificed 66 hrs following administration. Liver tissues were homogenized.

| SEQ ID NO./ ISIS NO. | Composition (5' to 3') | dose (µmol/kg) | ALT |
|---|---|---|---|
| saline | | | 41.3 |
| 10/396569 | $U_S C_S$ATGGCTGCAGC$_S U_S$ | 10 | 111.0 |
| 10/396569 | $U_S C_S$ATGGCTGCAGC$_S U_S$ | 5 | 54.0 |
| 11/392056 | $T_l{}^{Me}C_l$ATGGCTGCAG$^{Me}C_l T_l$ | 10 | 925.0 |
| 11/392056 | $T_l{}^{Me}C_l$ATGGCTGCAG$^{Me}C_l T_l$ | 5 | 373.0 |

All internucleoside linkages are phosphorothioate, subscript S indicates the configuration at the 5' carbon atom for 5'-CH$_3$—BNA nucleosides which also have a 4'-CH$_2$—O-2' bridge group, subscript l indicates 4'-CH$_2$—O-2' nucleosides and $^{Me}$C indicates a 5'-methyl cytosine nucleoside.

For the above oligonucleotides, one (Isis No. 392056) does not include a nucleoside that is chiral at the 5' carbon atom, wherein the 396569 does. 396569 includes a 5'(S)-Me monomer and is clearly less toxic in the liver as compared to 392056 which does not have a substituent at the 5'-position.

EXAMPLE 42

5'(S)-Me-BNA, 2'-O-MOE and 4'-CH$_2$—O-2' BNA 2-14-2 Gapped Oligomers Targeted to PTEN: In Vivo Study Six week old Balb/c mice (Jackson Laboratory, Bar Harbor, Me.) were injected once with 5'-CH$_3$—BNA modified oligomers targeted to PTEN at a dose of 2 or 10 µmol/kg. The mice were sacrificed 72 hrs following administration. Liver tissues were homogenized and mRNA levels were quantitated using real-time PCR as described herein for comparison to untreated control levels (% UTC).

| SEQ ID NO./ ISIS NO. | Composition (5' to 3') | modification |
|---|---|---|
| 12/394420 | $^{Me}C_e T_e$GCTAGCCTCTGGATT$_e T_e$ | 2'-O-MOE |
| 12/394425 | $^{Me}C_l T_l$GCTAGCCTCTGGATT$_l T_l$ | 4'-CH2-O-2'BNA |
| 13/400521 | $C_S U_S$GCTAGCCTCTGGATU$_S U_S$ | 5'-(S)-CH$_3$ |

| ISIS NO. | dose (µmol/kg) | % UTC | ALT |
|---|---|---|---|
| saline | | 100% | 38.5 |
| 394420 | 2 | 79% | 30.3 |
| 394420 | 10 | 26% | 49.3 |
| 394425 | 2 | 11% | 41.2 |
| 394425 | 10 | 2.1% | 2453.2 |
| 400521 | 2 | 21.4% | 36.7 |
| 400521 | 10 | 3.8% | 152 |

All internucleoside linkages are phosphorothioate, subscripts R and S indicate the configuration at the 5' carbon atom for 5'-CH$_3$—BNA nucleosides which also have a 4'-CH$_2$—O-2' bridge group, subscript e indicates 2'-O-MOE nucleosides, subscript l indicates 4'-CH$_2$—O-2' nucleosides and $^{Me}$C indicates a 5'-methyl cytosine nucleoside.

At the high dose group (10 micromole/Kg), oligonucleotide 400521 containing the 5'(S)-Me modification is essentially equally efficacious as 394425. However, the ALT elevations for 400521 are modest (152) as compared to 394425 (2453.2) clearly indicating that the 5'-substitution results in a greatly improved therapeutic index.

EXAMPLE 43

6-(S)—CH$_3$—BNA and 6-(R)—CH$_3$—BNA 2-10-2 Gapped Oligomers Targeted to PTEN: In Vivo Study Six week old Balb/c mice (Jackson Laboratory, Bar Harbor, Me.) were injected twice weekly for 3 weeks with a 6-CH$_3$—BNA modified oligomers (either 6-(S) or 6-(R)) targeted to PTEN at a dose of 0.5 or 2 µmol/kg. The mice were sacrificed 48 hours following the final administration. Liver tissues were homogenized and mRNA levels were quantitated using real-time PCR as described herein for comparison to untreated control levels (% UTC).

| SEQ ID NO./ ISIS NO. | Composition (5' to 3') | dose (µmol/kg) | % UTC |
|---|---|---|---|
| saline | | | 100 |
| 05/392748 | $C_R U_R$TAGCACTGGCC$_R U_R$ | 2.0 | 31 |
| 05/392748 | $C_R U_R$TAGCACTGGCC$_R U_R$ | 0.5 | 81 |
| 05/392749 | $C_S U_S$TAGCACTGGCC$_S U_S$ | 2.0 | 23 |
| 05/392749 | $C_S U_S$TAGCACTGGCC$_S U_S$ | 0.5 | 73 |

All internucleoside linkages are phosphorothioate, bolded nucleosides are 6-CH$_3$—BNA nucleosides and subscripts R and S indicate the configuration at the 6 carbon atom.

EXAMPLE 44

6-(S)—CH$_3$—BNA and 6-(R)—CH$_3$—BNA 2-10-2 Gapped Oligomers Targeted to PTEN: In Vivo Study Six week old Balb/c mice (Jackson Laboratory, Bar Harbor, Me.) were injected once with 6-CH$_3$—BNA modified oligomers (either 6-(S) or 6-(R)) targeted to PTEN at a dose of 1, 2, 4 or 8 µmol/kg. The mice were sacrificed 72 hrs following administration. Liver tissues were homogenized and mRNA levels were quantitated using real-time PCR as described herein for comparison to untreated control levels (% UTC).

| SEQ ID NO./ ISIS NO. | Composition (5' to 3') | dose (µmol/kg) | % UTC |
|---|---|---|---|
| saline | | | 100 |
| 05/392748 | $C_R U_R$TAGCACTGGCC$_R U_R$ | 1 | 89 |
| 05/392748 | $C_R U_R$TAGCACTGGCC$_R U_R$ | 2 | 66 |
| 05/392748 | $C_R U_R$TAGCACTGGCC$_R U_R$ | 4 | 35 |
| 05/392748 | $C_R U_R$TAGCACTGGCC$_R U_R$ | 8 | 11 |

-continued

| SEQ ID NO./ ISIS NO. | Composition (5' to 3') | dose (µmol/kg) | % UTC |
|---|---|---|---|
| 05/392749 | C$_S$U$_S$TAGCACTGGCC$_S$U$_S$ | 1 | 75 |
| 05/392749 | C$_S$U$_S$TAGCACTGGCC$_S$U$_S$ | 2 | 51 |
| 05/392749 | C$_S$U$_S$TAGCACTGGCC$_S$U$_S$ | 4 | 25 |
| 05/392749 | C$_S$U$_S$TAGCACTGGCC$_S$U$_S$ | 8 | 9 |

All internucleoside linkages are phosphorothioate, bolded nucleosides are 6-CH$_3$—BNA nucleosides and subscripts S and R indicate the configuration at the 6 carbon atom.

EXAMPLE 45

6-(S)—CH$_3$—O—CH$_2$—BNA and 6-(R)—CH$_3$—O—CH$_2$—BNA 2-10-2 Gapped Oligomers Targeted to PTEN: In Vivo Study Six week old Balb/c mice (Jackson Laboratory, Bar Harbor, Me.) were injected once with 6-CH$_3$—BNA modified oligomers (either 6-(S) or 6-(R)) targeted to PTEN at a dose of 1, 2, 4 or 8 µmmol/kg (only the 8 mmol/kg data is shown below). The mice were sacrificed 72 hrs following administration. Liver tissues were homogenized and mRNA levels were quantitated using real-time PCR as described herein for comparison to untreated control levels (% UTC).

| SEQ ID NO./ ISIS NO. | Composition (5' to 3') | dose (µmol/kg) | % UTC |
|---|---|---|---|
| saline | | | 100 |
| 05/396004 | C$_R$U$_R$TAGCACTGGCC$_R$U$_R$ | 8 | 37 |
| 05/396005 | C$_S$U$_S$TAGCACTGGCC$_S$U$_S$ | 8 | 37 |

All internucleoside linkages are phosphorothioate, bolded and underlined nucleosides are 6-CH$_3$—O—CH$_2$—BNA nucleosides and subscripts S and R indicate the configuration at the 6 carbon atom.

EXAMPLE 46

Nuclease Stability of 6-(R or S)—CH$_3$—BNA Modified Oligomers Treated with SVPD The nuclease stability of 6-(R or S)—CH$_3$—BNA (392748 and 392749 respectively) modified oligomers was determined using snake venom phosphodiesterase (SVPD). The study included a the respective 6-unsubstituted gapmer (4'-CH$_2$—O-2' bridged BNA, 392745, subscript l) and the 2'-O-MOE gapmer (2'-O—(CH$_2$)$_2$—OCH$_3$, 392753, subscript e) for comparison. Each oligomer is prepared as a 500 µL mixture containing: 5 µL 100 µM oligomer, 50 µL phosphodiesterase I @ 0.5 Units/mL in SVPD buffer (50 mM Tris-HcL, pH 7.5, 8 mM MgCl$_2$) final concentration 0.05 Units/mL, 445 µL SVP buffer. Samples were incubated at 37° C. in a water bath. Aliquots (100 µL) were taken at 0, 1, 2 and 4 days with fresh enzyme added at days 1 and 2. EDTA was added to aliquats immediately after removal to quench enzyme activity. Samples were analyzed on IP HPLC/MS.

| SEQ ID NO./ ISIS NO. | Composition (5' to 3') | % full length at day 4 |
|---|---|---|
| 05/392748 | C$_R$U$_R$TAGCACTGGCC$_R$U$_R$ | >90 |
| 05/392749 | C$_S$U$_S$TAGCACTGGCC$_S$U$_S$ | >70 |
| 05/392745 | C$_l$U$_l$TAGCACTGGCC$_l$U$_l$ | >40 |
| 05/392753 | C$_e$U$_e$TAGCACTGGCC$_e$U$_e$ | >30 |

| SEQ ID NO./ ISIS NO. | % Composition at 24 hours | % Composition at 48 hours | % Composition at 96 hours |
|---|---|---|---|
| 05/392748 | 100% | 89% | 92% |
| 05/392749 | 96% | 84% | 74% |
| 05/392745 | 67% | 56% | 48% |
| 05/392753 | 58% | 46% | 36% |

All internucleoside linkages are phosphorothioate, bolded nucleosides are modified nucleosides, subscript R and S indicate the configuration at the 6 carbon atom for 6-CH$_3$—BNA nucleosides, subscript e indicates 2'-O-MOE nucleosides and subscript l indicates 4'-CH$_2$—O-2' modified nucleosides. The 6-methyl substituted BNA-containing compounds (392748 and 392749) had a marked improvement over the unsubstituted BNA-containing compound (392745).

EXAMPLE 47

Nuclease Stability of 6-(R or S)—CH$_3$—BNA, 4'-CH$_2$—O-2' BNA and 2'-O-MOE Modified Oligomers Treated with SVPD The nuclease stability of 6-CH$_3$—BNA modified oligomers was determined using snake venom phosphodiesterase (SVPD). Each oligomer is prepared as a 90 µL mixture containing 5 µL oligomer (2 µL of 5 µM oligomer and 3 µL of 5' $^{32}$P-labeled oligomer) 75 µL H$_2$O, and 10 µL 10× buffer (500 mM Tris-HCl, 700 mM NaCl, and 140 mM MgCl$_2$ at pH 8.6). At time equals 0 min, 9 µL were removed from the oligomer sample prepared above and added to 10 µL stop buffer (6.67 M urea, 16.67% formamide and 83.3 mM EDTA) followed by 1 µL of H$_2$O and heated at 100° C. for 2.5 to 3 min. The kinetics of the assay began by the addition of 9 µL of SVPD (0.5 Units/mL). Final enzyme concentration was 0.05 Units/mL. Each aliquot of 10 µL of oligomer kinetics solution were added to 10 µL of stop buffer and heat deactivated as described above. Kinetic time points were taken at 1, 3, 9, 27, 80, 240 and 1290 min. Samples were analyzed by 12% acrylomide PAGE run for 2 hours at 45 Watts/gel.

| SEQ ID NO./ ISIS NO. | Composition (5' to 3') | modification |
|---|---|---|
| 06/395421 | TTTTTTTTTT$_e$T$_e$ | Bold 2'-O-MOE |
| 07/395423 | TTTTTTTTTTU$_l$U$_l$ | Bold 4'-CH2-O-2' |
| 07/395424 | TTTTTTTTTTU$_R$U$_R$ | Bold 6-(R)-CH3 |

-continued

| SEQ ID NO./ ISIS NO. | Composition (5' to 3') | modification |
|---|---|---|
| 07/395425 | TTTTTTTTTU$_S$U$_S$ | Bold 6-(S)-CH |
| 06/7157 | TTTTTTTTTTT | unmodified (2'-H) |

All internucleoside linkages are phosphorothioate, bolded nucleosides are modified nucleosides, subscript R and S indicate the configuration at the 6 carbon atom for 6-CH$_3$—BNA nucleosides, subscript e indicates 2'-O-MOE nucleosides and subscript l indicates 4'-CH$_2$—O-2' modified nucleosides.

All internucleoside linkages are phosphorothioate, bolded nucleosides are modified positions, subscript s indicates 6-(S)—CH$_3$—BNA, subscript l indicates a 4'-CH$_2$—O-2' BNA, subscript e indicates a 2'-O-MOE and $^{Me}$C indicates a 5'-methyl cytosine nucleoside.

At the culmination of the study, animals in the high dose group showed significant increase in liver weights for the 4'-CH$_2$—O-2' BNA (392063, 3.2 µmol/Kg dose group) containing oligomers (153% relative to saline). In contrast, the liver weights for 6-(S)—CH$_3$ BNA (392749, 3.2 µmol/Kg dose group) containing oligomers were 117% relative to saline. Liver weights for 2'O-MOE containing oligomers (116847, 1.0 µmol/Kg dose group) were 116% relative to saline. This example demonstrates that the 6-(S)—CH$_3$—BNA modification allows for the design of antisense oligo-

| SEQ ID NO. ISIS No. | % Comp. at 3 min. | % Comp. at 27 min. | % Comp. at 80 min. | % Comp. at 240 min. | % Comp. at 1290 min. |
|---|---|---|---|---|---|
| 06/395421 | 68.7 | 27.9 | 17.2 | 11.6 | 9.0 |
| 07/395423 | 32.6 | 4.7 | 2.5 | 2.2 | 2.2 |
| 07/395424 | 96.4 | 89.1 | 83.2 | 79.0 | 72.0 |
| 07/395425 | 96.0 | 86.3 | 83.7 | 82.3 | 82.7 |
| 06/7157 | 5.2 | 1.2 | 2.0 | 1.7 | 0.9. |

EXAMPLE 48

6-(S)—CH$_3$—BNA, 4'-CH$_2$—O-2-BNA, and 2'-O-MOE Gapped Oligomers Targeted to PTEN in a Three-Week, Multiple Dose In Vivo Study Six week old Balb/c mice (Jackson Laboratory, Bar Harbor, Me.) were injected twice weekly for three weeks with 6-(S)—CH$_3$—BNA (2-10-2, 14-mer), 4'-CH$_2$—O-2'-BNA (2-10-2, 14-mer) and 2'-O-MOE (5-10-5, 20-mer) modified oligomers targeted to PTEN at a dose of 3.2, 1.0, 0.32 and 0.1 µmol/kg (only the 3.2 and 1 µmol/kg data is shown below). The mice were sacrificed 48 hrs following last administration. Liver tissues were homogenized and mRNA levels were quantitated using real-time PCR as described herein for comparison to untreated control levels (% UTC). Plasma chemistries and liver weights were determined after sacrifice.

mers which maintain the potency conferred by the 4'-CH$_2$—O-2' BNA with a dramatic improvement in the ALT levels over the 4'-CH$_2$—O-2' BNA modified compounds.

EXAMPLE 49

6-(R or S)—CH$_3$, 6-(R or S)—CH$_2$—OCH$_3$, 4'-CH$_2$—O-2' BNA 2-10-2 Gapped Oligomers Targeted to PTEN: In Vivo Study Six week old Balb/c mice (Jackson Laboratory, Bar Harbor, Me.) were injected once with modified 6-(R or S)—CH$_3$ (396568 and 396024 respectively), 6-(R or S)—CH$_2$—OCH$_3$ (396007 and 396008 respectively), 4'-CH$_2$—O-2' BNA 2-10-2 gapped oligomers targeted to PTEN at a dose of 2.5, 5, 10 and 20 µmol/kg (only 5 and 10 µmol/Kg data shown). The mice were sacrificed 66 hrs following administration. Liver tissues were homogenized.

| SEQ ID NO./ ISIS NO. | Composition (5' to 3') | dose (µmol/kg) | % UTC | ALT |
|---|---|---|---|---|
| saline | | | 100 | 41.3 |
| 05/392749 | C$_S$U$_S$TAGCACTGGCC$_S$U$_S$ | 3.2 | 4.3 | 29.8 |
| 05/392749 | C$_S$U$_S$TAGCACTGGCC$_S$U$_S$ | 1 | 36 | 24.5 |
| 08/392063 | $^{Me}$C$_l$T$_l$TAGCACTGGC$^{Me}$C$_l$T$_l$ | 3.2 | 4.2 | 279.3 |
| 08/392063 | $^{Me}$C$_l$T$_l$TAGCACTGGC$^{Me}$C$_l$T$_l$ | 1 | 26 | 41.0 |
| 09/116847 | $^{Me}$C$_e$T$_e$G$_e$$^{Me}$C$_e$T$_e$AG$^{Me}$C$^{Me}$CT $^{Me}$CTGGAT$_e$T$_e$T$_e$G$_e$A$_e$ | 1 | 53 | 41.3 |

| SEQ ID NO./ ISIS NO. | Composition (5' to 3') | dose (μmol/kg) | ALT | 6-Sub |
|---|---|---|---|---|
| saline | | | 41.3 | |
| 10/396024 | $U_SC_S$ATGGCTGCAGC$_S$U$_S$ | 10 | 250.5 | CH$_3$ |
| 10/396024 | $U_SC_S$ATGGCTGCAGC$_S$U$_S$ | 5 | 72.0 | CH$_3$ |
| 10/396568 | $U_RC_R$ATGGCTGCAGC$_R$U$_R$ | 10 | 234.3 | CH$_3$ |
| 10/396568 | $U_RC_R$ATGGCTGCAGC$_R$U$_R$ | 5 | 62.0 | CH$_3$ |
| 10/396008 | $U_SC_S$ATGGCTGCAGC$_S$U$_S$ | 10 | 129.5 | CH2-OCH$_3$ |
| 10/396008 | $U_SC_S$ATGGC103-118TGCAGC$_S$U$_S$ | 5 | 49.0 | CH2-OCH$_3$ |
| 10/396007 | $U_RC_R$ATGGCTGCAGC$_R$U$_R$ | 10 | 49.0 | CH2-OCH$_3$ |
| 10/396007 | $U_RC_R$ATGGCTGCAGC$_R$U$_R$ | 5 | 36.3 | CH2-OCH$_3$ |
| 11/392056 | $T_I{}^{Me}C_I$ATGGCTGCAG$^{Me}$C$_I$T$_I$ | 10 | 925.0 | n/a |
| 11/392056 | $T_I{}^{Me}C_I$ATGGCTGCAG$^{Me}$C$_I$T$_I$ | 5 | 373.0 | n/a |

All internucleoside linkages are phosphorothioate, bolded nucleosides are modified nucleosides, subscript R and S indicate the configuration at the 6 carbon atom for 6-CH$_3$—BNA (bolded only) and 6-CH$_2$—O—CH$_3$—BNA (bolded an underlined) nucleosides as indicated, subscript I indicates 4'-CH$_2$—O-2' nucleosides and $^{Me}$C indicates a 5'-methyl cytosine nucleoside.

EXAMPLE 50

2-14-2 Gapped Oligomers Targeted to PTEN: In Vivo Study

Six week old Balb/c mice (Jackson Laboratory, Bar Harbor, Me.) were injected once with 6-CH$_3$—BNA modified oligomers targeted to PTEN at a dose of 2 or 10 μmol/kg. The mice were sacrificed 72 hrs following administration. Liver tissues were homogenized and mRNA levels were quantitated using real-time PCR as described herein for comparison to untreated control levels (% UTC).

| SEQ ID NO./ ISIS NO. | Composition (5' to 3') | modification |
|---|---|---|
| 12/394420 | $^{Me}$C$_e$T$_e$GCTAGCCTCTGGATT$_e$T$_e$ | Bold 2'-O-MOE |
| 13/400522 | C$_R$U$_R$GCTAGCCTCTGGATU$_R$U$_R$ | Bold 6-(R)-CH$_3$ |
| 13/400523 | C$_S$U$_S$GCTAGCCTCTGGATU$_S$U$_S$ | Bold 6-(S)-CH$_3$ |
| 13/400524 | C$_R$U$_R$GCTAGCCTCTGGATU$_R$U$_R$ | Bold 6-(R)-CH$_2$-O-CH$_3$ |
| 13/400525 | C$_S$U$_S$GCTAGCCTCTGGATU$_S$U$_S$ | Bold 6-(S)-CH$_2$-O-CH$_3$ |

| ISIS NO. | dose (μmol/kg) | % UTC | Standard deviation |
|---|---|---|---|
| saline | | 100% | 12% |
| 394420 | 2 | 79% | 2% |
| 394420 | 10 | 26% | 11% |
| 400522 | 2 | 18% | 3% |
| 400522 | 10 | 4% | 0% |
| 400523 | 2 | 17% | 2% |
| 400523 | 10 | 4% | 1% |
| 400524 | 2 | 23% | 7% |
| 400524 | 10 | 4% | 0% |
| 400525 | 2 | 21% | 3% |
| 400525 | 10 | 3% | 0% |

All internucleoside linkages are phosphorothioate, bolded nucleosides are modified nucleosides, subscript R and S indicate the configuration at the 6 carbon atom for 6-CH$_3$—BNA and 6-CH$_2$—O—CH$_3$—BNA nucleosides as indicated, subscript e indicates 2'-O-MOE nucleosides and $^{Me}$C indicates a 5'-methyl cytosine nucleoside.

EXAMPLE 51

5'-Vinyl and LNA 2-14-2 Gapped Oligomers Targeted to PTEN: In Vivo Study

Six week old Balb/c mice (Jackson Laboratory, Bar Harbor, Me.) were injected once with one of the modified oligomers listed below targeted to PTEN at a dose of 1.9, 6, 19 or 60 mg/kg for the 18mers (411027 and 394425) or 3.2, 10, 32 or 100 mg/kg for the 14mers (425-452, 392063 and 410129). The mice were sacrificed 64 hrs following administration. Liver tissues were homogenized and mRNA levels were quantitated using real-time PCR as described herein for comparison to untreated control levels (% UTC). Data for oligomers 425-452 and 392063 were obtained in one assay. Data for oligomers 410129 and 411027 were obtained in another assay. The data for 394425 was obtained in a separate assay but has been repeated and has been consistent. The modified nucleosides in the wings for the LNA gapped oligomers are 5-methylated whereas the modified nucleosides in the wings of other modified oligomers are not 5-methylated.

| SEQ ID NO/ ISIS NO | Sequence | PTEN % UTC (mg/kg dose) | | | |
|---|---|---|---|---|---|
| | | 3.2 | 10 | 32 | 100 |
| saline (not dosed, 100% UTC) | | | | | |
| 05/425452 | C$_l$U$_l$TAGCACTGGCC$_l$U$_l$ | 93 | 80 | 36 | 7 |
| 08/392063 | $^{Me}$C$_l$T$_l$TAGCACTGGC$^{Me}$C$_l$T$_l$ | 92 | 29 | 36 | 7 |
| 05/410129 | C$_v$U$_v$TAGCACTGGCC$_v$U$_v$ | 100 | 75 | 31 | 7 |
| | | 1.9 | 60 | 19 | 60 |
| 13/411027 | C$_v$U$_v$GCTAGCCTCTGGATU$_v$U$_v$ | 89 | 61 | 24 | 7 |
| 12/394425 | $^{Me}$C$_l$G$_l$GCTAGCCTCTGGATT$_l$T$_l$ | 100 | 35 | 8 | 4 |

Wherein the annotated nucleosides are illustrated below:

subscript i

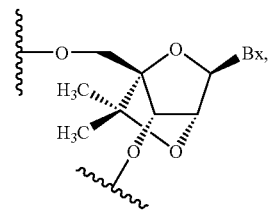

subscript l

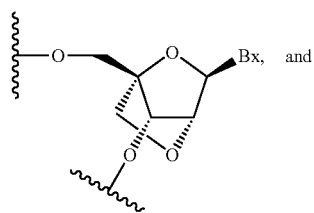, and subscript v

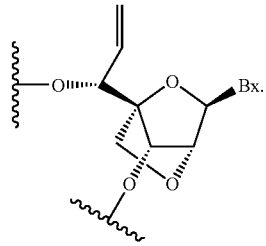

All internucleoside linkages are phosphorothioate, superscript Me preceding a C indicates that the cytosine is a 5-(S)-methyl cytosine and all nucleosides not otherwise annotated are β-D-2'-deoxyribonucleosides.

| SEQ ID NO./ ISIS NO. | Tm | ED$_{50}$ (mg/kg) | ALT IU/L) | | | |
|---|---|---|---|---|---|---|
| | | | 3.2 | 10 | 32 | 100 |
| 05/425452 | 56.3° C. | 20.8 | 26 | 28 | 23 | 22.5 |
| 08/392063 | 60.5° C. | 7.0 | 9.5 | 12.5 | 9.75 | 18670 |
| 05/410129 | 52.9° C. | 18.5 | 35 | 33 | 30 | 27 |
| 13/411027 | 59.9° C. | 7.4 | 26 | 40 | 27 | 38 |
| 12/394425 | 61.6° C. | 4.4 | 31 | 28 | 55 | 1445 |

The Tm for the three 14mers (425-452, 392063 and 410129) was determined by melting against the RNA 14mer (394098) complement and the Tm for the two 18mers (392063 and 394425) was determined by melting against the RNA 20mer (131566) which has a 14 base complementary region to the 18mers.

| SEQ ID NO./ ISIS NO. | RNA Sequence (5' to 3') |
|---|---|
| 14/131566 | UCAAAUCCAGAGGCUAGCAG |
| 15/394098 | AGGCCAGUGCUAAG. |

What is claimed is:

1. A bicyclic nucleoside having Formula I:

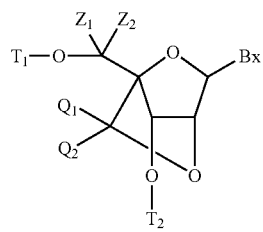

wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

one of $Z_1$ and $Z_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other one of $Z_1$ and $Z_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

one of $Q_1$ and $Q_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol and the other one of $Q_1$ and $Q_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol;

or $Q_1$ and $Q_2$ together are methylene (=$CH_2$);

each substituted group is mono or poly substituted with substituent groups independently selected from halogen, $OJ_1$, $SJ_1$, $NJ_1J_2$, $N_3$, $COOJ_1$, CN, O—C(=O)$NJ_1J_2$, N(H)C(=NH)$NJ_1J_2$, N(H)C(=O)N(H)$J_2$ or N(H)C(=S)N(H)$J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

2. The bicyclic nucleoside of claim 1 wherein $Z_1$ and $Z_2$ are each, independently, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl.

3. The bicyclic nucleoside of claim 2 wherein $Z_1$ and $Z_2$ are each $CH_3$.

4. The bicyclic nucleoside of claim 1 wherein one of $Z_1$ and $Z_2$ is H.

5. The bicyclic nucleoside of claim 4 wherein the other one of $Z_1$ and $Z_2$ is substituted $C_1$-$C_6$ alkyl.

6. The bicyclic nucleoside of claim 5 wherein the other one of $Z_1$ and $Z_2$ is $CH_2F$, $CHF_2$ or $CF_3$.

7. The bicyclic nucleoside of claim 4 wherein the other one of $Z_1$ and $Z_2$ is $C_1$-$C_6$ alkyl.

8. The bicyclic nucleoside of claim 7 wherein the other one of $Z_1$ and $Z_2$ is $CH_3$.

9. The bicyclic nucleoside of claim 1 wherein $Q_1$ and $Q_2$ are each, independently, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol.

10. The bicyclic nucleoside of claim 9 wherein $Q_1$ and $Q_2$ are each $CH_3$.

11. The bicyclic nucleoside of claim 1 wherein one of $Q_1$ and $Q_2$ is H.

12. The bicyclic nucleoside of claim 11 wherein the other one of $Q_1$ and $Q_2$ is substituted $C_1$-$C_6$ alkyl.

13. The bicyclic nucleoside of claim 12 wherein the other one of $Q_1$ and $Q_2$ is $CH_2F$, $CHF_2$ or $CF_3$.

14. The bicyclic nucleoside of claim 11 wherein the other one of $Q_1$ and $Q_2$ is $C_1$-$C_6$ alkyl.

15. The bicyclic nucleoside of claim 14 wherein the other one of $Q_1$ and $Q_2$ is $CH_3$.

16. The bicyclic nucleoside of claim 1 wherein $Q_1$ and $Q_2$ together are methylene (=$CH_2$).

17. The bicyclic nucleoside of claim 16 wherein one of $Z_1$ and $Z_2$ is $CH_3$ and the other one of $Z_1$ and $Z_2$ is H.

18. The bicyclic nucleoside of claim 1 having Formula II:

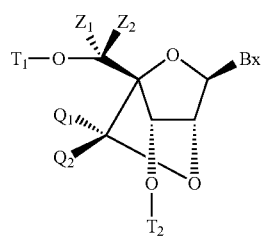

II wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;
one of $Z_1$ and $Z_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other one of $Z_1$ and $Z_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
one of $Q_1$ and $Q_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol and the other one of $Q_1$ and $Q_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, thiol or substituted thiol;
or $Q_1$ and $Q_2$ together are methylene (=$CH_2$);
each substituted group is mono or poly substituted with substituent groups independently selected from halogen, $OJ_1$, $SJ_1$, $NJ_1J_2$, $N_3$, $COOJ_1$, CN, O—C(=O)$NJ_1J_2$, N(H)C(=NH)$NJ_1J_2$, N(H)C(=O)N(H)$J_2$ or N(H)C(=S)N(H)$J_2$; and
each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

19. The bicyclic nucleoside of claim 18 wherein $Z_2$ and $Q_2$ are each H.

20. The bicyclic nucleoside of claim 19 wherein $Z_1$ and $Q_1$ are each $CH_3$.

21. The bicyclic nucleoside of claim 18 wherein $Z_2$ and $Q_1$ are each H.

22. The bicyclic nucleoside of claim 21 wherein $Z_1$ and $Q_2$ are each $CH_3$.

23. The bicyclic nucleoside of claim 18 wherein $Z_1$ and $Q_2$ are each H.

24. The bicyclic nucleoside of claim 23 wherein $Z_2$ and $Q_1$ are each $CH_3$.

25. The bicyclic nucleoside of claim 18 wherein $Z_1$ and $Q_1$ are each H.

26. The bicyclic nucleoside of claim 25 wherein $Z_2$ and $Q_2$ are each $CH_3$.

27. The bicyclic nucleoside of claim 1 wherein Bx is uracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4-benzoxazin-2(3H)-one), 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',2':4,5]pyrrolo[2,3-d]pyrimidin-2-one.

28. The bicyclic nucleoside of claim 27 wherein Bx is uracil, thymine, cytosine, 5-methyl-cytosine, 2,6-diaminopurine, adenine or guanine.

29. The bicyclic nucleoside of claim 1 wherein $T_1$ is selected from acetyl, benzyl, t-butyl-dimethylsilyl, t-butyl-diphenylsilyl and dimethoxytrityl.

30. The bicyclic nucleoside of claim 1 wherein $T_1$ is 4,4'-dimethoxytrityl.

31. The bicyclic nucleoside of claim 1 wherein $T_2$ is a reactive phosphorus group selected from diisopropylcyanoethoxy phosphoramidite or H-phosphonate.

32. The bicyclic nucleoside claim 31 wherein $T_1$ is 4,4'-dimethoxytrityl and $T_2$ is diisopropyl-cyanoethoxy phosphoramidite.

33. An oligomeric compound having at least one bicyclic nucleoside of Formula III:

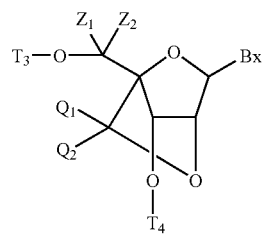

III wherein independently for each bicyclic nucleoside having Formula III:
Bx is a heterocyclic base moiety;
$T_3$ and $T_4$ are each, independently, an internucleoside linking group linking the bicyclic nucleoside of Formula III to the oligomeric compound or one of $T_3$ and $T_4$ is an internucleoside linking group linking the bicyclic nucleoside of Formula III to the oligomeric compound and the other of $T_3$ and $T_4$ is H, a hydroxyl protecting group, a linked conjugate group or a 5' or 3'-terminal group;
one of $Z_1$ and $Z_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other one of $Z_1$ and $Z_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

one of Q$_1$ and Q$_2$ is H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, thiol or substituted thiol and the other one of Q$_1$ and Q$_2$ is C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, thiol or substituted thiol;

or Q$_1$ and Q$_2$ together are methylene (=CH$_2$);

each substituted group is mono or poly substituted with substituent groups independently selected from halogen, OJ$_1$, SJ$_1$, NJ$_1$J$_2$, N$_3$, COOJ$_1$, CN, O—C(=O)NJ$_1$J$_2$, N(H)C(=NH)NJ$_1$J$_2$, N(H)C(=O)N(H)J$_2$ or N(H)C(=S)N(H)J$_2$; and each J$_1$ and J$_2$ is, independently, H, C$_1$-C$_6$ alkyl, C$_2$-C$_6$ alkenyl, C$_2$-C$_6$ alkynyl, C$_1$-C$_6$ aminoalkyl or a protecting group.

34. The oligomeric compound of claim 33 wherein Z$_1$ and Z$_2$ are each, independently, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl or substituted C$_2$-C$_6$ alkynyl for essentially each bicyclic nucleoside having Formula III.

35. The oligomeric compound of claim 34 wherein Z$_1$ and Z$_2$ are each CH$_3$ for essentially each bicyclic nucleoside having Formula III.

36. The oligomeric compound of claim 33 wherein one of Z$_1$ and Z$_2$ is H for essentially each bicyclic nucleoside having Formula III.

37. The oligomeric compound of claim 36 wherein the other one of Z$_1$ and Z$_2$ is substituted C$_1$-C$_6$ alkyl for essentially each bicyclic nucleoside having Formula III.

38. The oligomeric compound of claim 37 wherein the other one of Z$_1$ and Z$_2$ is CH$_2$F, CHF$_2$ or CF$_3$ for essentially each bicyclic nucleoside having Formula III.

39. The oligomeric compound of claim 36 wherein the other one of Z$_1$ and Z$_2$ is C$_1$-C$_6$ alkyl for essentially each bicyclic nucleoside having Formula III.

40. The oligomeric compound of claim 39 wherein the other one of Z$_1$ and Z$_2$ is CH$_3$ for essentially each bicyclic nucleoside having Formula III.

41. The oligomeric compound of claim 33 wherein Q$_1$ and Q$_2$ are each, independently, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, thiol or substituted thiol for essentially each bicyclic nucleoside having Formula III.

42. The oligomeric compound of claim 41 wherein Q$_1$ and Q$_2$ are each CH$_3$ for essentially each bicyclic nucleoside having Formula III.

43. The oligomeric compound of claim 33 wherein one of Q$_1$ and Q$_2$ is H for essentially each bicyclic nucleoside having Formula III.

44. The oligomeric compound of claim 43 wherein the other one of Q$_1$ and Q$_2$ is substituted C$_1$-C$_6$ alkyl for essentially each bicyclic nucleoside having Formula III.

45. The oligomeric compound of claim 44 wherein the other one of Q$_1$ and Q$_2$ is CH$_2$F, CHF$_2$ or CF$_3$ for essentially each bicyclic nucleoside having Formula III.

46. The oligomeric compound of claim 43 wherein the other one of Q$_1$ and Q$_2$ is C$_1$-C$_6$ alkyl for essentially each bicyclic nucleoside having Formula III.

47. The oligomeric compound of claim 46 wherein the other one of Q$_1$ and Q$_2$ is CH$_3$ for essentially each bicyclic nucleoside having Formula III.

48. The oligomeric compound of claim 33 wherein Q$_1$ and Q$_2$ together are methylene (=CH$_2$) for essentially each bicyclic nucleoside having Formula III.

49. The oligomeric compound of claim 48 wherein one of Z$_1$ and Z$_2$ is CH$_3$ and the other one of Z$_1$ and Z$_2$ is H for essentially each bicyclic nucleoside having Formula III.

50. The oligomeric compound of claim 33 having Formula IV:

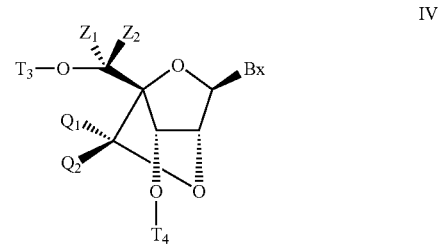

wherein independently for each bicyclic nucleoside having Formula IV:

Bx is a heterocyclic base moiety;

T$_3$ and T$_4$ are each, independently, an internucleoside linking group linking the bicyclic nucleoside of Formula IV to the oligomeric compound or one of T$_3$ and T$_4$ is an internucleoside linking group linking the bicyclic nucleoside of Formula IV to the oligomeric compound and the other of T$_3$ and T$_4$ is H, a hydroxyl protecting group, a linked conjugate group or a 5' or 3'-terminal group;

one of Z$_1$ and Z$_2$ is H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl or substituted C$_2$-C$_6$ alkynyl and the other one of Z$_1$ and Z$_2$ is C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl or substituted C$_2$-C$_6$ alkynyl;

one of Q$_1$ and Q$_2$ is H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, thiol or substituted thiol and the other one of Q$_1$ and Q$_2$ is C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, thiol or substituted thiol;

or Q$_1$ and Q$_2$ together are methylene (=CH$_2$);

each substituted group is mono or poly substituted with substituent groups independently selected from halogen, OJ$_1$, SJ$_1$, NJ$_1$J$_2$, N$_3$, COOJ$_1$, CN, O—C(=O)NJ$_1$J$_2$, N(H)C(=NH)NJ$_1$J$_2$, N(H)C(=O)N(H)J$_2$ or N(H)C(=S)N(H)J$_2$; and each J$_1$ and J$_2$ is, independently, H, C$_1$-C$_6$ alkyl, C$_2$-C$_6$ alkenyl, C$_2$-C$_6$ alkynyl, C$_1$-C$_6$ aminoalkyl or a protecting group.

51. The oligomeric compound of claim 50 wherein Z$_2$ and Q$_2$ are each H for essentially each bicyclic nucleoside having Formula IV.

52. The oligomeric compound of claim 51 wherein Z$_1$ and Q$_1$ are each CH$_3$ for essentially each bicyclic nucleoside having Formula IV.

53. The oligomeric compound of claim 50 wherein Z$_2$ and Q$_1$ are each H for essentially each bicyclic nucleoside having Formula IV.

54. The oligomeric compound of claim 53 wherein Z$_1$ and Q$_2$ are each CH$_3$ for essentially each bicyclic nucleoside having Formula IV.

55. The oligomeric compound of claim 50 wherein Z$_1$ and Q$_2$ are each H for essentially each bicyclic nucleoside having Formula IV.

56. The oligomeric compound of claim 55 wherein Z$_2$ and Q$_1$ are each CH$_3$ for essentially each bicyclic nucleoside having Formula IV.

57. The oligomeric compound of claim 50 wherein $Z_1$ and $Q_1$ are each H for essentially each bicyclic nucleoside having Formula IV.

58. The oligomeric compound of claim 57 wherein $Z_2$ and $Q_2$ are each $CH_3$ for essentially each bicyclic nucleoside having Formula IV.

59. The oligomeric compound of claim 33 wherein Bx is uracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4-benzoxazin-2(3H)-one),1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',2':4,5]pyrrolo[2,3-d]pyrimidin-2-one for essentially each bicyclic nucleoside having Formula IV.

60. The oligomeric compound of claim 59 wherein Bx is uracil, thymine, cytosine, 5-methyl-cytosine, 2,6-diaminopurine, adenine or guanine for essentially each bicyclic nucleoside having Formula IV.

61. The oligomeric compound of claim 33 wherein each internucleoside linking group is, independently, a phosphodiester or phosphorothioate.

62. The oligomeric compound of claim 33 wherein each internucleoside linking group is a phosphorothioate.

63. The oligomeric compound of claim 33 comprising at least two regions wherein each region independently comprises at least two contiguous bicyclic nucleosides having Formula III and wherein the two regions are separated by a plurality of monomeric subunits.

64. The oligomeric compound of claim 63 wherein said plurality of monomeric subunits comprise a plurality of β-D-2'-deoxyribofuranosyl nucleosides.

65. The oligomeric compound of claim 33 comprising from about 8 to about 40 monomeric subunits.

66. The oligomeric compound of claim 33 comprising from about 8 to about 20 monomeric subunits.

67. The oligomeric compound of claim 33 comprising from about 10 to about 16 monomeric subunits.

68. The oligomeric compound of claim 33 comprising from about 10 to about 14 monomeric subunits.

* * * * *